United States Patent [19]
Siegl et al.

[11] Patent Number: 5,817,658
[45] Date of Patent: Oct. 6, 1998

[54] METHOD FOR TREATING MENIERE'S DISEASE

[75] Inventors: Peter K. S. Siegl, Blue Bell; Allan I. Goldberg, North Wales; Michael R. Goldberg, Plymouth Meeting; Paul I. Chang, Doylestown, all of Pa.

[73] Assignee: Merck & Company, Inc., Rahway, N.J.

[21] Appl. No.: 881,296

[22] Filed: Jun. 24, 1997

Related U.S. Application Data

[60] Provisional application No. 60/040,796 Mar. 14, 1997.

[51] Int. Cl.⁶ .................................................. A61K 31/55
[52] U.S. Cl. ............................................................ 514/221
[58] Field of Search ............................................. 514/221

[56] References Cited

U.S. PATENT DOCUMENTS

| | | | |
|---|---|---|---|
| 5,426,185 | 6/1995 | Baldwin et al. | 540/504 |
| 5,633,251 | 5/1997 | Claremon et al. | 514/221 |
| 5,658,901 | 8/1997 | Claremon et al. | 514/221 |

OTHER PUBLICATIONS

Am. J. of Otology, vol. 14, No. 3, pp. 224–229 (1993), by J. J. Shea, Jr.
British J. of Hospital Medicine, vol. 51, No. 11, pp. 603–612 (1994), S. R. Saeed, et al.
Am. J. of Physiology, vol. 267, pp. C857–C864 (1994), by D. C. Marcus, et al.
Hearing Research, vol. 84, pp. 19–29 (1995), by Wangemann, et al.
The Merck Manual, 16th ed., pp. 2336–2337, 1992.

*Primary Examiner*—Leonard Schenkman
*Attorney, Agent, or Firm*—J. Antonio Garcia-Rivas; Valerie J. Camara; Mark R. Daniel

[57] ABSTRACT

A method for the treatment of Meniere's disease comprising the administration of a medicament which modulates the IKs channel of the ear and thereby reducing endolymph production.

7 Claims, No Drawings

METHOD FOR TREATING MENIERE'S DISEASE

BACKGROUND OF THE INVENTION

A method of treating Meniere's disease through the modulation of the IKs channel is presented.

Meniere's disease can be an incapacitating problem for patients with symptoms ranging from attacks of vertigo which appear suddenly and last from a few to 24 hours, nausea, vomiting, recurrent feeling of fullness or pressure in the affected ear, and fluctuating hearing which progressively worsens over the years. Tinnitus may be constant or intermittent and may be worse before, after or during the attack of vertigo. The etiopatho-genesis of Meniere's disease has been studied since the early 1900's and has avoided definition. Generally the disease is said to result from distention of the endolymphatic compartment of the inner ear. The primary lesion appears to be in the endolymphatic sac, which is thought to be responsible for endolymph filtration and excretion. A precise cause of hydrops has not been established. Although usually only one ear is affected, both ears are involved in 10 to 15% of patients. (MERCK MANUAL, Vol. 16, 1992).

Meniere's disease has been subdivided into five stages. Stage one is primarily diagnosed by symptoms associated with unilateral cochlear pathology focused on signs, symptoms and pathology which are singularly cochlear. Patients in this stage often respond to treatment with diuretics and dexamethasone. Once in stage two, the hydrops extends to the vestibular labyrinth and the patient begins to experience vertigo. At this stage, surgery is recommended to insert a nylon tube in the lumen of the sac to relieve the endolymphatic pressure. Streptomycin perfusion of the membranous labyrinth is also recommended at this stage. In the third stage, hearing and balance are severely compromised, and comprehension fail. Surgical treatment such as aminoglycoside destruction of the vestibular receptor or vestibular neurectomy are usually indicated. In the fourth stage, the dizziness subsides, and the endolymphatic hydrops fills the vestibule so that the endolymph pressure cannot rise. Dizziness stops at this stage, but no known medical treatment is available. At the fifth stage, widespread obstruction and ruptures in the membranous labyrinth occurs and all hearing is lost. Again no treatment is recognized once the patient has reached this stage. (REF. The America Journal of Otology, Volume 14, No. 3, May 1993, pp. 224–229).

Since Meniere's disease primarily involves distention of the endolymphatic space, modulation of endolymph production will mitigate the progression of the disease and provide relief from the symptoms previously discussed.

The concept that the stria vascularis generates an endocochlear potential and secretes $K^+$ is well accepted; however there is new information implicating an important role for $I_{Ks}K^+$ channel in endolymph production and composition. Cellular localization of $I_{sK}$, the protein which under lies the current $I_{Ks}$, in the stria vascularis of the rat has been accomplished using immunohistochemistry (Sakagami et al. Hearing Research 56: 168–172, 1991). In these studies, the $I_{sK}$ protein was present only on the endolymphatic surface of the marginal cell, consistent with involvement of $I_{Ks}$ in $K^+$ permeation in the luminal membrane of the marginal cell. Furthermore, the $K^+$ conductance measured in vestibular dark cells and apical membranes of marginal cells was found to be comprised of a high density Of $I_{Ks}$ channels(Sunose et al. Hearing Research 80:86–92, 1994; Marcus and Shen, Am. J. Physiol. 267: C857–C864, 1994; Wangemann et al. Hearing Research 84:19–29, 1995). Further, it has been determined that in its absence of the IKs channel, deftness results due to a lack of endolymph production. S. Heinemann and D. Vetter (Salk Institute), has determined that genetic knockout of IKs in mice results in vestibular dysfunction and deafness, secondary to the absence of endolymph. Recently, $I_{Ks}$ message has been found in the ear. It is now believed that modulation of the $I_{Ks}$ channel in the ear will affect endolymph production and mitigate the effects of this disease.

OBJECTS OF THE INVENTION

It is, accordingly, an object of the present invention to provide methods of treating patients suffering from Meniere's disease with compounds not previously known to have activity for this condition. Another object is to provide new methods for treating Meniere's disease. A further object is to provide pharmaceutical formulations and methods for their preparation for use in treating Meniere's disease. These and other objects of the present invention will be apparent from the following description.

SUMMARY OF THE INVENTION

A method of treating Meniere's disease in mammals, including humans which comprises blocking the slowly activating delayed rectifier potassium ($K^+$)current ($I_{Ks}$) in the ear is presented.

It has been found that compounds, which at a concentration of 1 $\mu M$ or less $IC_{50}$), block 50% of the IKs current measured in isolated myocytes and exhibit a selectivity ratio equal to or greater than 10 times the block of the $I_{Kr}$, $I_{K1}$ currents, should result in treatment which is safe and effective.

Among the compounds which exemplify this method of treatment are the 1,4-benzodiazepines or benzodiazepine derivatives that block the $I_{Ks}$ current and are therefore effective in the treatment of Meniere's disease.

DETAILED DESCRIPTION

A method of treating Meniere's disease in mammals, including humans, which comprises blocking the slowly activating delayed rectifier potassium ($K^+$)current ($I_{Ks}$) is presented. This method requires the addition of a compound which selectively blocks the IKs current and produces only minimal block of the IKr current.

Among the compounds which exemplify this method of treatment are the 1,4-benzodiazepines or benzodiazepine derivatives that block the $I_{Ks}$ current and are therefore effective in the treatment of Meniere's disease. Examples of compounds which are useful in this treatment of Meniere's disease can be found in U.S. Pat. Nos. 5,426,185; 5,633,251; and U.S. Pat. No. 5,658,901; which are hereby incorporated by reference.

Examples of compounds which are representative of selective IKs antagonists include, but are not limited to the following: Compounds represented by structural formula I

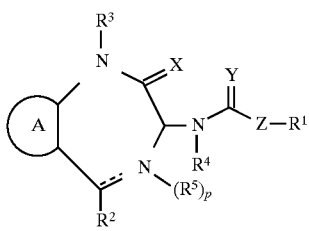

or a pharmaceutically acceptable salt thereof, wherein

A is
1) thieno,
2) pyrido, or
3) benzo either unsubstituted or substituted with $-NH_2$, $-NHSO_2$ ($C_{1-3}$ alkyl), $C_{1-3}$ alkyl or $C_{1-3}$ alkoxy;

X is
1) =O,
2) =S,
3) =N—$NH_2$,
4) =N—OH or
5) =$H_2$;

Y is
1) =O,
2) =N—CN or
3) =$H_2$;

Z is
1) $C_{1-6}$ alkylene, either straight or branch chain and either unsubstituted or substituted with phenyl or spiro-piperidine,
2) $C_{2-4}$ alkenylene, either straight or branch chain,
3) —$(CH_2)_m$—W—$(CH_2)_n$— wherein m and n are independently 0, 1, 2, 3 or 4 and W is —O—, —S— or —NH,
4) 4-(5-methylisoxazole-3-yl),
5) $C_{3-6}$ cycloalkylene, or
6) single bond;

p is
0 or 1;

$R^1$ is
1) phenyl, either unsubstituted or substituted with one or two substituents selected from
   a) —$NO_2$,
   b) —Cl, Br, F, or I,
   c) —$CF_3$,
   d) —$C_{1-3}$ alkyl,
   e) —$C_{1-3}$ alkoxy,
   f) —CN,
   g) -methylenedioxy,
2) $C_{5-7}$ cycloalkyl,
3)

4) mono- or bicyclic heterocyclyl of 5 to 10 members one or two of which are sulfur, nitrogen or oxygen, the remaining being carbon, such as 2-thienyl, 2-furanyl, 2-indolyl, 2-quinoxolinyl, or 2-(2,3-dihydro benzofuranyl)
5) $C_{1-3}$ alkyl, or
6) indan-5-yl;

$R^2$ is 1) phenyl, either unsubstituted or substituted with $C_{1-3}$ alkoxy or 4,4-dimethyloxazolin-2-yl,
2) $C_{1-6}$ alkyl, either straight or branched chain, and either unsubstituted or substituted with $C_{1-3}$ alkoxy or $C_{1-3}$ alkoxy-$C_{1-3}$ alkoxy,
3) $C_{5-7}$ cycloalkyl,
4) 2- or 3-furyl,
5) 1-methylpiperidin-2-yl, or
6) if $R^2$ is phenyl, the 2-position of the phenyl can be joined to the 4-position nitrogen of the diazepine ring through a carbonyl group and the double bond between the 4-nitrogen and the 5-carbon becomes a single bond;

$R^3$ is
1) hydrogen or
2) $C_{1-3}$ alkyl either unsubstituted or substituted with $-N(CH_3)_2$, —OH, —$CF_3$, or
3) —$CF_3$;

$R^4$ is
1) hydrogen,
2) $C_{1-6}$ alkyl, the chain of carbon atoms of which can be interrupted by one or two non-adjacent oxygen atoms and which is either unsubstituted or substituted with $C_{1-3}$ alkoxycarbonyl, —OH or

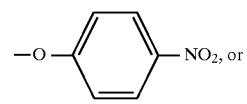

3) tetrazol-5-yl;

$R^5$ is hydrogen or oxygen or is joined to $R^2$ to form the partial structure:

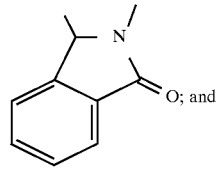

the bond represented by ———— is:
1) a double bond when p is zero or when p is 1 and $R^5$ is oxygen, or
2) a single bond when $R^5$ is hydrogen or $R^5$ is joined to $R^2$ to form the partial structure:

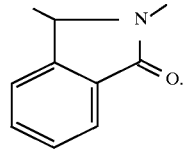

This invention is meant to include the individual diastereomers where such exist and mixtures thereof and enantiomers and mixtures of the enantiomers.

The pharmaceutically acceptable salts of the compounds of Formulas I include the conventional non-toxic salts or the quartemary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

One embodiment of this invention are novel compounds useful in the novel method of treatment of this invention wherein:

A is benzo;

X and Y are oxygen;

$R^3$ is methyl;

$R^4$ is hydrogen; and $R^2$ is $C_{1-6}$ alkyl.

Specific novel compounds representative of this embodiment are those of the following structure and specified in Table I:

TABLE I

| $R^1$ | $R^2$ |
|---|---|
| 2,4-diClPh | —$CH_3$ |
| 2,4-diClPh | —$C_2H_5$ |
| 2,4-diClPh | -t-Bu |
| 4-$CF_3$Ph | i-$C_3H_7$ |
| cyclohexyl | i-$C_3H_7$ |
| 2,4-diClPh | i-$C_3H_7$ |

Another embodiment of the compounds useful in the novel method of treatment of this invention is that wherein:

A is

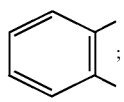

X and Y are oxygen;

$R^3$ is methyl;

$R^4$ is hydrogen; and $R^2$ is phenyl.

A class of novel compounds within this embodiment is that with structural formula:

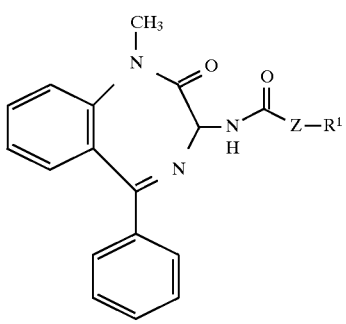

wherein

Z is $C_{1-6}$ alkylene or a bond and $R^1$ is phenyl, phenyl substituted with —Cl, —Br, —I, —F, or —$CF_3$, or $R^1$ is cyclohexyl.

Specific novel compounds representative of this class are those depicted in the following Table II:

TABLE II

| Z | $R^1$ |
|---|---|
| —$(CH_2)_2$— | 2,4-diClPh |
| —$(CH_2)_2$— | 4-ClPh |
| —$(CH_2)_2$— | 2,4-diFPh |
| —$(CH_2)_2$— | 2-ClPh |
| —$(CH_2)_2$— | 4-$CF_3$Ph |
| —$CH_2$— | 4-$CF_3$Ph |
| —$(CH_2)_2$— | 3-$CF_3$Ph |
| —$(CH_2)_2$— | 2-$CF_3$Ph |
| —$(CH_2)_2$— | cyclohexyl |
| — | cyclohexyl |
| —$(CH_2)_3$— | cyclohexyl |
| —$CH_2$— | cyclohexyl |
| —$(CH_2)_2$— | Ph |
| —$CH_2$— | Ph |
| —$(CH_2)_2$— | 4-CNPh |
| —$(CH_2)_2$— | 3-ClPh |
| —$(CH_2)_3$— | Ph |
| —$(CH_2)_2$— | 3-CNPh |
| —$(CH_2)_3$— | 2-thienyl |

Another class of novel compounds within this embodiment is that with structural formula:

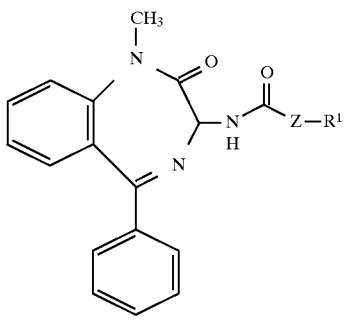

wherein Z is $C_{2-4}$ alkenylene and $R^1$ is phenyl or phenyl substituted with —Cl, —Br, —F, —I, —$CF_3$, $C_{1-3}$ alkyl, $C_{1-3}$ alkoxy or methylenedioxy.

Specific novel compounds representative of this class are those depicted in the following Table III:

TABLE III

| Z | R¹ |
|---|---|
| —CH=CH— | 4-NO₂Ph |
| —CH=CH— | 2,4-diClPh |
| —CH=CH— | 3-ClPh |
| —CH=CH— | 2-ClPh |
| —CH=CH— | 2,4-diFPh |
| —CH=CH— | 2,6-diClPh |
| —CH=CH— | 4-CF₃Ph |
| —CH=CH— | 2-BrPh |
| —CH=CH— | 4-Ph |
| —CH=CH— | 4-BrPh |
| —C(CH₃)=CH— | Ph |
| —CH=CH— | Ph* |
| —CH=CH— | 3,4-diClPh |
| —CH=CH— | 4-CH₃Ph |
| —CH=CH— | 4-CH₃OPh |
| —CH=CH— | 3,4-methylenedioxyPh |
| —CH=CH— | 3-BrPh |

*This compound is disclosed in U.S. Pat. No. 4,820,834

A third embodiment of the compounds useful in the novel method of treatment of this invention is that wherein: Z is —NH—.

Compounds representative of this embodiment are those disclosed in the following Table IV.

TABLE IV

| A | R¹ | R² | R³ | Y |
|---|---|---|---|---|
| benzo | 3-CH₃Ph | Ph | ⸍⸜OH | O |
| benzo | 2,4-diClPh | Ph | —CH₃ | O |
| benzo | 3-CH₃Ph | | n-C₃H₇ | O |
| benzo | —CH₂ Cyclohexyl | Ph | —CH₃ | =N—CN |
| benzo | 3-CH₃Ph | Ph | —CH₃ | O |
| benzo | 5-indanyl | Ph | ⸍⸜OH | O |
| (thienyl) | 3-CH₃Ph | Ph | —CH₃ | O |

Other specific compounds included within the broadest genus but not included in one of the embodiments previously described are as shown in Table V.

TABLE V

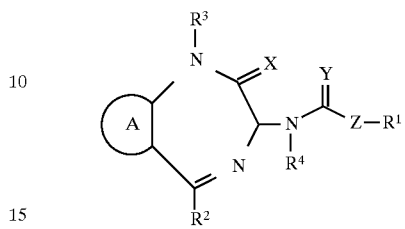

Representative of compounds wherein p is 1 is the compound of structural formula:

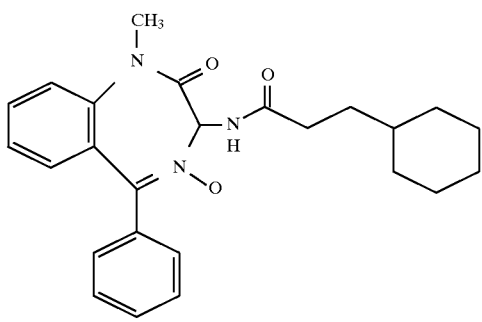

Representative of compounds wherein the bond between the 4 and 5 positions is a single bond is the compound of structural formula:

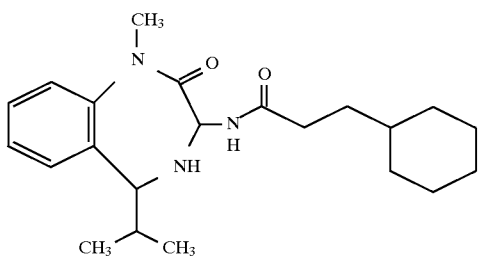

Representative of compounds wherein the bond ══════ represents a single bond and $R^5$ is joined to $R^2$ is the compound of structural formula:

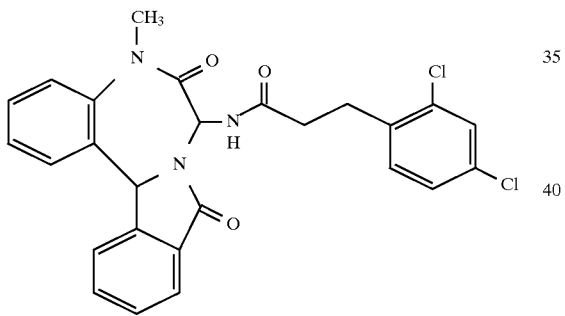

Another embodiment of this invention is a group of compounds, active in the novel method of treatment of this invention, which are novel compounds per se. These novel compounds are depicted in the following Table VI.

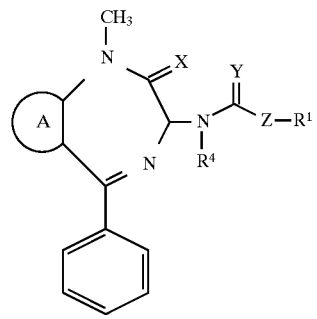

Another embodiment of this invention is a group of compounds which are active in the novel method of treatment of this invention. These compounds are depicted as follows:

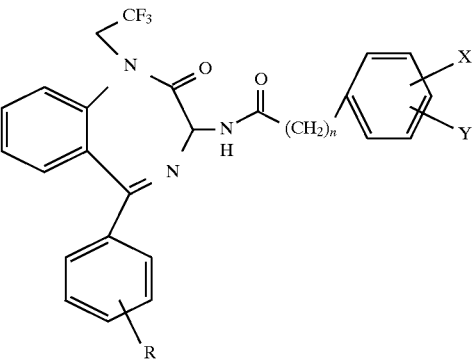

where
X and Y are independently hydrogen, chloro, fluoro, bromo, iodo, or trifluoromethyl and
n is 0, 1 or 2;
R is hydrogen, fluoro, chloro, bromo, iodo, or trifluoromethyl, methyl, or methoxy; and
the racemates, mixtures of enantiomers, individual diastereomers or individual enantiomers with all isomeric forms and pharmaceutically acceptable salts, hydrates or crystal forms thereof, which are effective in the treatment of Meniere's disease.

Yet another embodiment of this invention is a group of compounds which are active in the novel method of treatment of this invention. These compounds are depicted as follows:

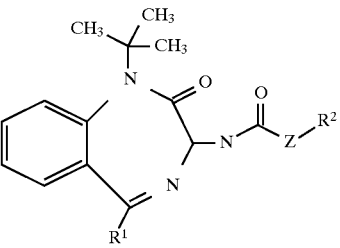

$R^1$ and $R^2$ are independently
1) phenyl, either unsubstituted or substituted with one or two substituents selected from
a) —$NO_2$, OH,
b) —Cl, Br, F, or I,
c) —$CF_3$,
d) —$C_{1-3}$ alkyl,
e) —$C_{1-3}$ alkoxy,
f) —CN,
g) -methylenedioxy, and Z is
1) $C_{1-6}$ alkyl, either straight or branched chain,
2) substituted $C_{1-6}$ alkyl, either straight or branched chain, wherein the substituents are selected from F, OH, $NO_2$,
3) $C_{2-4}$ alkenylene, either straight or branched chain,
4) —$(CH_2)_m$—W—$(CH_2)_n$— wherein m and n are independently 0, 1, 2, 3 or 4 and W is —O—, —S— or —NH,
5) $C_{3-6}$ cycloalkane,
6) $C_{3-6}$ cycloalkylene, or
7) single bond;

The $I_{Ks}$ blockers or selective $I_{Ks}$ antagonists of the present invention have the pharmacological properties required for antiarrhythmic agents of Class III, namely they demonstrate prolongation of QTc-interval, and dose dependent increases in ventricular refractoriness. This is accomplished without effecting heart rate, mean arterial pressure and PR and QRS intervals. Modest increases in LV+dP/dt (left ventricular change in pressure with time) is observed. Further, these compounds suppress the induction of PVS (Programmed Ventricular Stimulation) induced ventricular tachyarrhythmias.

The compounds of the present invention are especially useful for controlling and treating Meniere's disease via modulation of endolymph production.

In the novel method of this invention of treating Meniere's disease a selective $I_{K_s}$ antagonist is administered in an amount ranging from about 0.0001 to about 10 mg per kg of body weight per day, preferably from about 0.0001 to about 2 mg per kg of body weight per day, and more preferably, when intravenous delivery of the compounds is employed, from about 0.0003 to about 0.3 mg per kg of body weight per day, or when given orally from about 0.01 to about 1 mg per kg of body weight per day, in a single dose or in 2 to 4 divided doses of each compound.

The activity of the compounds described herein as agents which treat Meniere's disease is measured by their ability to block the $I_{K_s}$ and $I_{K_r}$ currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier $K^+$ current: differential sensitivity to block by Class III antiarrhythmic agents. J. Gen Physiol. 96: 195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4KCl, 1.2 MgCl$_2$, 10 HEPES, 10 glucose: pH 7.2, temp. 35° C.

Each cell is maintained at a holding potential of –50 mV. Test depolarizations are applied as voltage ramps from –85 to –50 mV, and as steps to –10 mV (0.5 s) and +50 mV (1.0 s). $I_{KI}$ is measured as peak outward current during the voltage ramp. $I_{Kr}$ is measured as tail currents upon repolarization from –10 mV to –50 mV. $I_{K_s}$ is measured as time-dependent current during the pulse to +50 mV. Currents are measured during control, then after exposure to drug at two different concentrations.

Employing this test the compounds described herein as selective $I_{K_s}$ blockers have an IC$_{50}$ of less than 100 nM as $I_{K_s}$ blockers. The compounds of this invention are at least 10 times more potent in the blockade of $I_{K_s}$ than of blockade of $I_{Kr}$.

The utility of the compounds of this invention to combat Meniere's disease via modulation of endolymph production is shown by the lack of endolymph production when there is an absence of functional $I_{K_s}$ channels (i.e. $I_{sK}$ knockout mouse) and the effect of chronic administration of exemplified compounds on membranous structures in the ear of rats.

Further evidence for this utility is obtained from experimentally induced of endolymphatic hydrops in animals.

Typical synthetic schemes employed in making the compounds herein are illustrated below.

SCHEME 1

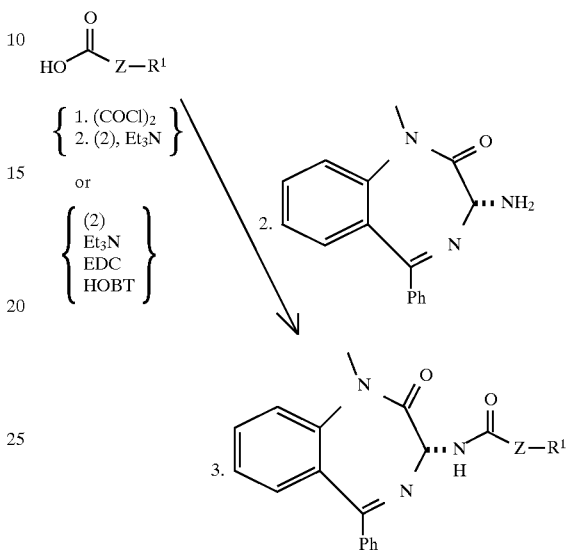

SCHEME 2

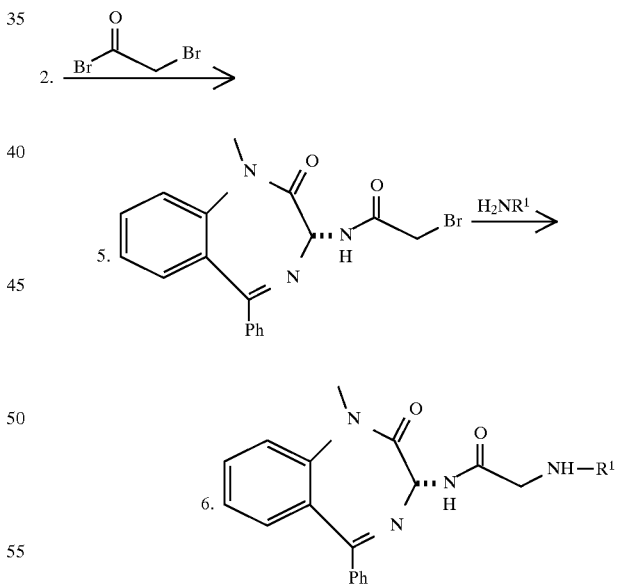

SCHEME 3
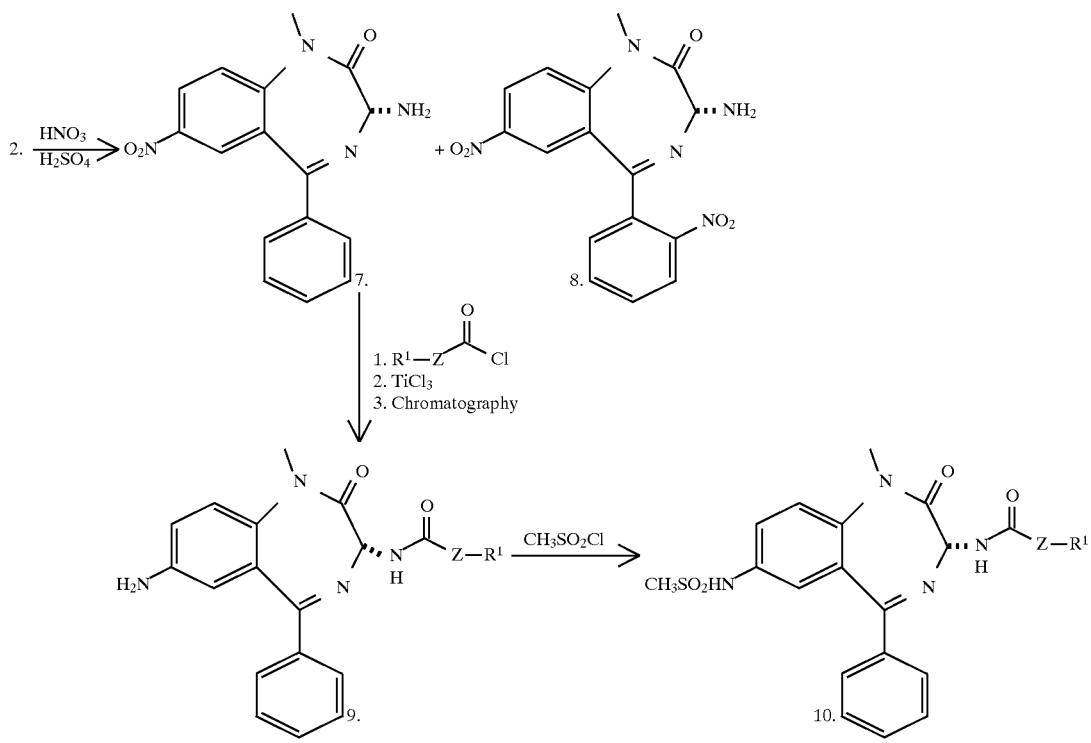
SCHEME 4
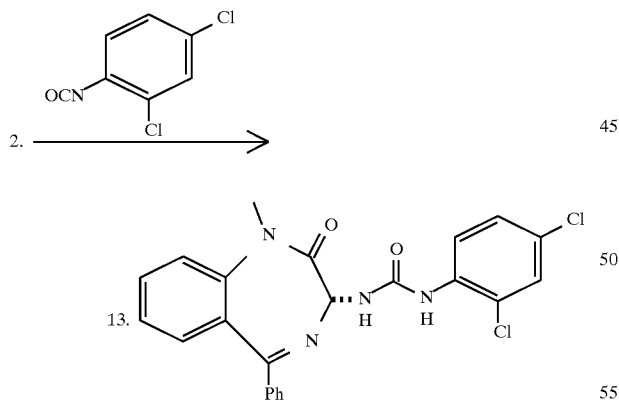
SCHEME 5
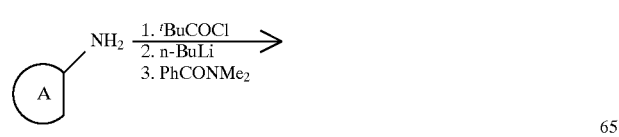
-continued
SCHEME 5
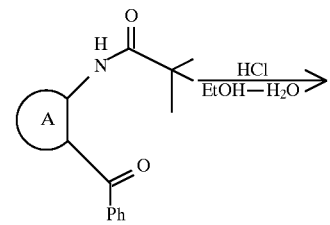
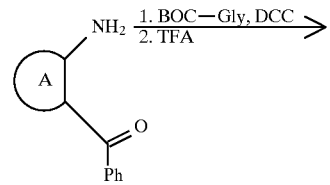
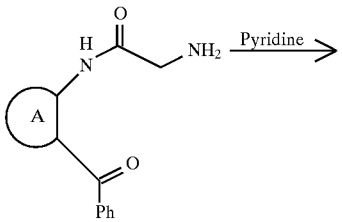

15
-continued
SCHEME 5
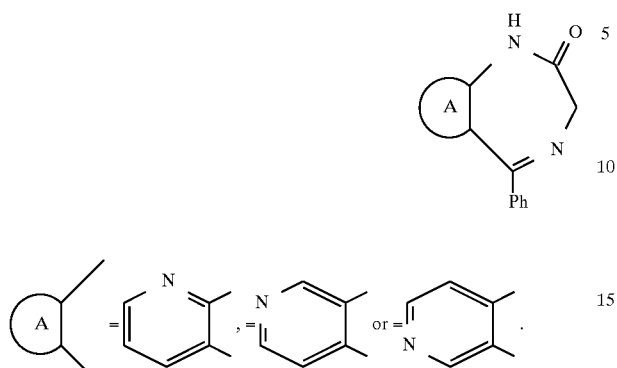
SCHEME 6
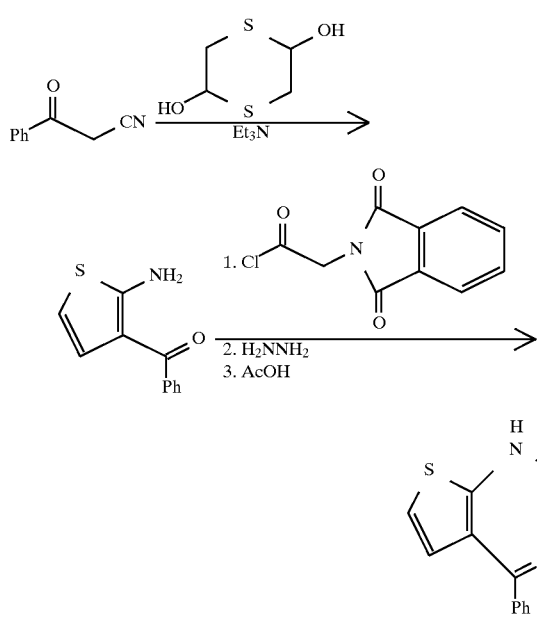
SCHEME 7
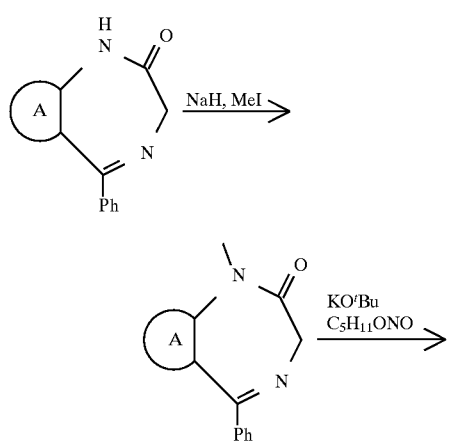
16
-continued
SCHEME 7
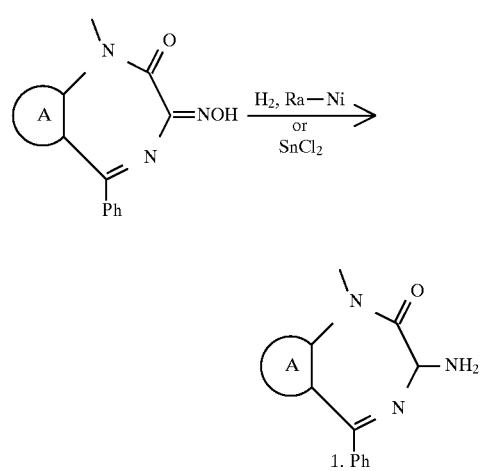
SCHEME 8
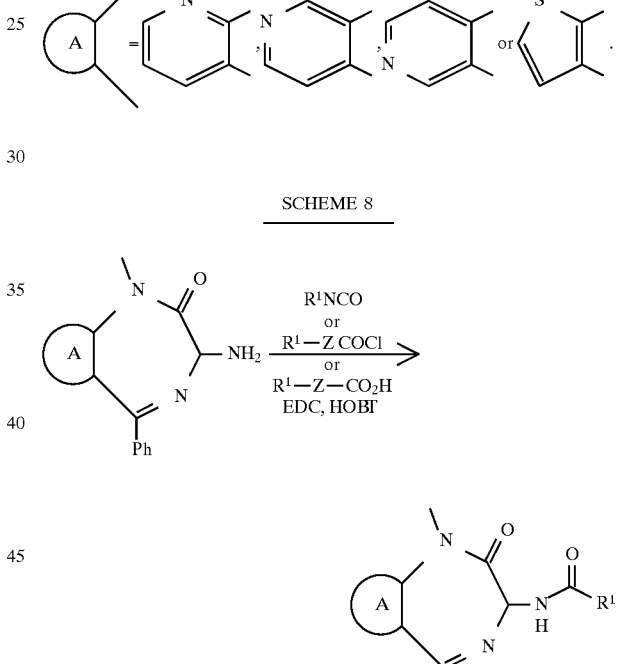
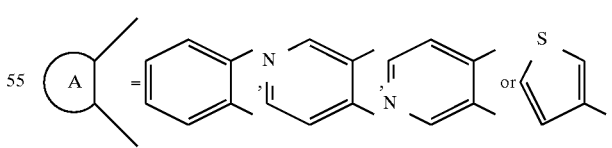

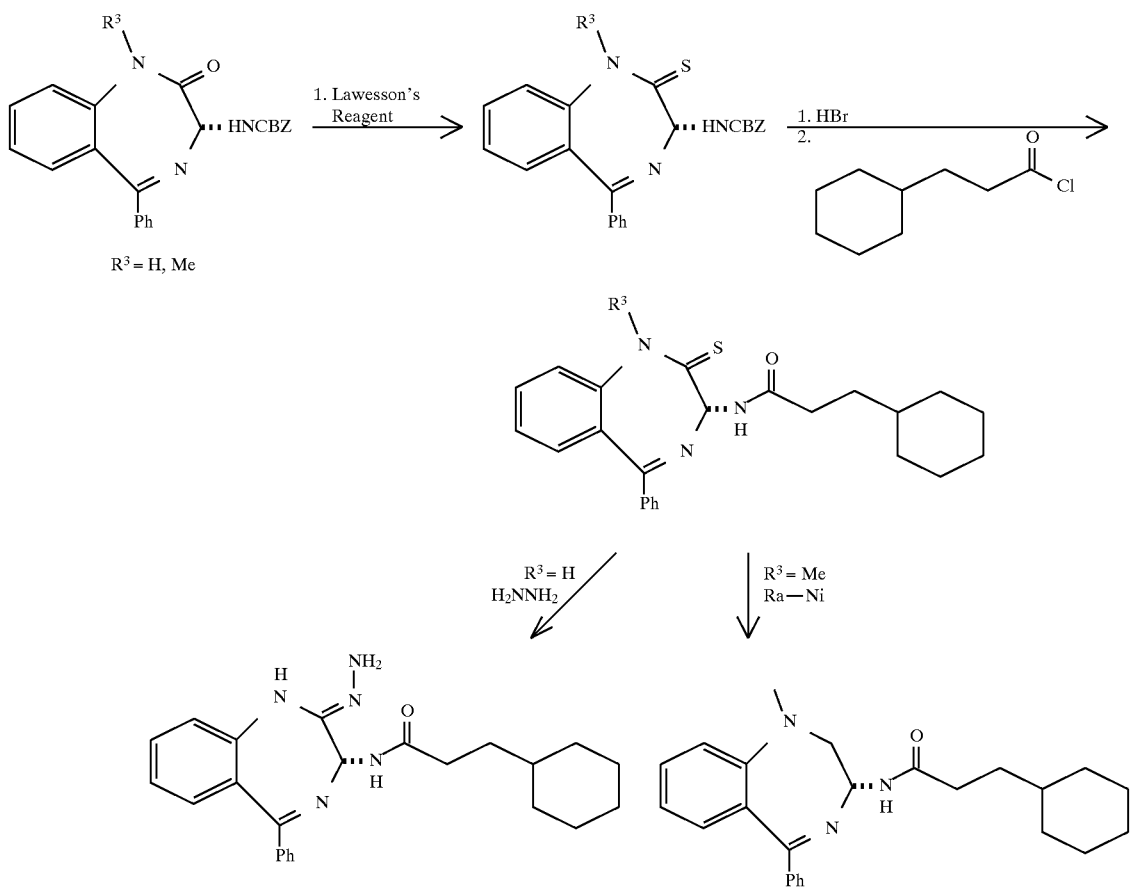
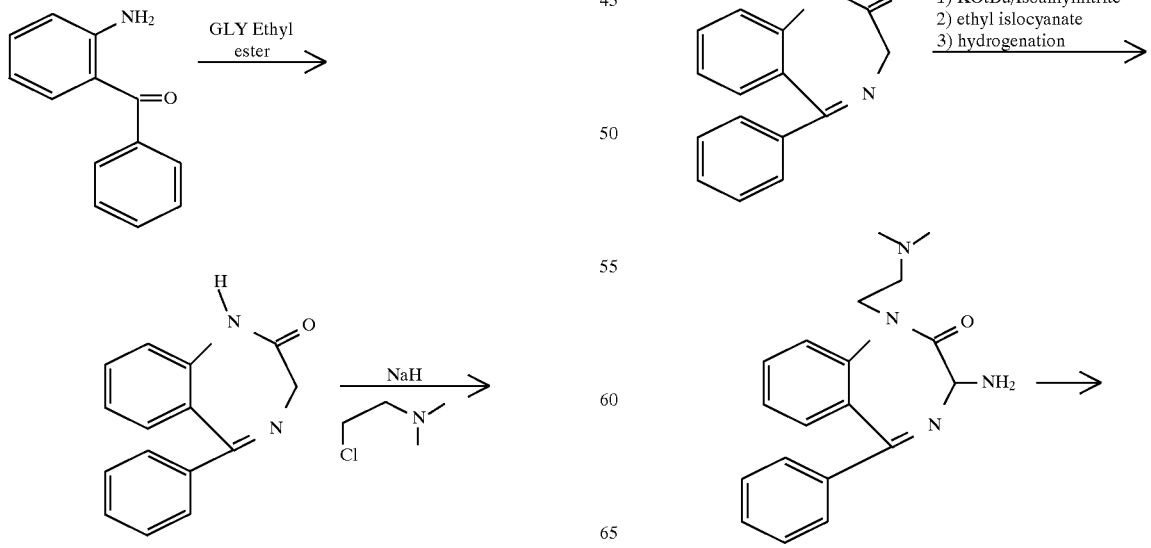

SCHEME 10 -continued
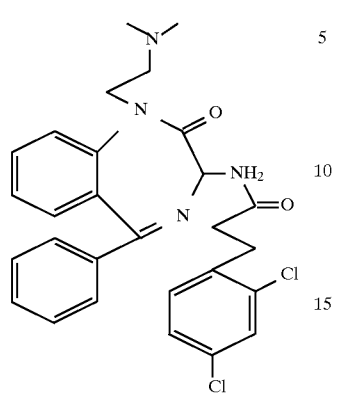
SCHEME 12
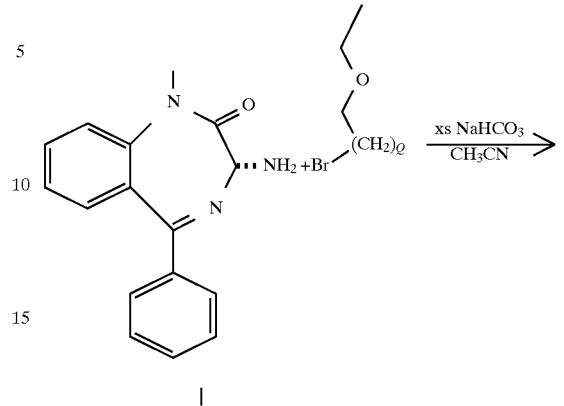
SCHEME 11
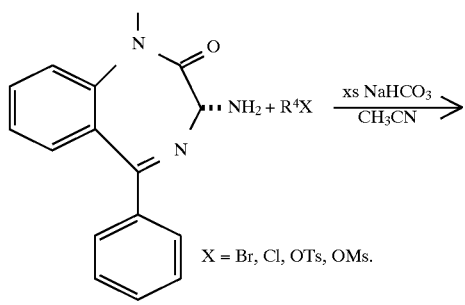
X = Br, Cl, OTs, OMs.
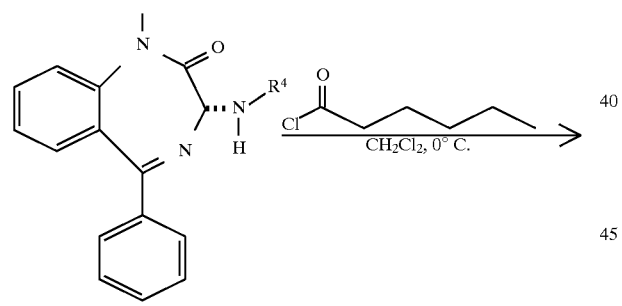
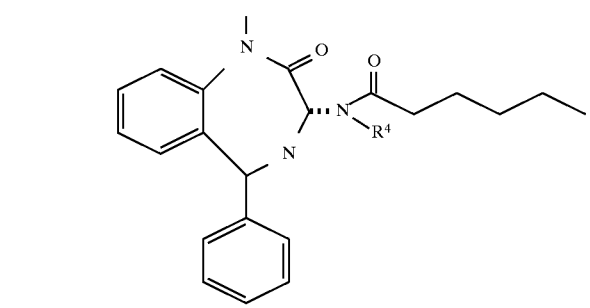
SCHEME 13
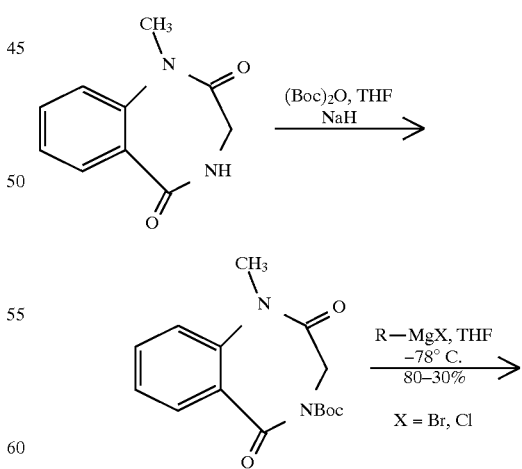
X = Br, Cl -continued
SCHEME 13
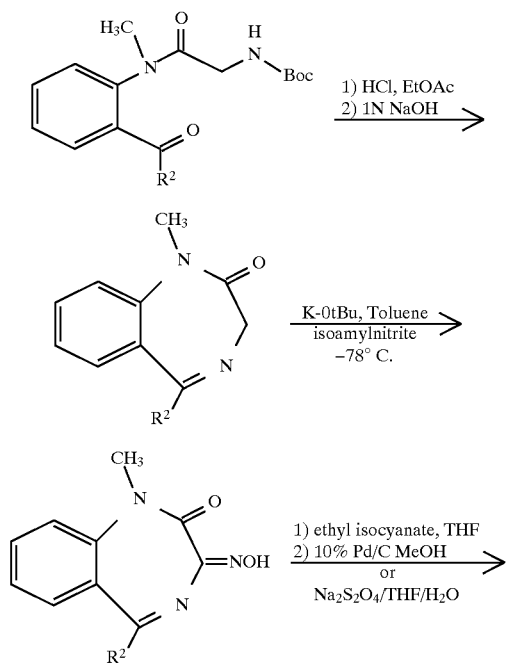
-continued
SCHEME 14
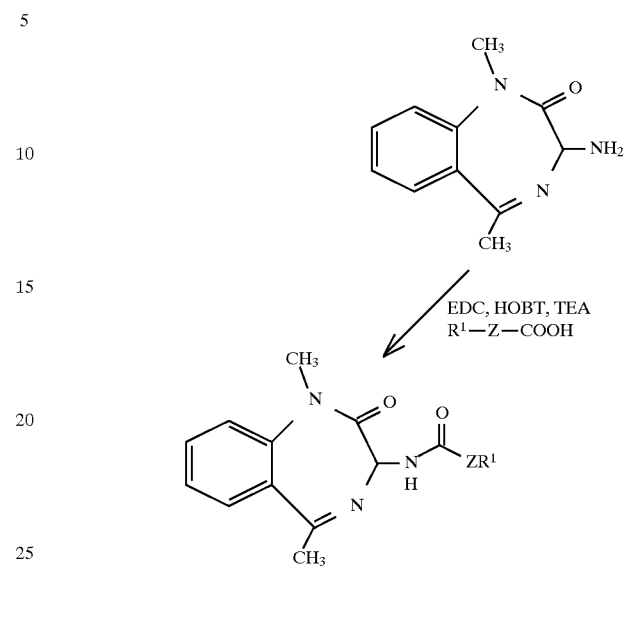
SCHEME 15
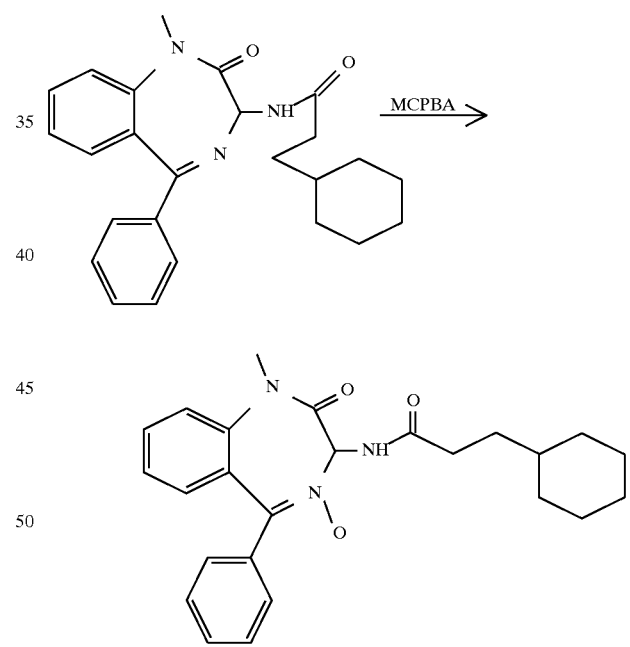
SCHEME 14
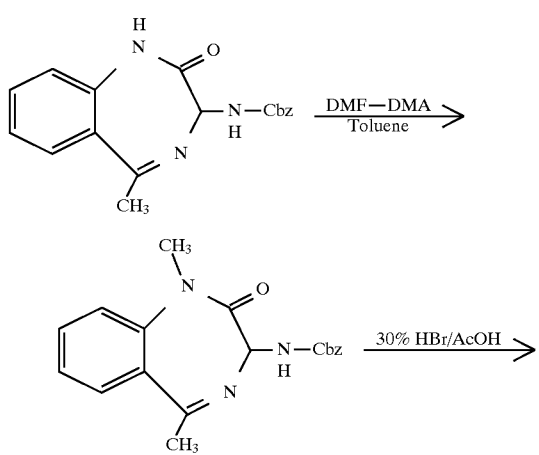

SCHEME 16
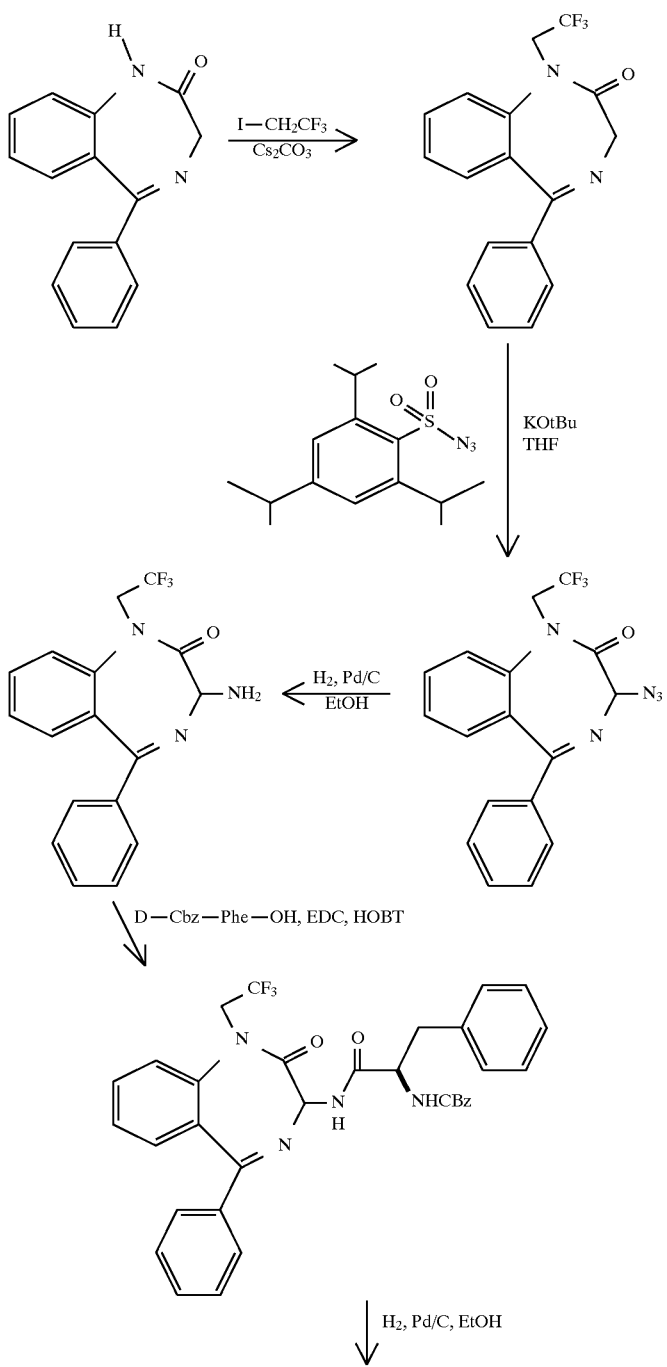

-continued
SCHEME 16
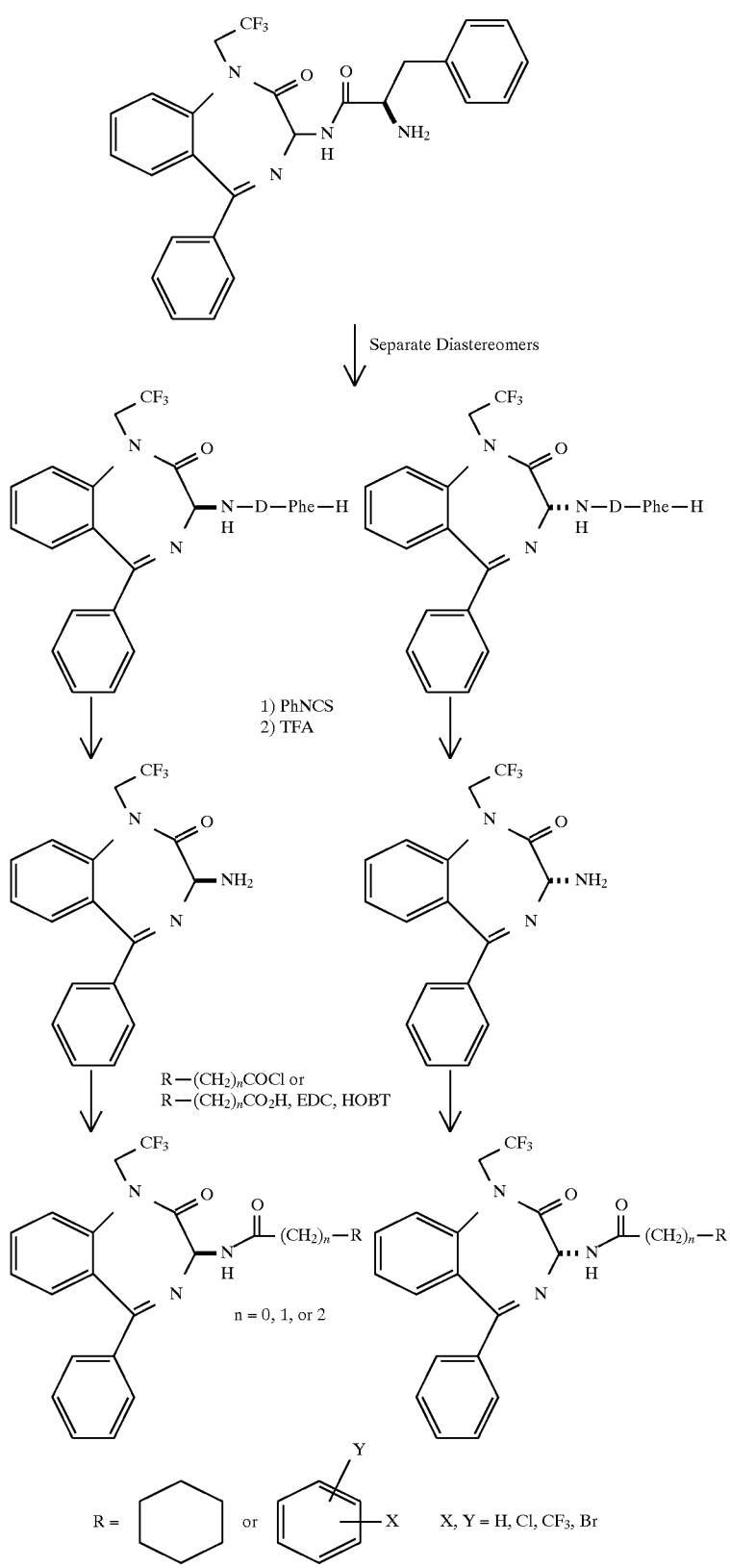

EXAMPLES

Example 1

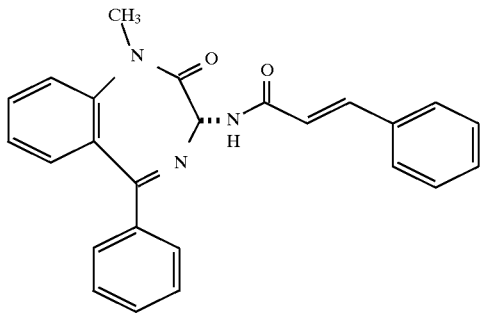

(E)-(+)-N-[(3R)-2,3-Dihydro-1-methyl-2-oxo-5-phenyl-1H-1,4-benzodiazepin-3-yl]-3-phenyl-2-propenamide A solution of (E)-3-phenyl-2-propenoyl chloride (367 mg, 2.2 mmol) in methylene chloride (1 mL) was added to a solution of 3(R)-amino-1,3-dihydro-1-methyl-5-phenyl-2H-1,4-benzodiazepin-2-one (*J. Org. Chem.* 1987, 52, 3232–3239) (531 mg, 2.0 mmol) and triethylamine (307 mL, 225 mg, 2.2 mmol) in methylene chloride (10 mL). The mixture was stirred at room temperature for 25 min. and the solvent was evaporated under reduced pressure. The residue was purified by flash column chromatography on silica gel, eluting with $CH_2Cl_2/Et_2O$ (95:5) and the residue was triturated with $Et_2O$. The solid was collected and dried in vacuo at 70° C. to give (E)-(+)-N-[(3R)-2,3-dihydro-1-methyl-2-oxo-5-phenyl-1H-1,4-benzodiazepin-3-yl]-3-phenyl-2-propenamide as a colorless solid (170 mg, 21%), m.p. 140°–142° C., $[\alpha]_D$+86.7° (c=0.173, $CH_2Cl_2$).

$^dH(CDCl_3)$ 7.70–7.26 (16H, m), 6.63 (1H, d, J 15.6 Hz), 5.68 (1H, d, J 8.3 Hz), and 3.50 (3H, s). Anal. Calcd. for $C_{25}H_{21}N_3O_2.0.15 (C_2H_5)_2O$: C, 75.63; H, 5.58; N, 10.33. Found: C, 75.29; H, 5.57; N, 10.33%.

Employing the procedure substantially as described above, but substituting an appropriate acid chloride for the (E)-3-phenyl-2-propenoyl chloride, the following compounds were prepared:

Example 2

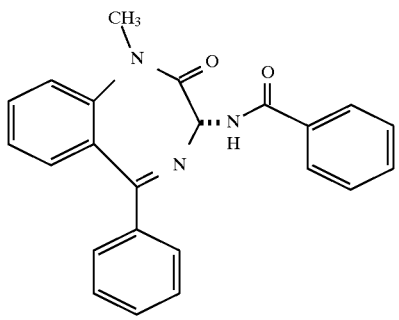

(+)-N-[(3R)-2,3-Dihydro-1-methyl-2-oxo-5-phenyl-1H-1,4-benzodiazepin-3-yl]benzamide m.p. 224°–225° C., $[\alpha]_D$+89.2° (c=0.141, $CH_2Cl_2$). $^dH$ $(CDCl_3)$ 8.04 (1H, d, J 8.1 Hz), 7.96 (2H, d, J 6.8 Hz), 7.64–7.36 (10H, m), 7.27 (2H, t, J 7.6 Hz), 5.74 (1H, d, J 7.8 Hz), and 3.51 (3H, s). Anal. Calcd. for $C_{23}H_{19}N_3O_2.0.20H_2O$: C, 74.06; H, 5.24; N, 11.26. Found: C, 74.13; H, 5.12; N, 11.16%.

Example 3

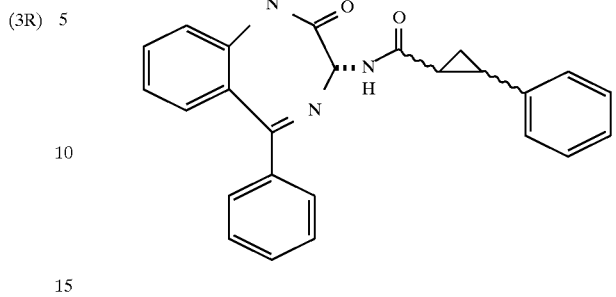

First diastereoisomer to elute:

(−)-N-[(3R)-2,3-Dihydro-1-methyl-2-oxo-5-phenyl-1H-1,4-benzodiazepin-3-yl](trans-2-phenyl-1-cyclopropane)carboxamide m.p. 180°–181° C., $[\alpha]_D$−155.8° (c=0.434, $CH_2Cl_2$). $^dH$ $(CDCl_3)$ 7.62–7.09 (15H, m), 5.59 (1H, d, J 8.1 Hz), 3.47 (3H, s), 2.52–2.45 (1H, m), 1.90–1.84 (1H, m), 1.69–1.56 (1H, m), and 1.38–1.32 (1H, m). Anal. Calcd. for $C_{26}H_{23}N_3O_2.0.25H_2O$: C, 75.43; H, 5.72; N, 10.15. Found: C, 75.38; H, 5.64; N, 9.94%.

Second diastereoisomer to elute:

(+)-N-[(3R)-2,3-Dihydro-1-methyl-2-oxo-5-phenyl-1H-1,4-benzodiazepin-3-yl](trans-2-phenyl-1-cyclopropane)carboxamide m.p. 104°–107° C., $[\alpha]_D$+328.2° (c=0.098, $CH_2Cl_2$). $^dH$ $(CDCl_3)$ 7.62–7.13 (15H, m), 5.60 (1H, d, J 8.3 Hz), 3.48 (3H, s), 2.59–2.54 (1H, m), 1.93–1.87 (1H, m), 1.62–1.56 (1H, m, overlaps with water), and 1.33–1.25 (1H, m). Anal. Calcd. for $C_{26}H_{23}N_3.0.50H_2O.0.45PhCH_3$: C, 76.13; H, 5.95; N, 9.14. Found: C, 76.10; H, 5.94; N, 9.17%.

Example 4

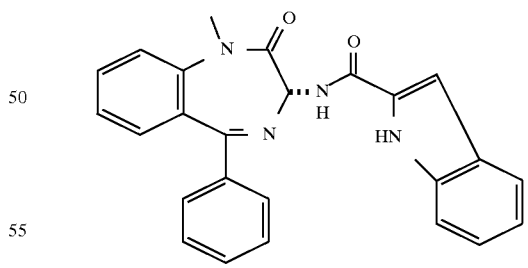

(+)-N-[(3R)-2,3-Dihydro-1-methyl-2-oxo-5-phenyl-1H-1,4-benzodiazepin-3-yl]-1H-indole-2-carboxamide m.p. 167°–177° C., $[\alpha]_D$+113° (c=1.103, $CH_2Cl_2$). $^dH$ $(CDCl_3)$ 9.15 (1H, br s), 8.10 (1H, d, J 9.0 Hz), 7.75–7.10 (14H, m), 5.75 (1H, d, J 9.0 Hz), and 3.50 (3H, s). Anal. Calcd. for $C_{25}H_{20}N_4O_2$: C, 73.51; H, 4.94; N, 13.72. Found: C, 73.31; H, 4.80; N, 13.62%.

Example 5

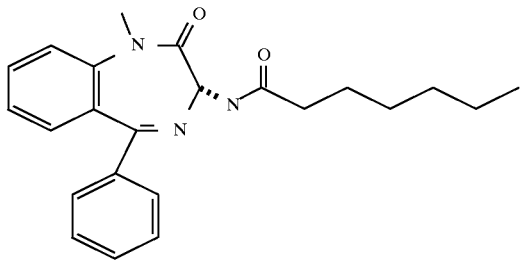

(+)-N-[(3R)-2,3-Dihydro-1-methyl-2-oxo-5-phenyl-1H-1,4-benzodiazepin-3-yl]heptanamide m.p. 49°–54° C., $[\alpha]_D$+69.5° (c=1.000, MeOH). Anal. Calcd. for $C_{23}H_{27}N_3O_2 \cdot 0.40H_2O$: C, 71.81; H, 7.28; N, 10.92. Found: C, 71.90; H, 7.09; N, 10.85%.

Example 6

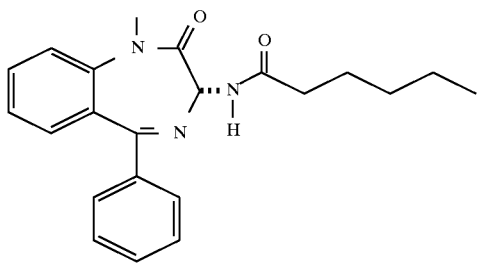

(+)-N-[(3R)-2,3-Dihydro-1-methyl-2-oxo-5-phenyl-1H-1,4-benzodiazepin-3-yl]hexanamide $[\alpha]_D$+72.6° (c=0.920, MeOH). Anal. Calcd. for $C_{22}H_{25}N_3O_2$: C, 72.70; H, 6.93; N, 11.56. Found: C, 72.44; H, 6.75; N, 11.25%.

Example 7

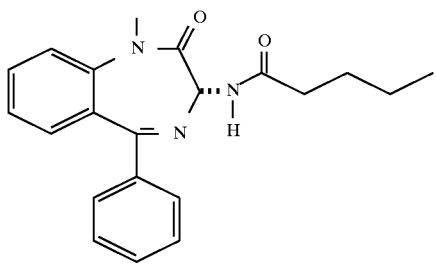

(+)-N-[(3R)-2,3-Dihydro-1-methyl-2-oxo-5-phenyl-1H-1,4-benzodiazepin-3-yl]pentanamide $[\alpha]_D$+68.2° (c=1.310, MeOH). Anal. Calcd. for $C_{21}H_{23}N_3O_2 \cdot 0.25CHCl_3$: C, 68.21; H, 6.26; N, 11.26. Found: C, 68.2; H, 6.29; N, 11.17%.

Example 8

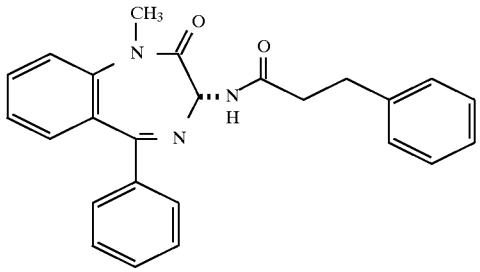

(+)-N-[(3R)-2,3-Dihydro-1-methyl-2-oxo-5-phenyl-1H-1,4-benzodiazepin-3-yl]-3-phenylpropanamide Oxalyl chloride (158 mL, 230 mg, 1.81 mmol) was added to a mixture of 3-phenylpropanoic acid (249 mg, 1.66 mmol) and DMF (1 drop) in THF (10 mL) and the mixture was stirred at room temperature for 40 min. 3(R)-Amino-1,3-dihydro-1-methyl-5-phenyl-2H-1,4-benzodiazepin-2-one (J. Org. Chem. 1987, 52, 3232–3239) (400 mg, 1.51 mmol) and triethylamine (252 mL, 183 mg, 1.81 mmol) were added and the mixture was stirred at room temperature for 18 h. The mixture was poured into saturated aqueous sodium hydrogen carbonate (20 mL) and extracted with ethyl acetate (3×20 mL). The combined organic fractions were dried ($Na_2SO_4$) and the solvent was evaporated under reduced pressure. The residue was purified by flash column chromatography on silica gel, eluting with $CH_2Cl_2/Et_2O$ (95:5) and the residue was recrystallized from toluene/hexane to give (+)-N-[(3R)-2,3-dihydro-1-methyl-2-oxo-5-phenyl-1H-1,4-benzodiazepin-3-yl]-3-phenylpropanamide as a colorless solid (380 mg, 63%). m.p. 179° C., $[\alpha]_D$+100.4° (c=0.225, $CH_2Cl_2$). $^dH$ (CDCl$_3$) 7.62–7.57 (2H, m), 7.47–7.21 (13H, m), 5.54 (1H, d, J 8.1 Hz), 3.47 (3H, s), 3.03 (2H, t, J 7.8 Hz), and 2.73–2.67 (2H, m).

Anal. Calcd. for $C_{25}H_{23}N_3O_2 \cdot 0.15H_2O$ : C, 75.04; H, 5.87; N, 10.50. Found: C, 75.06; H, 5.78; N, 10.55%.

Employing the procedure substantially as described above, but substituting an appropriate carboxylic acid for the 3-phenyl-propanoic acid, the following compounds were prepared:

Example 9

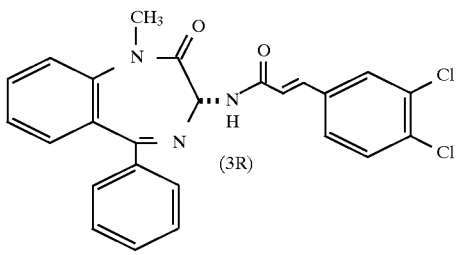

E-(+)-N-[(3R)-2,3-Dihydro-1-methyl-2-oxo-5-phenyl-1,4-benzodiazepin-3-yl]-3-(3,4-dichlorophenyl)-2-propenamide m.p. 145°–147° C., $[\alpha]_D$+77.8° (c=0.126, $CH_2Cl_2$). $^dH$ (CDCl$_3$) 7.64–7.25 (14H, m), 6.61 (1H, d, J 15.6 Hz), 5.65 (1H, d, J 8.0 Hz), and 3.50 (3H, s). Anal. Calcd. for $C_{25}H_{19}N_3O_2Cl_2$: C, 64.67; H, 4.12; N, 9.05. Found: C, 64.57; H, 4.25; N, 9.01%.

Example 10

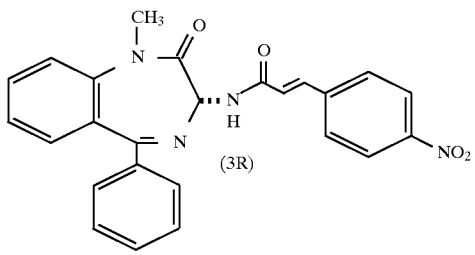

(3R)

E-(+)-N-[(3R)-2,3-Dihydro-1-methyl-2-oxo-5-phenyl-1H-1,4-benzodiazepin-3-yl]3-(4-nitrophenyl)-2-propenamide m.p. 165°–166° C., $[\alpha]_D$+80.5° (c=0.126, CH$_2$Cl$_2$). $^d$H (CDCl$_3$) 8.26 (1H, d, J 8.8 Hz), 7.74–7.28 (13H, m), 6.76 (1H, d, J 15.6 Hz), 5.66 (1H, d, J 8.0 Hz), and 3.51 (3H, s). Anal. Calcd. for C$_{25}$H$_{19}$N$_4$O$_4$: C, 68.17; H, 4.58; N, 12.72. Found: C, 68.25; H, 4.65; N, 12.57%.

Example 11

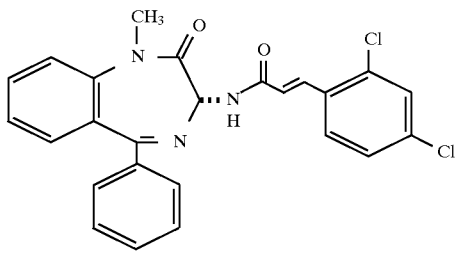

E-(+)-N-[(3R)-2,3-Dihydro-1-methyl-2-oxo-5-phenyl-1H-1,4-benzodiazepin-3-yl]-3-(2,4-dichlorophenyl)-2-propenamide m.p. 137°–139° C., $[\alpha]_D$+66.0° (c=0.144, CH$_2$Cl$_2$). $^d$H (CDCl$_3$) 8.02 (1H, d, J 15.6 Hz), 7.73–7.26 (13H, m), 6.66 (1H, d, J 15.6 Hz), 5.81 (1H, d, J 8.8 Hz), and 3.53 (3H, s). Anal. Calcd. for C$_{25}$H$_{19}$Cl$_2$N$_3$O$_2$: C, 64.67; H, 4.12; N, 9.05. Found: C, 64.28; H, 4.24; N, 8.83%.

Example 12

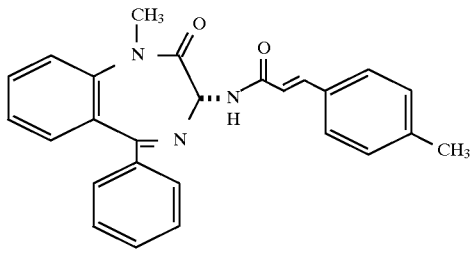

E-(+)-N-[(3R)-2,3-Dihydro-1-methyl-2-oxo-5-phenyl-1H-1,4-benzodiazepin-3-yl]-3-(4—methylphenyl)-2-propenamide m.p. 133°–135° C., $[\alpha]_D$+90.4° (c=0.125, CH$_2$Cl$_2$). $^d$H (CDCl$_3$) 7.68–7.19 (15H, m), 6.59 (1H, d, J 15.6 Hz), 5.70 (1H, d, J 8.0 Hz), 3.50 (3H, s), and 2.38 (3H, s). Anal. Calcd. for C$_{26}$H$_{23}$N$_3$O$_2$: C, 76.26; H, 5.66; N, 10.26. Found: C, 75.93; H, 5.82; N, 10.10%.

Example 13

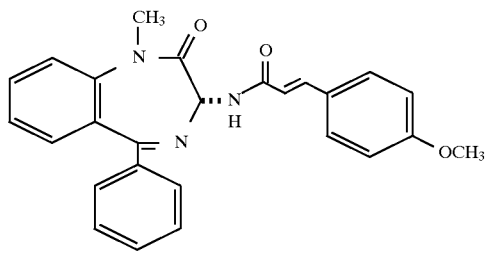

E-(+)-N-[(3R)-2,3-Dihydro-1-methyl-2-oxo-5-phenyl-1H-1,4-benzodiazepin-3-yl]-3-(4-methoxyphenyl)-2-propenamide m.p. 129°–133° C., $[\alpha]_D$+89.9° (c 0.188, CH$_2$Cl$_2$). $^d$H (CDCl$_3$) 7.65–7.24 (14H, m), 6.92 (1H, d, J 8.8 Hz), 6.50 (1H, d, J 15.6 Hz), 5.69 (1H, d, J 8.0 Hz), 3.84 (3H, s), and 3.50 (3H, s). Anal. Calcd. for C$_{26}$H$_{23}$N$_3$O$_3$.0.30H$_2$O: C, 72.48; H, 5.52; N, 9.75. Found: C, 72.75; H, 5.60; N, 9.36%.

Example 14

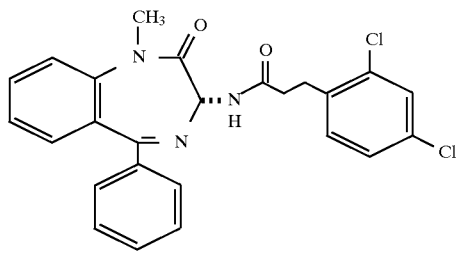

(+)-N-[(3R)-2,3-Dihydro-1-methyl-2-oxo-5-phenyl-1H-1,4-benzodiazepin-3-yl]-3-(2,4-dichlorophenyl)propanamide m.p. 92°–95° C., $[\alpha]_D$ 90.5° (c=0.196, CH$_2$Cl$_2$). $^d$H (CDCl$_3$) 7.62–7.15 (13H, m), 5.52 (1H, d, J 8.1 Hz), 3.47 (3H, s), 3.10 (2H, t, J 7.6 Hz), and 2.68 (2H, dd, J 7.6, 2.8 Hz). Anal. Calcd. for C$_{25}$H$_{21}$Cl$_2$N$_3$O$_2$.0.20H$_2$O: C, 63.89; H, 4.59; N, 8.94. Found: C, 63.86; H, 4.62; N, 8.87%.

Example 15

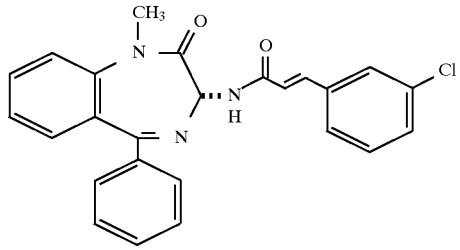

E-(+)-N-[(3R)-2,3-Dihydro-1-methyl-2-oxo-5-phenyl-1H-1,4-benzodiazepin-3-yl]-3-(3-chlorophenyl)-2-propenamide
m.p. 229°–231° C., $[\alpha]_D$+86.2° (c=0.225, CH$_2$Cl$_2$). $^d$H (CDCl$_3$) 7.64–7.26 (15H, m), 6.62 (1H, d, J 15.6 Hz), 5.66 (1H, d, J 8.1 Hz), and 3.50 (3H, s). Anal. Calcd. for C$_{25}$H$_{20}$ClN$_3$O$_2$: C, 69.85; H, 4.69; N, 9.77. Found: C, 70.20; H, 4.83; N, 9.41%.

Example 16

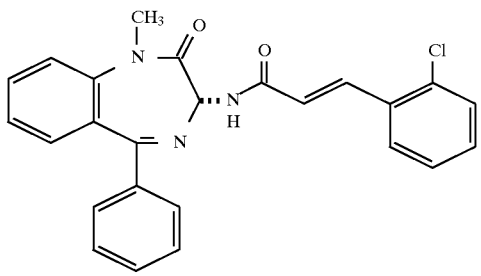

E-(+)-N-[(3R)-2,3-Dihydro-1-methyl-2-oxo-5-phenyl-1H-1,4-benzodiazepin-3-yl]-3-(2-chlorophenyl)-2-propenamide
m.p. 128°–131° C., $[\alpha]_D$=+61.7° (c=0.196, $CH_2Cl_2$). $^dH$ ($CDCl_3$) 8.06 (1H, d, J 15.6 Hz), 7.65–7.28 (14H, m), 6.62, (1H, d, J 15.6 Hz), 5.68 (1H, d, J 8.3 Hz), and 3.50 (3H, s). Anal. Calcd. for $C_{25}H_{20}ClN_3O_2 \cdot 0.20H_2O$: C, 69.27; H, 4.74; N, 9.69. Found: C, 69.21; H, 4.68; N, 9.45%.

Example 17

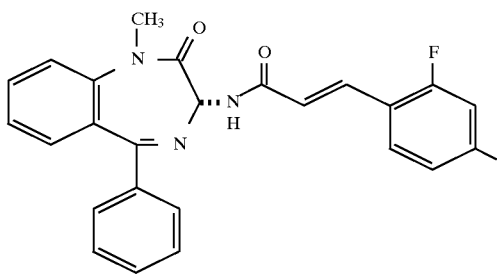

E-(+)-N-[(3R)-2,3-Dihydro-1-methyl-2-oxo-5-phenyl-1H-1,4-benzodiazepin-3-yl]-3-(2,4-difluorophenyl)-2-propenamide
m.p. 121°–123° C., $[\alpha]_D$+76.8° (c=0.111, $CH_2Cl_2$). $^dH$ ($CDCl_3$) 7.71 (1H, d, J 15.9 Hz), 7.64–7.24 (11H, m), 6.92–6.84 (2H, m), 6.69 (1H, d, J 15.9 Hz), 5.67 (1H, d, J 8.1 Hz), and 3.50 (3H, s). Anal. Calcd. for $C_{25}H_{19}F_2N_3O_2 \cdot 0.10H_2O$: C, 69.3 1; H. 4.47; N. 9.70. Found: C, 69.28; H. 4.57; N. 9.3 1%.

Example 18

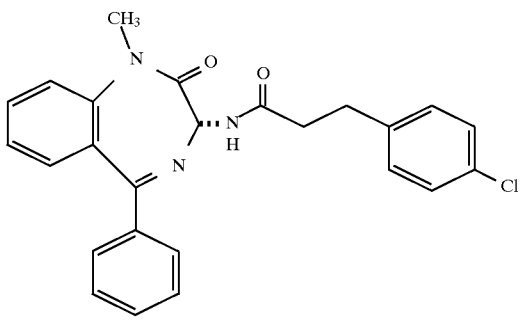

(+)-N-[(3R)-2,3-Dihydro-1-methyl-2-oxo-5-phenyl-1H-1,4-benzodiazepin-3-yl]-3-(4-chlorophenyl)propenamide
m.p. 203°–205° C., $[\alpha]_D$+99.2° (c=0.300, $CH_2Cl_2$). $^dH$ ($CDCl_3$) 7.62–7.16 (14H, m), 5.52 (1H, d, J 8.1 Hz), 3.47 (3H, s), 2.99 (2H, t, J 7.7 Hz), and 2.67 (2H, t, J 7.7 Hz). Anal. Calcd. for $C_{25}H_{22}ClN_3O_2$: C, 69.52; H, 5.13; N, 9.73. Found: C, 69.50; H, 5.15; N, 9.72%.

Example 19

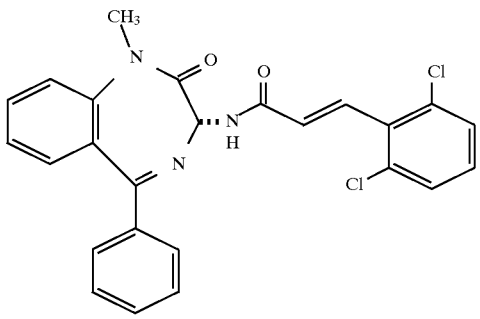

E-(+)-N-[(3R)-2,3-Dihydro-1-methyl-2-oxo-5-phenyl-1H-1,4-benzodiazepin-3-yl]-3-(2,6-dichlorophenyl)-2-propenamide
m.p. 121°–124° C., $[\alpha]_D$+69.0° (c=0.342, $CH_2Cl_2$). $^dH$ ($CDCl_3$) 7.79 (1H, d, J 16.1 Hz), 7.64–7.15 (13H, m), 6.78 (1H, d, J 15.8 Hz), 5.69 (1H, d, J 8.1 Hz), and 3.50 (3H, s). Anal. Calcd. for $C_{25}H_{19}Cl_2N_3O_2 \cdot 0.15PhCH_3$: C, 65.44; H, 4.23; N, 8.79. Found: C, 65.40; H, 4.38; N, 8.85%.

Example 20

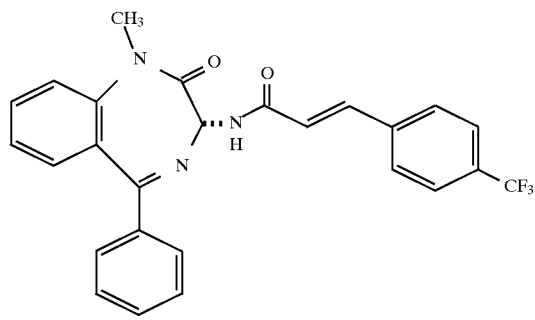

E-(+)-N-[(3R)-2,3-Dihydro-1-methyl-2-oxo-5-phenyl-1H-1,4-benzodiazepin-3-yl]-3-[4-(triflouromethyl)phenyl]-2-propenamide
m.p. 133°–137° C., $[\alpha]_D$+68.7° (c=0.115, $CH_2Cl_2$). $^dH$ ($CDCl_3$) 7.72–7.25 (15H, m), 6.71 (1H, d, J 15.6 Hz), 5.67 (1H, d, J 8.1 Hz), and 3.51 (3H, s). Anal. Calcd. for $C_{26}H_{20}F_3N_3O_2$: C, 67.38; H, 4.35; N, 9.07. Found: C, 67.38; H, 4.45; N, 8.95%.

Example 21

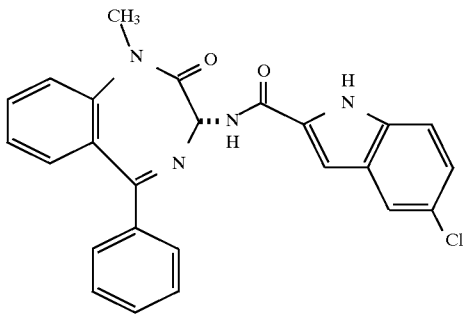

(+)-5-Chloro-N-[(3R)-2,3-dihydro-1-methyl-2-oxo-5-phenyl-1H-1,4-benzodiazepin-3-yl]indole-2-carboxamide
m.p. 160°–164° C., $[\alpha]_D$+103.8° (c=0.160, $CH_2Cl_2$). $^dH$ ($CDCl_3$) 9.71 (1H, br s), 8.13 (1H, d, J 7.8 Hz), 7.68–7.09

(13H, m), 5.75 (1H, d, J 7.8 Hz), and 3.53 (3H, s). Anal. Calcd. for C$_{25}$H$_{19}$ClN$_4$O$_2$.0.25H$_2$O.0.15PhCH$_3$: C, 67.84; H, 4.49; N, 12.15. Found: C, 67.80; H, 4.41; N, 12.07%.

Example 22

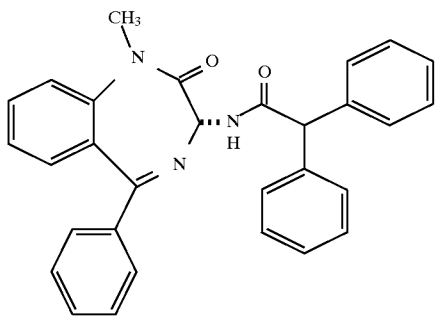

(+)-N-[(3R)-2,3-Dihydro-1-methyl-2-oxo-5-phenyl-1H-1,4-benzodiazepin-3-yl]-2,2-diphenylethanamide m.p. 200°–201° C., [α]$_D$+97.0° (c=0.168, CH$_2$Cl$_2$). $^d$H (CDCl$_3$) 7.60–7.22 (20H, m), 5.58 (1H, d, J 8.1 Hz), 5.08 (1H, s), and 3.44 (3H, s). Anal. Calcd. for C$_{30}$H$_{25}$N$_3$O$_2$.0.15PhCH$_3$: C, 78.79; H, 5.55; N, 8.88. Found: C, 78.81; H, 5.63; N, 9.07%.

Example 23

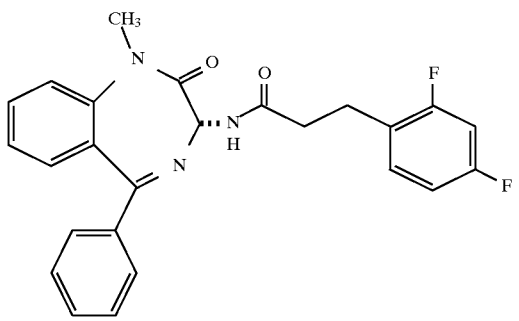

(+)-N-[(3R)-2,3-Dihydro-1-methyl-2-oxo-5-phenyl-1H-1,4-benzodiazepin-3-yl]-3-(2,4-difluorophenyl)propanamide m.p. 79°–81° C., [α]$_D$+92.9° (c=0.105, CH$_2$Cl$_2$). $^d$H (CDCl$_3$) 7.62–7.56 (3H, m), 7.50–7.19 (8H, m), 6.82–6.76 (2H, m), 5.52 (1H, d, J 8.1 Hz), 3.47 (3H, s), 3.01 (2H, t, J 7.6 Hz), and 2.69 (2H, m). Anal. Calcd. for C$_{25}$H$_{21}$F$_2$N$_3$O$_2$: C, 69.27; H, 4.88; N, 9.69. Found: C, 68.96; H, 4.99; N, 9.47%.

Example 24

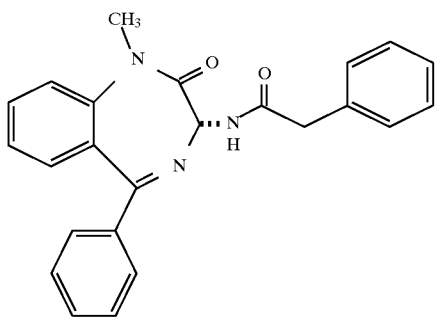

(+)-N-[(3R)-2,3-Dihydro-1-methyl-2-oxo-5-phenyl-1H-1,4-benzodiazepin-3-yl]-2-phenylethanamide m.p. 241°–242° C. (dec.), [α]$_D$+85.5° (c=0.159, CH$_2$Cl$_2$). $^d$H (CDCl$_3$) 7.59–7.55 (3H, m), 7.46–7.22 (12H, m), 5.51 (1H, d, J 8.1 Hz), 3.72 (2H, s), and 3.44 (3H, s). Anal. Calcd. for C$_{24}$H$_{21}$N$_3$O$_2$.0.55H$_2$O: C, 73.28; H, 5.66; N, 10.68. Found: C, 73.25; H, 5.38; N, 10.47%.

Example 25

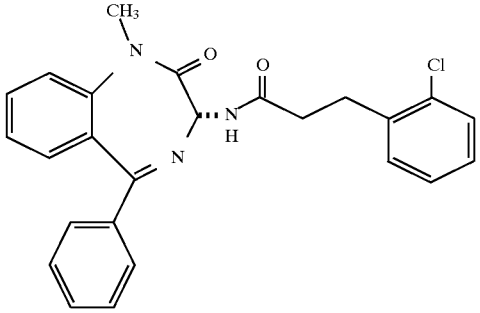

(+)-N-[(3R)-2,3-Dihydro-1-methyl-2-oxo-5-phenyl-1H-1,4-benzodiazepin-3-yl]-3-(2-chlorophenyl)propanamide m.p. 158.5°–159.5° C., [α]$_D$+95.8° (c=0.224, CH$_2$Cl$_2$). $^d$H (CDCl$_3$) 7.62–7.57 (3H, m), 7.47–7.16 (11H, m), 5.55 (1H, d, J 8.1 Hz), 3.47 (3H, s), 3.14 (2H, t, J 7.9 Hz), and 2.75–2.69 (2H, m). Anal. Calcd. for C$_{25}$H$_{22}$C$_1$N$_3$O$_2$.0.15H$_2$O: C, 69.09; H, 5.17; N, 9.67. Found: C, 69.05; H, 5.12; N, 9.63%.

Example 26

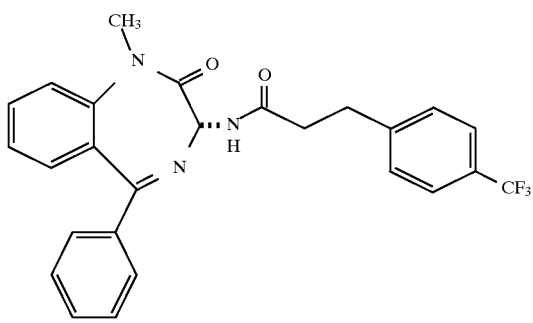

(+)-N-[(3R)-2,3-Dihydro-1-methyl-2-oxo-5-phenyl-1-4-benzodiazepin-3-yl]-3-[4-(trifluoromethyl)phenyl]propanamide m.p. 175°–176° C., [α]$_D$+86.5° (c=0.141, CH$_2$Cl$_2$). $^d$H (CDCl$_3$) 7.62–7.54 (5H, m), 7.47–7.22 (9H, m), 5.52 (1H, d, J 8.1 Hz), 3.47 (3H, m), 3.08 (2H, t, J 7.6 Hz), and 2.72 (2H, m). Anal. Calcd. for C$_{26}$H$_{22}$F$_3$N$_3$O$_2$.0.80H$_2$O: C, 65.08; H, 4.93; N, 8.76. Found: C, 65.03; H, 4.63; N, 8.72%.

Example 27

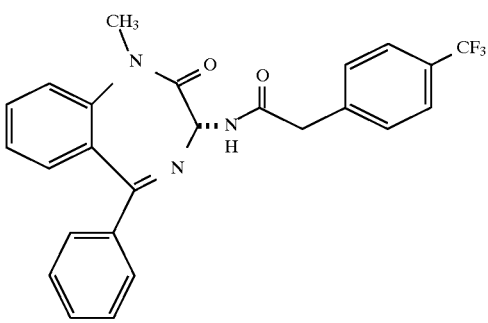

(+)-N-[(3R)-2,3-Dihydro-1-methyl-2-oxo-5-phenyl-1H-1,4-benzodiazepin-3-yl]-2-[4-(triflouromethyl)phenyl]ethanamide m.p. 224°–226° C., $[\alpha]_D$+68.0° (c=0.153, $CH_2Cl_2$). $^d$H (CDCl$_3$) 7.63–7.55 (4H, m), 7.51–7.33 (8H, m), 7.26–7.23 (2H, m), 5.51 (1H, d, J 8.1 Hz), 3.77 (2H, s), and 3.46 (3H, s). Anal. Calcd. for $C_{25}H_{20}F_3N_3O_2$: C, 66.51; H, 4.47; N, 9.31. Found: C, 66.46; H, 4.36; N, 9.10%.

Example 28

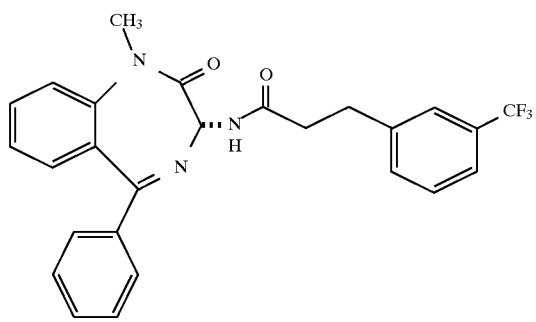

(+)-N-[(3R)-2,3-Dihydro-1-methyl-2-oxo-5-phenyl-1H-1,4-benzodiazepin-3-yl]-3-[3-(trifluoromethyl)phenyl]propanamide m.p. 135°–136° C., $[\alpha]_D$+78.8° (c=0.134., $CH_2Cl_2$). $^d$H (CDCl$_3$) 7.62–7.56 (3H, m), 7.49–7.22 (11H, m), 5.53 (1H, d, J 8.1 Hz), 3.47 (3H, s), 3.08 (2H, t, J 7.3 Hz), and 2.72 (2H, m). Anal. Calcd. for $C_{26}H_{22}F_3N_3O_2$: C, 67.09; H, 4.76; N, 9.03. Found: C, 67.03; H, 4.73; N, 9.13%.

Example 29

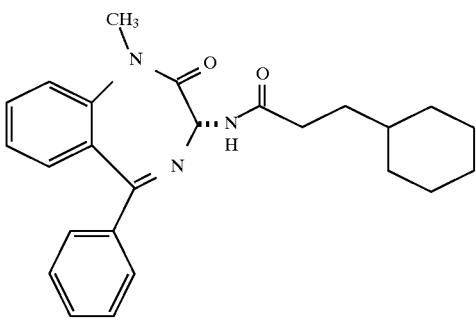

(+)-3-Cyclohexyl-N-[(3R)-2,3-dihydro-1-methyl-2-oxo-5-phenyl-1H-1,4-benzodiazepin-3-yl]propanamide m.p. 144.5°–145.5° C., $[\alpha]_D$+83.1° (c=0.116, $CH_2Cl_2$). $^d$H (CDCl$_3$) 7.62–7.56 (3H, m), 7.46–7.21 (7H, m), 5.55 (1H, d, J 8.3 Hz), 3.48 (3H, s), 2.41–2.36 (2H, m), 1.77–1.58 (7H, m), 1.31–1.16 (4H, m), and 0.98–0.90 (2H, m). Anal. Calcd. for $C_{25}H_{29}N_3O_2$: C, 74.41; H, 7.24; N, 10.41. Found: C, 74.46; H, 7.27; N, 10.58%.

Example 30

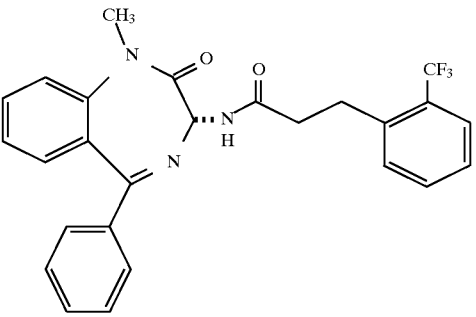

(+)-N-[(3R)-2,3-Dihydro-1-methyl-2-oxo-5-phenyl-1H-1,4-benzodiazepin-3-yl]-3-[2-(trifluoromethyl)phenyl]propanamide m.p. 110°–113° C., $[\alpha]_D$+79.2° (c=0.376, $CH_2Cl_2$). $^d$H (CDCl$_3$) 7.65–7.57 (4H, m), 7.50–7.22 (10H m), 5.55 (1H, d, J 8.0 Hz), 3.47 (3H, s), 3.20 (2H, t, J 7.9 Hz), and 2.70 (2H, dt, J 7.9, 3.3 Hz). Anal. Calcd. for $C_{26}H_{22}F_3N_3O_2$: C, 67.09; H, 4.76; N, 9.03. Found: C, 66.97; H, 4.76; N, 8.93%.

Example 31

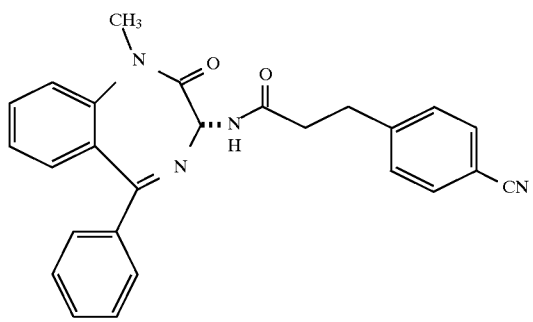

(+)-N-[(3R)-2,3-Dihydro-1-methyl-2-oxo-5-phenyl-1H-1,4-benzodiazepin-3-yl]-3-(4-cyanophenyl)propanamide m.p. 81°–85° C., $[\alpha]_D$+91.0° (c=0.111, $CH_2Cl_2$). $^d$H (CDCl$_3$) 7.64–7.55 (4H, m), 7.48–7.16 (10H m), 5.50 (1H, d, J 8.3 Hz), 3.47 (3H, s), 3.08 (2H, t, J 7.6 Hz), and 2.74–2.69 (2H, m). Anal. Calcd. for $C_{26}H_{22}N_4O_2 \cdot 0.60H_2O \cdot 0.50PhCH_3$: C, 73.93; H, 5.62; N, 11.69. Found: C, 73.98; H, 5.61; N, 11.71%.

Example 32

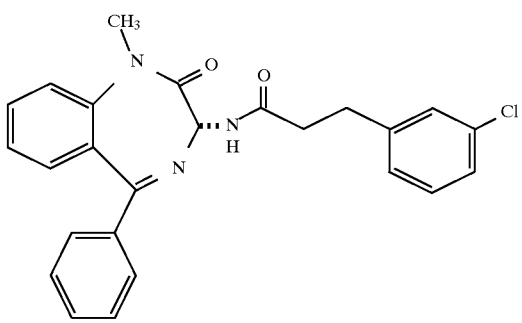

(+)-N-[(3R)-2,3-Dihydro-1-methyl-2-oxo-5-phenyl-1H-1,4-benzodiazepin-3-yl]-3-(3-chlorophenyl)propanamide m.p. 157°–159° C., $[\alpha]_D$+90.7° (c=0.134, CH$_2$Cl$_2$). $^d$H (CDCl$_3$) 7.62–7.57 (3H, m), 7.47–7.12 (11H, m), 5.53 (1H, d, J 8.1 Hz), 3.47 (3H, s), 3.00 (2H, t, J 7.3 Hz), and 2.71–2.66 (2H, m). Anal. Calcd. for C$_{25}$H$_{22}$ClN$_3$O$_2$.0.55H$_2$O: C, 67.96; H, 5.27; N, 9.51. Found: C, 67.99; H, 5.18; N, 9.26%.

Example 33

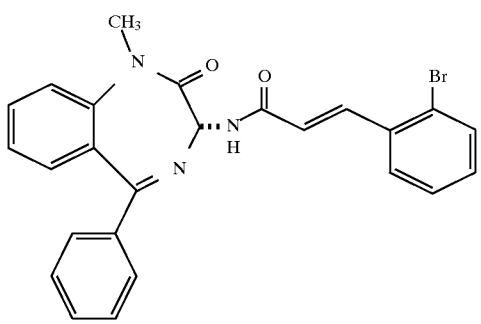

E-(+)-N-[(3R)-2,3-Dihydro-1-methyl-2-oxo-5-phenyl-1H-1,4-benzodiazepin-3-yl]-3-(2-bromophenyl)-2-propenamide m.p. 113°–116° C., $[\alpha]_D$+44.2° (c=0.113, CH$_2$Cl$_2$). $^d$H (CDCl$_3$) 8.03 (1H, d, J 15.6 Hz), 7.64–7.16 (14H, m), 6.57 (1H, d, J 15.6 Hz), 5.68 (1H, d, J 8.1 Hz), and 3.50 (3H, s). Anal. Calcd. for C$_{25}$H$_{20}$BrN$_3$O$_2$.0.60H$_2$O.0.30PhCH$_3$: C, 63.48; H, 4.58; N, 8.19. Found: C, 63.49; H, 4.38; N, 8.19%.

Example 34

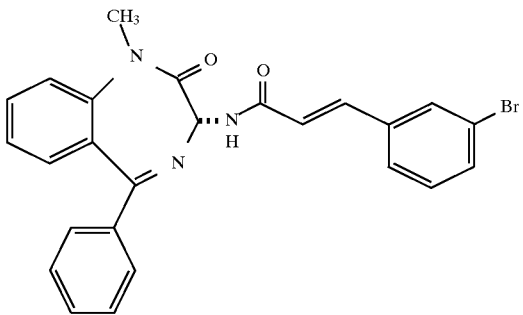

E-(+)-N-[(3R)-2,3-Dihydro-1-methyl-2-oxo-5-phenyl-1H-1,4-benzodiazepin-3-yl]-3-(3-bromophenyl)-2-propenamide m.p. 221°–223° C., $[\alpha]_D$+65.5° (c=0.206, CH$_2$Cl$_2$). $^d$H (CDCl$_3$) 7.69 (1H, br s), 7.64–7.57 (4H, m), 7.51–7.37 (6H, m), 7.29–7.19 (4H, m), 6.62 (1H, d, J 15.6 Hz), 5.66 (1H, d, J 8.1 Hz), and 3.50 (3H, s). Anal. Calcd. for C$_{25}$H$_{20}$BrN$_3$O$_2$.0.35H$_2$O.0.20PhCH$_3$: C, 63.54; H, 4.46; N, 8.42. Found: C, 63.50; H, 4.39; N, 8.42%.

Example 35

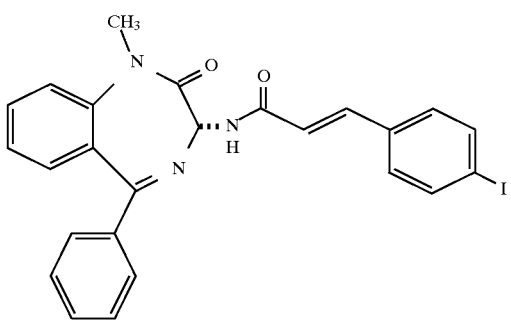

E-(+)-N-[(3R)-2,3-Dihydro-1-methyl-2-oxo-5-phenyl-1H-1,4-benzodiazepin-3-yl]-3-(4-iodophenyl)-2-propenamide m.p. 137°–140° C., $[\alpha]_D$+67.9° (c=0.268, CH$_2$Cl$_2$). $^d$H (CDCl$_3$) 7.75–7.72 (2H, m), 7.64–7.36 (8H, m), 7.29–7.16 (5H, m), 6.63 (1H, d, J 15.6 Hz), 5.66 (1H, d, J 8.1 Hz), and 3.50 (3H, m). Anal. Calcd. for C$_{25}$H$_{20}$IN$_3$O$_2$.0.30PhCH$_3$: C, 59.29; H, 4.06; N, 7.65. Found: C, 59.29; H, 3.90; N, 7.40%.

Example 36

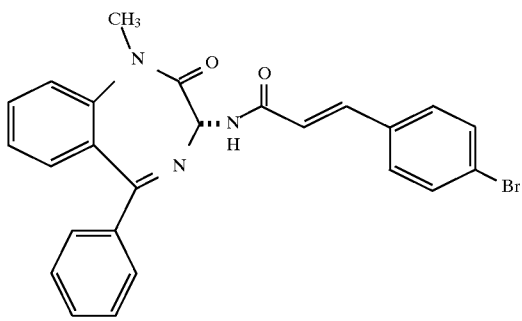

E-(+)-N-[(3R)-2,3-Dihydro-1-methyl-2-oxo-5-phenyl-1H-1,4-benzodiazepin-3-yl]-3-(4-bromophenyl)-2-propenamide m.p. 121°–124° C., $[\alpha]_D$+75.6° (c=0.201, CH$_2$Cl$_2$). $^d$H (CDCl$_3$) 7.64–7.57 (3H, m), 7.55–7.35 (11H, m), 7.28–7.24 (1H, m), 6.62 (1H, d, J 15.6 Hz), 5.66 (1H, d, J 8.1 Hz), and 3.50 (3H, s). Anal. Calcd. for C$_{25}$H$_{20}$BrN$_3$O$_2$: C, 63.30; H, 4.25; N, 8.86. Found: C, 63.50; H, 4.20; N, 8.78%.

Example 37

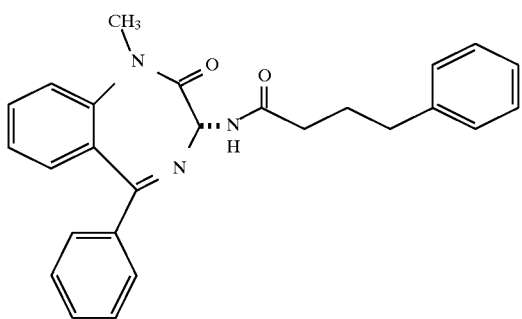

(+)-N-[(3R)-2,3-Dihydro-1-methyl-2-oxo-5-phenyl-1H-1,4-benzodiazepin-3-yl]-4-phenylbutanamide m.p. 65°–74° C., [α]$_D$+77.4° (c=0.155, CH$_2$Cl$_2$). $^d$H (CDCl$_3$) 7.62–7.56 (3H, m), 7.46–7.19 (12H, m), 5.55 (1H, d, J 8.1 Hz), 3.47 (3H, s), 2.71 (2H, t, J 7.6 Hz), 2.42–2.37 (2H, m), and 2.09–2.01 (2H, m). Anal. Calcd. for C$_{26}$H$_{25}$N$_3$O$_2$.0.30H$_2$O: C, 74.91; H, 6.19; N, 10.08. Found: C, 74.93; H, 6.05; N, 10.07%.

Example 38

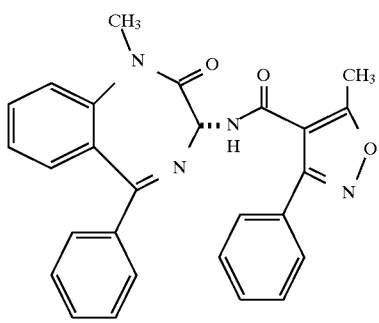

(+)-N-[(3R)-2,3-Dihydro-1-methyl-2-oxo-5-phenyl-1H-1,4-benzodiazepin-3-yl]-5-methyl-3-phenylisoxazole-4-carboxamide m.p. 123°–126° C., [α]$_D$+122.0° (c=0.199, CH$_2$Cl$_2$). $^d$H (CDCl$_3$) 7.79–7.76 (2H, m), 7.62–7.32 (11H, m), 7.26–7.21 (2H, m), 5.61 (1H, d, J 7.9 Hz), 3.42 (3H, s), and 2.76 (3H, s). Anal. Calcd. for C$_{27}$H$_{22}$N$_4$O$_3$.0.40H$_2$O: C, 70.85; H, 5.02; N, 12.24. Found: C, 70.84; H, 4.91; N, 11.92%.

Example 39

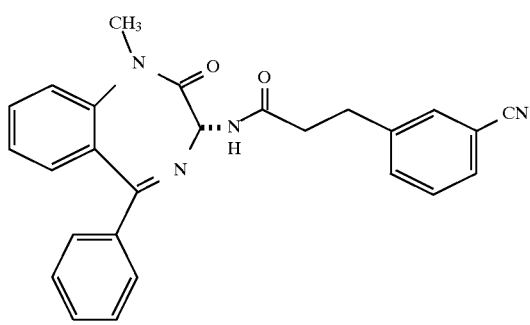

(+)-N-[(3R)-2,3-Dihydro-1-methyl-2-oxo-5-phenyl-1H-1,4-benzodiazepin-3-yl]-3-(3-cyanophenyl)propanamide m.p. 110°–112° C., [α]$_D$+84.2° (c=0.202, CH$_2$Cl$_2$). $^d$H (CDCl$_3$) 7.63–7.22 (14H, m), 5.51 (1H, d, J 8.1 Hz), 3.47 (3H, s), 3.06 (2H, t, J 7.8 Hz), and 2.74–2.68 (2H, m). Anal. Calcd. for C$_{26}$H$_{22}$N$_4$O$_2$.0.50H$_2$O: C, 72.37; H, 5.37; N, 12.98. Found: C, 72.52; H, 5.12; N, 12.59%.

Example 40

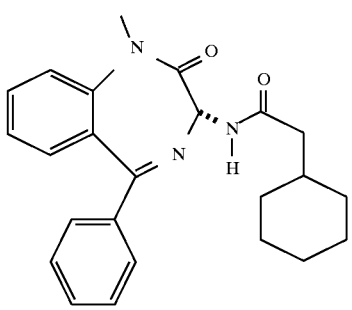

(+)-N-[(3R)-2,3-Dihydro-1-methyl-2-oxo-5-phenyl-1H-1,4-benzodiazepin-3-yl]cyclohexanethanamide m.p. 144°–146° C., [α]$_D$+72.1° (c=1.000, MeOH). Anal. Calcd. for C$_{24}$H$_{27}$N$_3$O$_2$.0.20H$_2$O: C, 73.33; H, 7.03; N, 10.69. Found: C, 73.27; H, 7.02; N, 10.76%.

Example 41

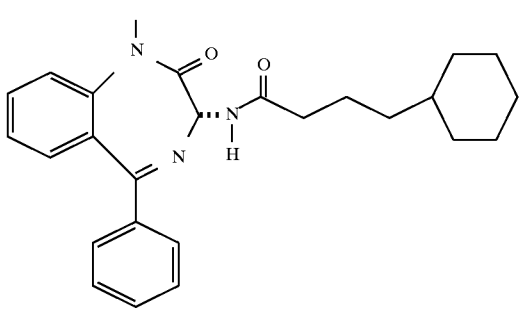

(+)-4-Cyclohexyl-N-[(3R)-2,3-dihydro-1-methyl-2-oxo-5-phenyl-1H-1,4-benzodiazepin-3-yl]butanamide

[α]$_D$+57.7° (c=0.440, MeOH). Anal. Calcd. for C$_{26}$H$_{31}$N$_3$O$_2$: C, 74.79; H, 7.48; N, 10.06. Found: C, 74.8;0 H, 7.78; N, 10.05%.

Example 42

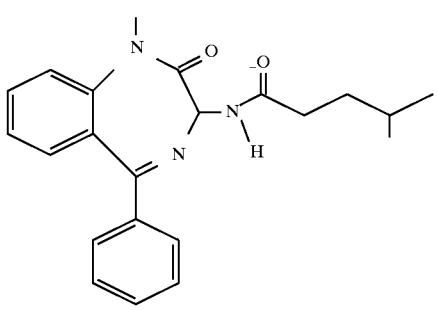

(+)-N-[(3R)-2,3-Dihydro-1-methyl-2-oxo-5-phenyl-1H-1,4-benzodiazepin-3-yl]-4-methylpentanamide m.p. 123°–125° C., [α]$_D$+66.8° (c=0.500, MeOH). Anal. Calcd. for C$_{22}$H$_{25}$N$_3$O$_2$.0.45H$_2$O: C, 71.12; H, 7.03; N, 11.31. Found: C, 71.08; H, 6.8 1; N, 11.42%.

Example 43

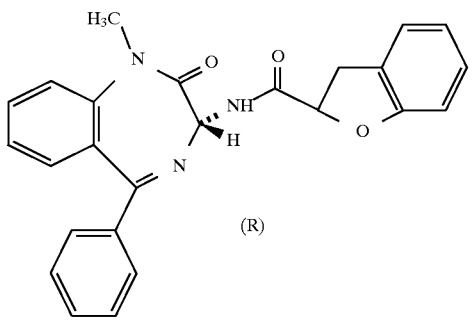

(+)-N-[(3R)-2,3-Dihydro-1-methyl-2-oxo-5-phenyl-1H-1,4-benzodiazepin-3-yl]-2,3-dihydrobenzofuran-2-carboxamide Diisopropylethylamine (0.3 mL, 223 mg, 1.72 mmol) was added to a stirred, cooled (0° C.) solution of 3 (R)-amino-1,3-dihydro-1-methyl-5-phenyl-2H-1,4-benzodiazepin-2-one (*J. Org. Chem.* 1987, 52, 3232–3239) (400 mg, 1.5 mmol), 2,3-dihydrobenzofuran-2-carboxylic acid (274 mg, 1.7 mmol), 1-(3-dimethylaminopropyl)-3-ethylcarbodiimide hydrochloride (583 mg, 3.0 mmol), and 1-hydroxybenzotriazole (479 mg, 3.1 mmol) in DMF (4.5 mL). The mixture was stirred at room temperature for 18 h., poured into aqueous hydrochloric acid (3M, 12 mL) and extracted with ethyl acetate (3×20 mL). The combined organic fractions were washed with saturated aqueous sodium hydrogen carbonate (20 mL) and brine (20 mL), dried (MgSO$_4$) and evaporated under reduced pressure. The residue was crystallized from 2-chloro-2-methylpropane/hexane to give (+)-N-[(3R)-2,3-dihydro-1-methyl-2-oxo-5-phenyl-1H-1,4-benzodiazepin-3-yl]-2,3-dihydrobenzofuran-2-carboxamide as a colorless solid (156 mg, 25%), m.p. 141°–180° C., [α]$_D$+127.1° (c=0.425, CHCl$_3$). $^d$H (CDCl$_3$) (3:1 Mixture of diastereoisomers) 8.44 (1H, m), 7.65–6.91 (13H, m), 5.52 (1H, m), 5.28 (1H, m), and 3.70–3.40 (5H, m). Anal. Calcd. for C$_{25}$H$_{21}$N$_3$O$_3$.0.25 Hexane C, 73.50; H, 5.70; N, 9.71. Found: C, 74.12; H, 5.57; N, 9.71%.

Example 44

(+)-N-[(3R)-2,3-dihydro-1-methyl-2-oxo-5-phenyl-1H-1,4-benzodiazepin-3-yl]-1'-(1,1-dimethylethoxycarbonyl)spiro(cyclohexan-4,4'-piperidine)-1-carboxamide

Step A:

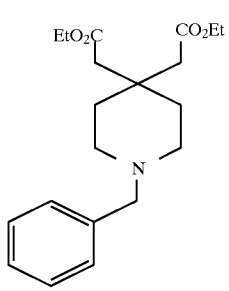

Diethyl 1-benzylpiperidine-4,4-diacetate

Ethanol (120 mL) was cooled in ice and ammonia bubbled through to give a saturated solution. 1-Benzyl-4-piperidone (40.0 g, 211 mmol) and ethyl cyanoacetate (47.8 g, 423 mmol) were added, the reaction vessel stoppered and stored at 0° C. overnight. The solid was collected, washed with ethanol and ether and dried in vacuo to give a yellow solid (68.86 g). The solid (58.86 g) was dissolved in a mixture of sulfuric acid (70 mL, 98%) and water (60 mL) and heated under reflux for three days the mixture cooled and most of the water evaporated. The residue was azeotroped with ethanol (4×750 mL), further ethanol (500 mL) added and the mixture heated under reflux for 20 h, cooled in ice and sodium carbonate (100 g) added slowly with vigorous stirring. The ethanol was evaporated under reduced pressure, water (800 mL) added and the mixture extracted with methylene chloride (3×400 mL). The combined organic extracts were dried (Na$_2$SO$_4$) and the solvent evaporated to give diethyl 1-benzylpiperidine-4,4-diacetate (37.51 g). A small portion of this was purified by flash column chromatography.

NMR (300 MHz, CDCl$_3$) d: 7.2–7.4 (m, 5H), 4.11 (q, J=7.3 Hz, 4H), 3.50 (s, 2H), 2.56 (s, 4H), 2.4 (m, 4H), 1.7 (m, 4H), 1.24 (t, J=7.3 Hz, 6H).

Step B:

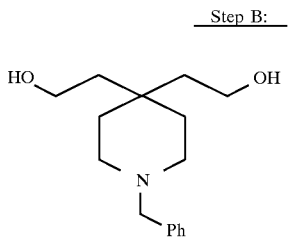

1-Benzylpiperidine-4 4-diethanol

A solution of the diester (12.2 g, 35 mmol) in ether (25 mL) was added to a cooled (−30° C.) and stirred suspension of LiAlH$_4$ (2.1 g, 55 mmol) in ether (400 mL), under argon. THF (60 mL) was added and the reaction mixture allowed to warm to room temperature. After recooling to 0° C., water (2.2 mL), 1M NaOH (4.4 mL) and water (5 mL) were added, the reaction mixture stirred vigorously for 30 min and the solid filtered off, washing well with ether. The combined filtrates were evaporated to afford a white solid which was tritutrated with ether to give 8 g of 1-benzylpiperidine-4,4-diethanol.

m.p. 75°–78° C. NMR (300 MHz, CDCl$_3$) d: 7.2–7.4 (m, 5H), 3.7 (t, J=6.8 Hz, 4H), 3.52 (s, 2H), 2.7 (brs, 2H), 2.43 (m, 4H), 1.66 (t, J=6.8 Hz, 4H), 1.5 (m, 4H).

Step C:

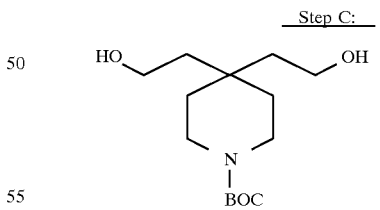

1-t-Butoxycarbonylpiperidine-4,4-diethanol

The benzylamine (2.07 g, 7.9 mmol) was dissolved in methanol (60 mL), BOC$_2$O (1.72 g, 7.9 mmol) added and the mixture hydrogenated at 50 psi over 10% palladium hydroxide on charcoal (200 mg) for 18 hours. The reaction mixture was filtered through celite, washed with methanol and the filtrate evaporated to give 1-t-butoxycarbonylpiperidine-4,4-diethanol (2.0 g).

NMR (300 MHz, CDCl$_3$) d: 3.7 (m, 4H), d 3.3 (m, 6H), 1.65 (t, J=6.8 Hz, 4H), 1.41 (s, 9H).

Step D:

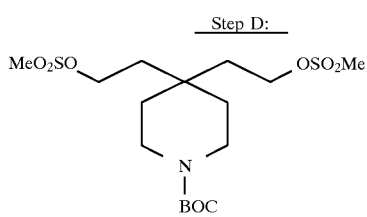

1-t-Butoxycarbonylpiperidine-4,4-diethanol, bis(methanesulfonate)

The diol (2.41 g, 8.9 mmol) was dissolved in dichloromethene (50 mL), the solution cooled to −20° C. under argon before addition of triethylamine (3.7 mL, 26 mmol) and methanesulfonyl chloride (1.6 mL, 20 mmol). After 30 min., the reaction mixture was poured into ice cold 10% citric acid and extracted with ether (×3). The combined extracts were washed with water, saturated $NaHCO_3$ and brine, dried ($MgSO_4$) and the solvent evaporated to afford 1-t-butoxycarbonylpiperidine-4,4-diethanol, bis(methanesulfonate) (3.2 g). NMR (300 MHz, $CDCl_3$) d: 4.32 (t, J=7.1 Hz, 4H), 3.4 (m, 4H), 3.04 (s, 6H), 1.89 (t, J=7.1 Hz, 4H).

Step E:

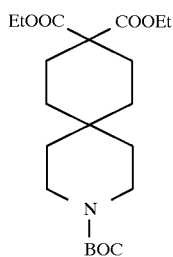

Diethyl 3-t-butyloxycarbonyl-3-azaspiro[5.5]undecane-9,9-dicarboxylate

To a slurry of 60% NaH (2.04 g, 0.51 mole) in toluene (160 mL), under argon, was slowly added diethyl malonate (3.72 mL, 24.3 mmol). The mixture was cooled to 0° C. and the bis-mesylate 1 (7.0 g, 16.3 mmol) added as a solid and the mixture heated to reflux for 18 hours. The reaction was quenched into 10% citric acid (100 mL) and the product extracted with $CH_2Cl_2$(2×150 mL). The extracts were dried ($Na_2SO_4$), concentrated to an oil, and chromatographed on silica to give 3.83 g (60%) of diethyl 3-t-butyloxycarbonyl-3-azaspiro-[5.5]undecane-9,9-dicarboxylate. $^1H$ NMR ($CDCl_3$) d: 1.22 (t, 6H), 1.4 (s, 9H), 2.0 (m, 4H), 3.35 (m, 4H), 4.2 (q, 4H).

Step F

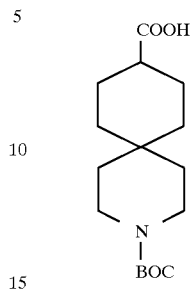

3-t-Butyloxycarbonyl-3-azaspiro[5.5]undecane-9-carboxylic acid

To a solution of the diester 2 (3.69 g, 0.0093 m) in THF (50 mL) was added 1N LiOH (47 mL). The reaction was stirred for 3 days at 25° C., diluted with water (50 mL) and pH adjusted to 2.2 with $KHSO_4$. The product was extracted into ethyl acetate (2×75 mL), dried ($Na_2SO_4$), and concentrated to a foam (3.5 g). The solid was melted in a flask at 140° C. for 2 hours, cooled and the oil dissolved in THF (15 mL), 1N LiOH (10 mL) added and mixture stirred overnight at 30° C. The reaction was concentrated to remove THF, diluted with water (20 mL) and washed with diethyl ether (10 mL). The pH was adjusted to 2.5 with $KHSO_4$ and product extracted (3×50 mL) with ethyl acetate. The extracts were dried ($Na_2SO_4$), filtered and concentrated to yield 3-t-butyloxycarbonyl-3-azaspiro[5.5]undecane-9-carboxylic acid as a foam (2.48 g, 90%). $^1H$ NMR ($CDCl_3$, partial) d: 1.45 (s, 9H), 3.4 (m, 4H).

Employing the procedure substantially as described in Example 43 but substituting an appropriate acid for the 2,3-dihydrobenzofuran-2-carboxylic acid, the following compounds were prepared:

Step G:

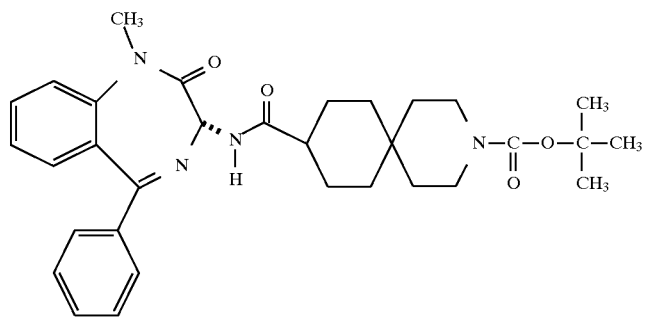

(+)-N-[(3R)-2,3-Dihydro-1-methyl-2-oxo-5-phenyl-1H-1,4-benzodiazepin-3-yl]-1'-(1,1-dimethylethoxycarbonyl)spiro(cyclohexan-4,4'-piperidine)-1-carboxamide m.p. 135°–138° C., $[\alpha]_D$+58.8° (C=0.925, $CHCl_3$). $^1H$ ($CDCl_3$) 7.61–7.23 (10H, m), 5.54 (1H, d, J 9.0 Hz), 3.47 (3H, s), 3.37 (4H, m), 2.28 (1H, m), and 1.81–1.18 (21H, s). Anal. Calcd. for $C_{32}H_{40}N_4O_4$: C, 70.56; H, 7.40; N, 10.29. Found: C, 70.21; H, 7.40; N, 10.16%.

Example 45

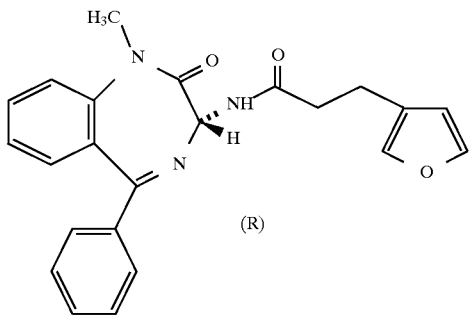

(+)-N-[(3R)-2,3-Dihydro-1-methyl-2-oxo-5-phenyl-1H-1,4-benzodiazepin-3-yl]-3-(furan-2-yl)propanamide m.p. 115°–118° C., $[\alpha]_D$+65.8° (c=0.800, CHCl$_3$). $^d$H (CDCl$_3$) 7.62–7.26 (11H, m), 6.28 (1H, dd, J 3.2, 2.0 Hz), 6.08 (1H, dd, J 3.2, 0.7 Hz), 5.58 (1H, d, J 8.1 Hz), 3.48 (3H, s), 3.04 (2H, t, J 7.6 Hz), and 2.75 (2H, m). Anal. Calcd. for C$_{23}$H$_{21}$N$_3$O$_3$.0.3Hexane: C, 72.07; H, 6.15; N, 10.17. Found: C, 71.78; H, 6.30; N, 9.77%.

Example 46

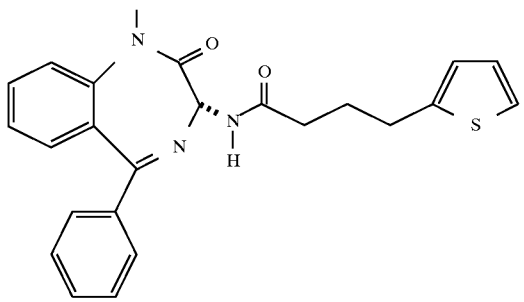

(+)-N-[(3R)-2,3-Dihydro-1-methyl-2-oxo-5-phenyl-1H-1,4-benzodiazepin-3-yl]-4-(2-thienyl)butanamide m.p. 170°–180° C., $[\alpha]_D$+63.5° (c=1.000, MeOH). Anal. Calcd. for C$_{24}$H$_{23}$N$_3$O$_2$S.0.95H$_2$O: C, 66.32; H, 5.77; N, 9.67. Found: C, 66.32; H, 5.34; N, 9.40%.

Example 47

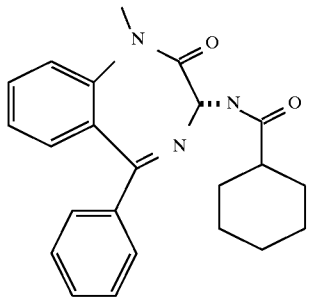

(+)-N-[(3R)-2,3-Dihydro-1-methyl-2-oxo-5-phenyl-1H-1,4-benzodiazepin-3-yl]cyclohexylcarboxamide m.p. 213°–214° C., $[\alpha]_D$+62.4° (c=1.000, MeOH). Anal. Calcd. for C$_{23}$H$_{24}$N$_3$O$_2$: C, 73.77; H, 6.46; N, 11.22. Found: C, 73.86; H, 6.81; N, 11.15%.

Example 48

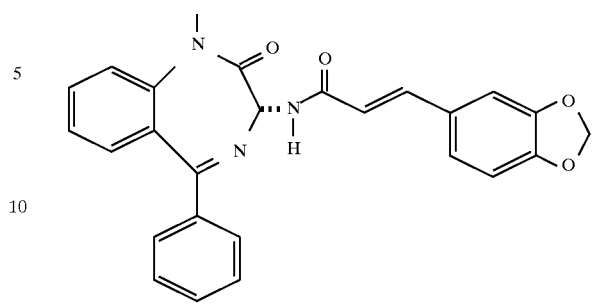

(E)-(+)-N-[(3R)-2,3-Dihydro-1-methyl-2-oxo-5-phenyl-1H-1,4-benzodiazepin-3-yl]-3-(3,4-methylenedioxyphenyl)-2-propenamide m.p. 143°–145° C., $[\alpha]_D$+62.3° (c=0.960, MeOH). Anal. Calcd. for C$_{25}$H$_{21}$N$_3$O$_4$.0.10H$_2$O.0.20 Et$_2$O: C, 69.78; H, 5.27; N, 9.46. Found: C, 69.78; H, 4.98; N, 9.28%.

Example 49

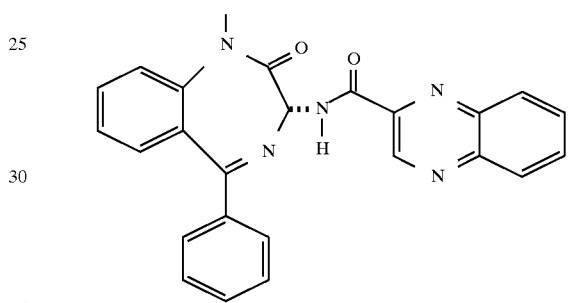

(+)-N-[(3R)-2,3-dihydro-1-methyl-2-oxo-5-phenyl-1H-1,4-benzodiazepin-3-yl]-2-quinoxalinecarboxamide $[\alpha]_D$+85.8° (c=0.360, MeOH). Anal. Calcd. for C$_{25}$H$_{19}$N$_5$O$_2$: C, 69.96; H, 4.90; N, 15.33. Found: C, 69.95; H, 4.72; N, 15.25%.

Example 50

(+)-N-[(3R)-2,3-Dihydro-2-methyl-2-oxo-5-phenyl-1H-1,4-benzodiazepin-3-yl]-2-(phenylamino)acetamide Step A:

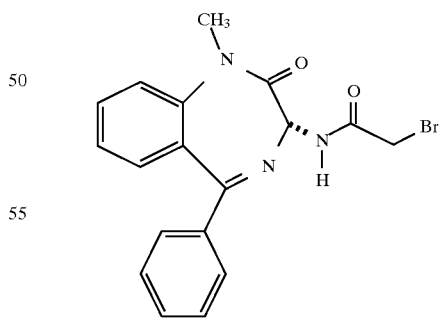

N-[(3R)-2,3-Dihydro-1-methyl-2-oxo-5-phenyl-1H-1,4-benzodiazepin-3-yl]-2-bromoacetamide Bromoacetyl bromide (165 mL, 383 mg, 1.9 mmol) was added to an ice cooled solution of 3 (R)-amino-1,3-dihydro-1-methyl-5-phenyl-2H-1,4-benzodiazepin-2-one (*J. Org. Chem.* 1987, 52, 3232–3239) (500 mg, 1.88 mmol) and triethylamine (264 mL, 192 mg, 1.9 mmol) in methylene chloride (10 mL) and the mixture was stirred at room temperature for 1 h. The mixture was washed with water (3×10 mL), dried (MgSO$_4$) and the solvent was evaporated under reduced pressure to give N-[(3R)-2,3-dihydro-1-methyl-2-oxo-5-phenyl-1H-1,4-benzodiazepin-3-yl]-2-bromoacetamide as a colorless foam (760 mg, 100%). $^d$H (CDCl$_3$) 8.24 (1H, d, J 7.8 Hz), 7.64–7.24 (9H, m), 5.48 (1H, d, J 7.8 Hz), 4.00 (2H, m), and 3.50 (3H, s).

Step B:

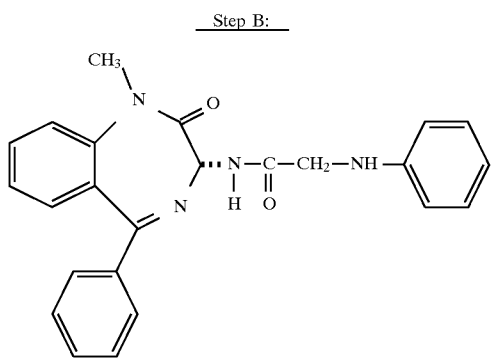

(+)-N-[(3R)-2,3-Dihydro-1-methyl-2-oxo-5-phenyl-1H-1,4-benzodiazepin-3-yl]-2-(phenylamino)acetamide Aniline (297 mL, 304 mg, 3.26 mmol) was added to a solution of N-[(3R)-2,3-dihydro-1-methyl-2-oxo-5-phenyl-1H-1,4-benzodiazepin-3-yl]-2-bromoacetamide (600 mg, 1.55 mmol) in ethanol (25 mL) and the mixture was heated under reflux for 24 h. The mixture was cooled and the solid was collected and recrystallized from ethanol (20 mL) to give (+)-N-[(3R)-2,3-dihydro-1-methyl-2-oxo-5-phenyl-1H-1,4-benzodiazepin-3-yl]-2-(phenylamino)acetamide as a colorless solid (500 mg, 81%), m.p. 245°–246° C., [α]$_D$+119° (C=0.850, CHCl$_3$). $^d$H (CDCl$_3$) 8.26 (1H, d, J 8.3 Hz), 7.63–7.20 (12H, m), 6.81 (1H, t, J 7.3 Hz), 6.72 (2H, d, J 7.6 Hz), 5.56 (1H, d, J 8.3 Hz), 3.95 (2H, d, J 1.5 Hz), and 3,45 (3H, s). Anal. Calcd. for C$_{24}$H$_{22}$N$_4$O$_2$: C, 72.34; H, 5.57; N, 14.06. Found: C, 72.37; H, 5.59; N, 14.32%.

Employing the procedure substantially as described above, but substituting 2-chloroaniline or 4-(trifluoromethyl)aniline for the aniline, the following compounds were prepared:

Example 51

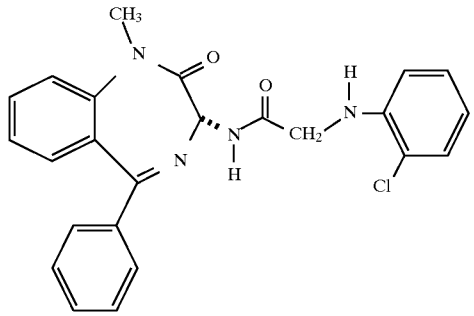

(+)-N-[(3R)-2,3-Dihydro-1-methyl-2-oxo-5-phenyl-1H-1,4-benzodiazepin-3-yl]-2-(2-chlorophenylamino)acetamide m.p. 222°–224° C., [α]$_D$+111° (c=0.973, CHCl$_3$). $^d$H (CDCl$_3$) 8.15 (1H, d, J 8.3 Hz), 7.60–7.16 (12H, m), 6.71 (2H, m), 5.57 (1H, d, J 8.3 Hz), 4.01 (2H, d, J 2.7 Hz), and 3,45 (3H, s). Anal. Calcd. for C$_{24}$H$_{21}$ClN$_4$O$_2$: C, 66.59; H, 4.89; N, 12.94. Found: C, 66.40; H, 4.94; N, 12.92%.

Example 52

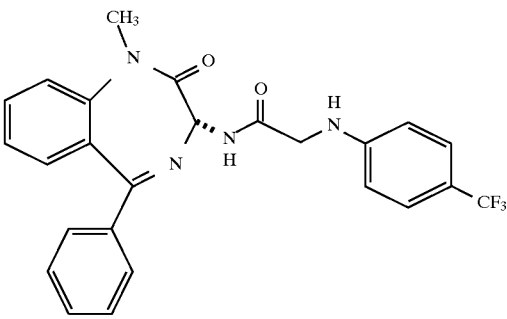

(+)-N-[(3R)-2,3-Dihydro-1-methyl-2-oxo-5-phenyl-1H-1,4-benzodiazepin-3-yl]-2-[4-(trifluoromethyl)phenylamino]acetamide m.p. 218°–219° C., [α]$_D$+91.9° (c=0.419, CHCl$_3$). $^d$H (CDCl$_3$) 8.13 (1H, d, J 9.0 Hz), 7.70–7.25 (12H, m), 6.72 (2H, d, J 8.7 Hz), 5.60 (1H, d, J 9.0 Hz), 4.05 (2H, m), and 3.50 (3H, s). Anal. Calcd. for C$_{25}$H$_{21}$F$_3$N$_4$O$_2$.0.7H$_2$O: C, 62.68; H, 4.71; N, 11.69. Found: C, 62.47; H, 4.32; N, 11.44%.

Example 53

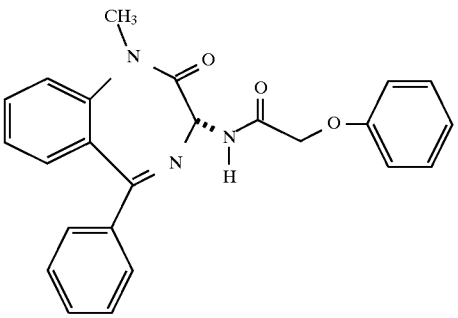

(+)-N-[(3R)-2,3-Dihydro-1-methyl-2-oxo-5-phenyl-1H-1,4-benzodiazepin-3-yl]-2-(phenoxy)acetamide Phenol (104 mg, 1.11 mmol) was added to a suspension of sodium hydride (60% dispersion in mineral oil, 44 mg, 1.1 mmol) in toluene (10 mL). When hydrogen evolution had stopped, N-[(3R)-2,3-dihydro-1-methyl-2-oxo-5-phenyl-1H-1,4-benzodiazepin-3-yl]-2-bromoacetamide (400 mg, 1.04 mmol) was added and the mixture was stirred at room temperature for 18 h. The mixture was washed with water (3×15 mL), dried (MgSO$_4$) and the solvent was evaporated under reduced pressure. The residue was triturated with 2-propanol and the solid was collected and recrystallized from 2-propanol (5 mL) to give (+)-N-[(3R)-2,3-dihydro-1-methyl-2-oxo-5-phenyl-1H-1,4-benzodiazepin-3-yl]-2-(phenoxy)acetamide as a colorless solid (112 mg, 27%), m.p. 126°–128° C., [α]$_D$+81.6 (C=0.692, CHCl$_3$). $^d$H (CDCl$_3$) 8.49 (1H, d, J 8.2 Hz), 7.64–7.01 (14H, m), 5.61 (1H, d, J 8.2 Hz), 4.65 (1H, d, J 14.6 Hz), 4.58 (1H, d, J 14.6 Hz), and 3.50 (3H, s). Anal. Calcd. for C$_{24}$H$_{21}$N$_3$O$_3$: C, 72.17; H, 5.30; N, 10.52. Found: C, 71.84; H, 5.25; N, 10.41%.

Employing the procedure substantially as described above, but substituting 2,4-dichlorophenol, thiophenol or 2,4-dichlorothiophenol for the phenol, the following compounds were prepared:

Example 54

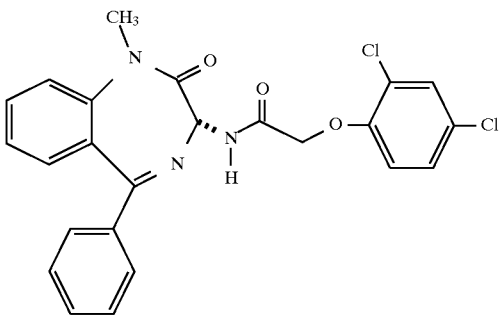

(+)-N-[(3R)-2,3-Dihydro-1-methyl-2-oxo-5-phenyl-1H-1,4-benzodiazepin-3-yl]-2-(2,4-dichlorophenoxy)acetamide m.p. 206° C., $[\alpha]_D$+31.1° (c=0.289, CHCl$_3$). $^d$H (CDCl$_3$) 8.75 (1H, d, J 9.0 Hz), 7.65–7.20 (11H, m), 6.90 (1H, d, J 8.7 Hz), 5.60 (1H, d, J 9.0 Hz), 4.65 (2H, m), and 3.50 (3H, s). Anal. Calcd. for C$_{24}$H$_{19}$Cl$_2$N$_3$O$_3$.0.3H$_2$O: C, 60.85; H, 4.17; N, 8.87. Found: C, 60.80; H, 4.04; N, 8.87%.

Example 55

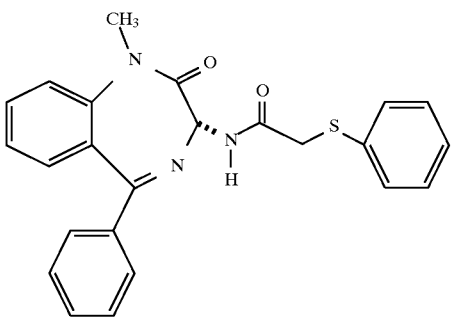

(+)-N-[(3R)-2,3-Dihydro-1-methyl-2-oxo-5-phenyl-1H-1,4-benzodiazepin-3-yl]-2-(phenylthio)acetamide $[\alpha]_D$+104.9° (c=0.316, CHCl$_3$). $^d$H (CDCl$_3$) 8.50 (1H, d, J 9.0 Hz), 7.60–7.20 (14H, m), 5.50 (1H, d, J 9.0 Hz), 3.75 (2H, m), and 3,45 (3H, s). Anal. Calcd. for C$_{24}$H$_{21}$N$_3$O$_2$ S: C, 69.37; H, 5.10; N, 10.11. Found: C, 68.98; H, 5.06; N, 9.76%.

Example 56

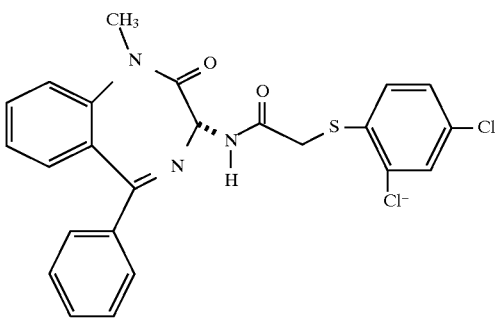

(+)-N-[(3R)-2,3-Dihydro-1-methyl-2-oxo-5-phenyl-1H-1,4-benzodiazepin-3-yl]-2-(2,4-dichlorophenylthio)acetamide $[\alpha]_D$+97.4° (c=0.286, CHCl$_3$). $^d$H (CDCl$_3$) 8.35 (1H, d, J 9.0 Hz), 7.70–7.20 (12H, m), 5.50 (1H, d, J 9.0 Hz), 3.70 (2H, m), and 3.50 (3H, s). Anal. Calcd. for C$_{24}$H$_{19}$Cl$_2$N$_3$O$_2$S: C, 59.51; H, 3.95; N, 8.67. Found: C, 59.32; H, 3.95; N, 8.65%.

Example 57

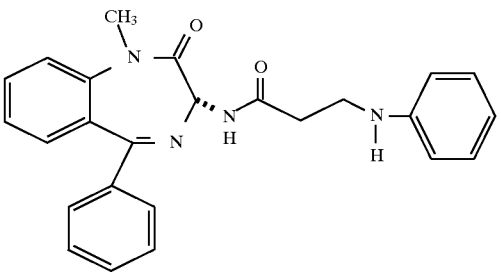

(+)-N-[(3R)-2,3-Dihydro-1-methyl-2-oxo-5-phenyl-1H-1,4-benzodiazepin-3-yl]-3-(phenylamino)propanamide 3-Bromopropionyl chloride (2.01 mL, 3,428 g, 20 mmol) was added to an ice cooled solution of 3 (R)-amino-1,3-dihydro-1-methyl-5-phenyl-2H-1,4-benzodiazepin-2-one (J. Org. Chem. 1987, 52, 3232–3239) (5.0 g, 18.8 mmol) and triethylamine (2.79 mL, 2.02 mg, 20 mmol) in methylene chloride (85 mL) and the mixture was stirred at room temperature for 18 h. The mixture was washed with saturated aqueous sodium hydrogen carbonate (85 mL), water (2×85 mL), and brine (85 mL), dried (MgSO$_4$) and the solvent was evaporated under reduced pressure. A sample (0.5 g, 1.25 mmol) was dissolved in ethanol (25 mL), aniline (230 mL, 233 mg, 2.5 mmol) was added and the mixture was heated under reflux for 70 h. The mixture was cooled and the solid was collected and recrystallized from ethanol to give (+)-N-[(3R)-2,3-dihydro-1-methyl-2-oxo-5-phenyl-1H-1,4-benzodiazepin-3-yl]-3-(phenylamino)propanamide as a colorless solid, m.p. 218°–221° C., $[\alpha]_D$+58.2° (c=0.585, CHCl$_3$). $^d$H (CDCl$_3$) 7.60–6.71 (16H, m), 5.54 (1H, d, J 8.1 Hz), 3.54 (2H, t, J 6.1 Hz), 3.52 (3H, s), and 2.70 (2H, m). Anal. Calcd. for C$_{25}$H$_{24}$N$_4$O$_2$.0.5 EtOH: C, 71.70; H, 6.25; N, 12.87. Found: C, 71.42; H, 5.98; N, 12.84%.

Example 58

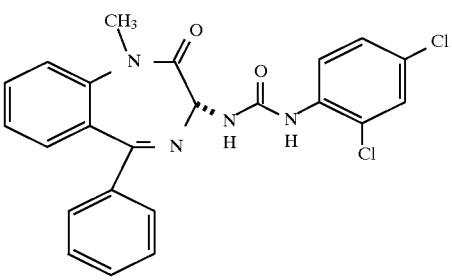

(+)-1-[(3R)-2,3-Dihydro-1-methyl-2-oxo-5-phenyl-1H-1,4-benzodiazepin-3-yl]-3-(2,4-dichlorophenyl)urea 2,4-Dichlorophenylisocyanate (188 mg, 1.0 mmol) was added to a solution of 3 (R)-amino-1,3-dihydro-1-methyl-5-phenyl-2H-1,4-benzodiazepin-2-one (J. Org. Chem. 1987, 52, 3232–3239) (265 mg, 1.0 mmol) in tetrahydrofuran (20 mL). The mixture was stirred at room temperature for 18 h. and the solvent was evaporated under reduced pressure. The residue was purified by flash column chromatography on silica gel, eluting with CH$_2$Cl$_2$/MeOH (99.5:0.5) and the residue was crystallized from CH$_2$Cl$_2$/hexane to give (+)-1-[(3R)-2,3-dihydro-1-methyl-2-oxo-5-phenyl-1H-1,4-benzodiazepin-3-yl]-3-(2,4-dichlorophenyl) urea as a colorless solid, m.p. 215°–216.5° C., $[\alpha]_D$+76.2° (c=0.261, CHCl$_3$).

$^d$H (CDCl$_3$) 8.10 (1H, d, J 9.0 Hz), 7.65–6.95 (13H, m), 5.50 (1H, d, J 9.0 Hz), and 3.50 (3H, s). Anal. Calcd. for $C_{23}H_{18}Cl_2N_4O_2 \cdot 0.3H_2O$: C, 60.22; H, 4.09; N, 12.21. Found: C, 60.28; H, 3.89; N, 12.10%.

Example 59

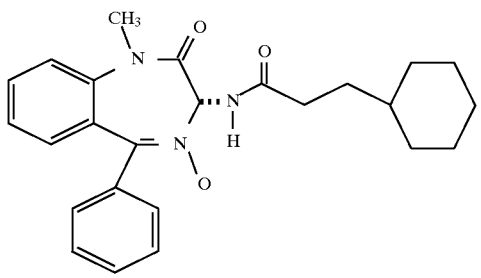

(−)-3-Cyclohexyl-N-[(3R)-2,3-dihydro-1-methyl-2-oxo-4-oxido-5-phenyl-1H-4-benzodiazepin-3-yl]propanamide 3-Chloroperoxybenzoic acid (80%, 0.32 g, 1.5 mmol) was added to a solution of (+)-3-cyclohexyl-N-[(3R)-2,3-dihydro-1-methyl-2-oxo-5-phenyl-1H-1,4-benzodiazepin-3-yl]propanamide (0.60 g, 1.5 mmol) in dichloromethane (25 mL) and the mixture was stirred at room temperature for 18 h. Further 3-chloroperoxybenzoic acid (80%, 0.1 g, 0.5 mmol) was added and the mixture was stirred for 24 h. The mixture was washed with saturated aqueous sodium hydrogen carbonate (4×25 mL), water (2×25 mL) and brine (25 mL), dried ($MgSO_4$) and the solvent was evaporated under reduced pressure. The residue was recrystallized from toluene/hexane (65:35) to give (−)-3-cyclohexyl-N-[(3R)-2,3-dihydro-1-methyl-2-oxo-4-oxido-5-phenyl-1H-1,4-benzodiazepin-3-yl]propanamide as colorless prisms, m.p. 222°–224° C., $[\alpha]_D$ −80.7° (c=1.15, $CHCl_3$). $^dH$ ($CDCl_3$) 7.71–7.23 (10H, m), 6.01 (1H, d, J 9.3 Hz), 3.54 (3H, s), 2.48 (2H, m), and 1.76–0.89 (13H, m).

Anal. Calcd. for $C_{25}H_{29}N_3O_3 \cdot 0.5H_2O$: C, 70.06; H, 7.06; N, 9.81. Found: C, 70.10; H, 6.80; N, 9.79%.

Example 60

N-[2,3-Dihydro-1-(2-dimethylaminoethyl)-2-oxo-5-phenyl-1H-1,4-benzodiazepin-3-yl]-3-(2,4-dichlorophenyl)propanamide Step A:

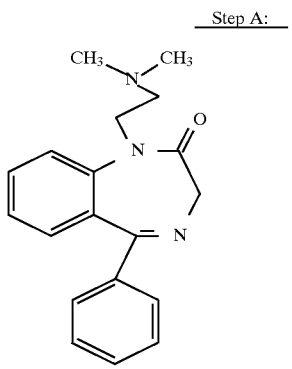

2,3-Dihydro-1-(2-dimethylaminoethyl)-5-phenyl-1H-1,4-benzodiazepin-2-one 2,3-Dihydro-5-phenyl-1H-1,4-benzodiazepin-2-one (1.00 g, 4.23 mmol) was added to hexane washed sodium hydride (60% dispersion in mineral oil, 186 mg, 4.65 mmol) in DMF (5 mL). Further DMF (10 mL) was added and the mixture was stirred at room temperature. 2-(Dimethylamino)ethyl chloride hydrochloride (0.73 g, 5 mmol) was added to hexane washed sodium hydride (60% dispersion in mineral oil, 200 mg, 5.0 mmol) in DMF (5 mL) and the mixtures were combined. Potassium iodide (1 crystal) was added and the mixture was stirred at 100° C. for 30 min. The solvent was evaporated under reduced pressure, water was added and the mixture was extracted with ethyl acetate. The combined organic fractions were washed with water (2×), dried ($MgSO_4$) and the solvent was evaporated under reduced pressure to give 2,3-dihydro-1-(2-dimethylaminoethyl)-5-phenyl-1H-1,4-benzodiazepin-2-one (1.21 g, 93%).

$^dH$ ($CDCl_3$) 7.63–7.16 (9H, m), 4.77 (1H, d, J 10.6 Hz), 4.41 (1H, m), 3.80 (1H, m), 3.78 (1H, d, J 10.6 Hz), 2.49 (2H, m), and 2.13 (6H, s).

Step B:

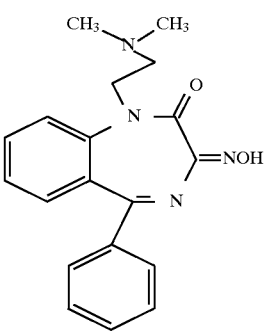

2,3-Dihydro-1-(2-dimethylaminoethyl)-3-hydroxyimino-5-phenyl-1H-1,4-benzodiazepin-2-one 2,3-Dihydro-1-(2-dimethylaminoethyl)-5-phenyl-1H-1,4-benzodiazepin-2-one (1.21 g, 3.9 mmol) was dissolved in toluene (20 mL). The mixture was cooled to −78° C. and potassium t-butoxide (1.0M solution in t-butanol, 4.72 mL, 4.72 mmol) was added. The mixture was stirred at −78° C. for 20 min., then isoamyl nitrite (0.63 mL, 0.55 g, 4.72 mmol) was added. The mixture was stirred at −78° C. for 90 min. then allowed to warm to room temperature and poured into aqueous citric acid (1M, 10 mL). The pH was adjusted to 5.0 with aqueous sodium hydroxide then to 7.0 with saturated aqueous sodium hydrogen carbonate. The mixture was extracted with ethyl acetate (50 mL) and the organic layer was aged at room temperature. The solid which formed was collected and dried in vacuo to give 2,3-dihydro-1-(2-dimethylaminoethyl)-3-hydroxyimino-5-phenyl-1H-1,4-benzodiazepin-2-one (0.876 g, 66%) as a solid, m.p. 232°–234° C. $^dH$ ($d_6$-DMSO) 10.90 (1H, s), 7.72–7.25 (9H, m), 4.40 (1H, m), 3.80 (1H, m), 2.50 (2H, m), and 1.85 (6H, s).

Step C:

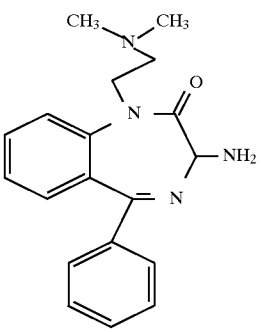

3-Amino-2,3-dihydro-1-(2-dimethylaminoethyl)-5-phenyl-1H-1,4-benzodiazepin-2-one Ethyl isocyanate (320 mL, 287 mg, 4.0 mmol) was added to a mixture of 2,3-dihydro-1-(2-dimethylaminoethyl)-3-hydroxyimino-5-phenyl-1H-1,4-benzodiazepin-2-one (0.91 g, 2.7 mmol) and triethylamine (0.56 mL, 0.41 g, 4.0 mmol) in THF (30 mL). The mixture was heated under reflux for 7 h., further ethyl isocyanate (167 mL, 150 mg, 2.1 mmol) was added and the mixture was heated under reflux for 12 h. The mixture was cooled, the solvent was evaporated under reduced pressure and ethyl acetate (75 mL) and water (25 mL) were added. The organic phase was washed with water (4×25 mL), dried (MgSO$_4$) and evaporated under reduced pressure. The residue was dissolved in ethanol (100 mL), palladium on carbon (10%, 100 mg) was added and the mixture was shaken under hydrogen (50 p.s.i.) for 4.5 h. Further palladium on carbon (10%, 100 mg) was added and the mixture was shaken under hydrogen (50 p.s.i.) for 1.5 h. The mixture was filtered and the solvent was evaporated under reduced pressure. The residue was purified by flash column chromatography on silica gel, eluting with CH$_2$Cl$_2$/MeOH to give 3-amino-2,3-dihydro-1-(2-dimethylaminoethyl)-5-phenyl-1H-1,4-benzodiazepin-2-one (180 mg, 17%).

$^d$H (CDCl$_3$) 7.75–7.17 (9H, m), 4.45 (1H, s), 4.40 (1H, m), 3.82 (1H, m), 2.47 (4H, m), and 2.08 (6H, s).

Step E:

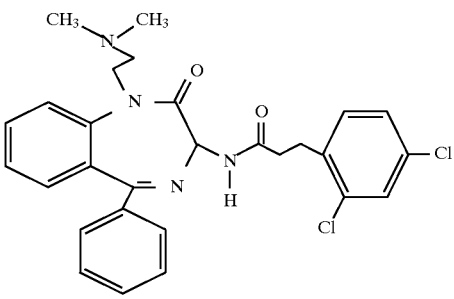

N-[2,3-Dihydro-1-(2-dimethylaminoethyl)-2-oxo-5-phenyl-1H-1,4-benzodiazepin-3-yl]-3-(2,4-dichlorophenyl)propanamide Triethylamine was added to a mixture of 3-amino-2,3-dihydro-1-(2-dimethylaminoethyl)-5-phenyl-1H-1,4-benzodiazepin-2-one (180 mg, 0.6 mmol), 3-(2,4-dichlorophenyl)propanoic acid (131 mg, 0.6 mmol), 1-(3-dimethylaminopropyl)-3-ethylcarbodiimide hydrochloride (115 mg, 0.6 mmol) and 1-hydroxybenzotriazole (81 mg, 0.6 mmol) in DMF (15 mL) until the pH was 9.0. The mixture was stirred at room temperature for 72 h. The solvent was evaporated under reduced pressure and ethyl acetate was added. The mixture was was washed with water, saturated aqueous sodium hydrogen carbonate and water, dried (MgSO$_4$) and evaporated under reduced pressure. The residue was triturated with acetone and recrystallized from i-PrOH/MeOH to give N-[2,3-dihydro-1-(2-dimethylaminoethyl)-2-oxo-5-phenyl-1H-1,4-benzodiazepin-3-yl]-3-(2,4-dichlorophenyl)-propanamide as a solid, m.p. 199°–201° C. $^d$H (CDCl$_3$) 7.60–7.15 (13H, m), 5.50 (1H, d, J 8.0 Hz), 4.40 (1H, m), 3.80 (1H, m), 3.10 (2H, t, J 7.5 Hz), 2.70 (2H, t, J 7.5 Hz), 2.40 (2H, m), and 2.05 (6H, s).

Anal. Calcd. for C$_{28}$H$_{28}$Cl$_2$N$_4$O$_2$: C, 64.25; H, 5.39; N, 10.70. Found: C, 64.23; H, 5.40; N, 10.61%.

Example 61

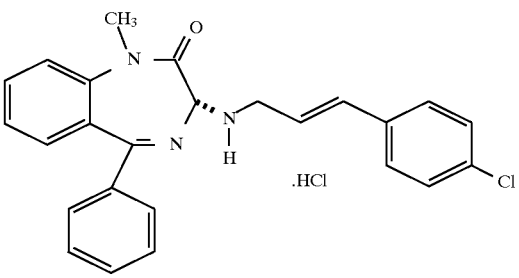

(+)-3 (R)-{N-[3-(4-chlorophenyl)prop-1-en-3-yl]amino}-1,3-dihydro-1-methyl-5-phenyl-2H-1,4-benzodiazepin-2-one hydrochloride A mixture of 3 (R)-amino-1,3-dihydro-1-methyl-5-phenyl-2H-1,4-benzodiazepin-2-one (J. Org. Chem. 1987, 52, 3232–3239) (265 mg, 1 mmol), E-1-chloro-4-(3-chloro-1-propenyl)benzene (281 mg, 1.5 mmol), potassium carbonate (276 mg, 2 mmol) and potassium iodide (25 mg, 0.15 mmol) in acetonitrile (2 mL) was heated under reflux for 4 h. The mixture was cooled and poured into ethyl acetate (10 mL) and water (5 mL). The layers were separated and the aqueous layer was extracted with ethyl acetate (5 mL). The combined organic fractions were washed with brine, dried (Na$_2$SO$_4$) and the solvent was evaporated under reduced pressure. The residue was purified by flash column chromatography on silica gel, eluting with EtOAc/Hexane (65:35 increasing to 100:0). The first compound to elute was suspended in ethanol (1 mL) and ethanolic HCl (6M, 0.11 mL) was added. The mixture was stirred, then the solvent was evaporated under reduced pressure. The residue was triturated with ether and the solid was collected and dried in vacuo to give (+)-3 (R)-{N,N-bis[1-(4-chlorophenyl)propen-3-yl]amino }-1,3-dihydro-1-methyl-5-phenyl-2H-1,4-benzodiazepin-2-one hydrochloride (235 mg, 39%) as a tan solid, m.p. 138°–145° C., [α]$_D$+9.2° (c=0.500, MeOH).

$^d$H (d$_6$-DMSO) 11.2 (1H, br s), 7.77–7.31 (17H, m), 6.85 (2H, br m), 6.54 (2H, m), 5.20 (1H, br s), 4.60–4.00 (4H, m), and 3,46 (3H, s). Anal. Calcd. for C$_{34}$H$_{29}$Cl$_2$N$_3$O.HCl.0.10EtOH: C, 67.60; H, 5.08; N, 6.92. Found: C, 67.60; H, 5.03; N, 7.03%.

The second compound to elute was suspended in ethanol (0.5 mL) and ethanolic HCl (6M, 0.035 mL) was added. The mixture was stirred, then the solvent was evaporated under reduced pressure. The residue was triturated with ether and the solid was collected and dried in vacuo to give (+)-3 (R)-{N-[3-(4-chlorophenyl)propen-3-yl]amino }-1,3-dihydro-1-methyl-5-phenyl-2H-1,4-benzodiazepin-2-one hydro-chloride (56 mg, 12%) as a yellow solid, m.p. 156°–162° C., [α]$_D$ +35° (c=0.100, MeOH).

$^d$H (d$_6$-DMSO) 10.3 (1H, br s), 10.0 (1H, br s), 7.79–7.34 (13H, m), 6.78 (1H, d, J 15.9 Hz), 6.40 (1H, dt, J$_d$ 15.9, J$_t$ 9.0 Hz), 5.13 (1H, s), 4.00 (2H, m), and 3,46 (3H, s). Anal. Calcd. for C$_{25}$H$_{22}$ClN$_3$O.HCl.0.10EtOH.0.40H$_2$O: C, 65.20; H, 5.30; N, 9.05. Found: C, 65.14; H, 5.09; N, 9.33%.

Employing the procedure substantially as described above, but substituting 1-(2-bromoethoxy)-4-nitrobenzene or 4-chlorobenzene-propanol methanesulfonate for the E-1-chloro-4-(3-chloro-1-propenyl)-benzene, the following compounds were prepared:

Example 62

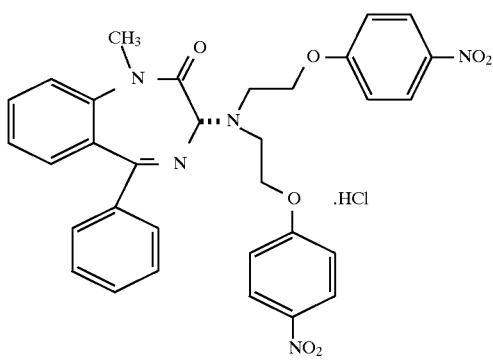

(+)-3 (S)-{ N,N-Bis[2-(4-nitrophenoxy)ethyl]amino }-1,3-dihydro-1-methyl-5-phenyl-2H-1,4-benzodiazepin-2-one hydrochloride m.p. 126°–145° C. $[\beta]_D$+5.0° (0.100, CHCl$_3$).

$^d$H (d$_6$-DMSO) 8.20 (4H, d, J 9.2 Hz), 7.75–7.36 (9H, m), 7.08 (4H, d, J 9.2 Hz), 4.90 (1H, br s), 4.50 (4H, br s), 4.30–3.60 (5H, br m), and 3.34 (3H, s). Anal. Calcd. for C$_{32}$H$_{29}$N$_5$O$_7$.HCl.0.15 EtOH: C, 60.71; H, 4.87; N, 10.96. Found: C, 60.70; H, 4.87; N, 10.70%.

Example 63

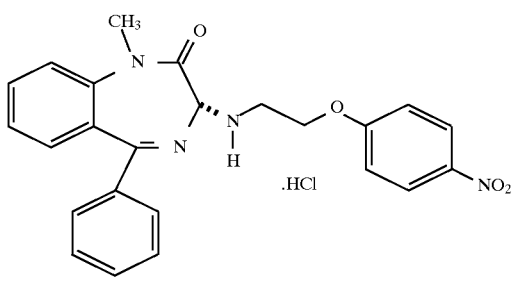

(+)-3 (R)-{N-[3-(4-Nitrophenoxy)ethyl]amino}-1,3-dihydro-1-methyl-5-phenyl-2H-1,4-benzodiazepin-2-one hydrochloride m.p. 154°–160° C., $[\alpha]_D$+84.6° (0.500, MeOH). $^d$H (d$_6$-DMSO) 10.2 (1H, br s), 8.25 (2H, d, J 9.0 Hz), 7.83–7.41 (9H, m), 7.09 (2H, d, J 9.0 Hz), 5.21 (1H, s), 4.57 (2H, m), 3.70 (2H, m), 3,47 (3H, s), and 3,40 (1H, m). Anal. Calcd. for C$_{24}$H$_{22}$N$_4$O$_4$.HCl0.15 EtOH.0.20H$_2$O: C, 61.13; H, 5.13; N, 11.74. Found: C, 61.12; H, 4.92; N, 11.64%.

Example 64

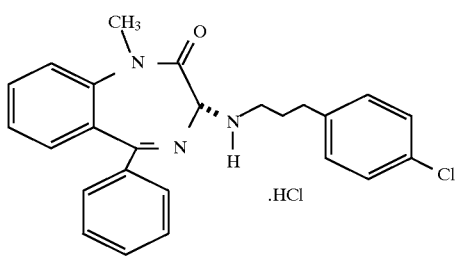

(+)-3 (R)-{N-[3-(4-Chlorophenyl)prop-1-yl]amino }-1,3-dihydro-1-methyl-5-phenyl-2H-1,4-benzodiazepin-2-one hydrochloride m.p. 167°–168° C., $[\alpha]_D$+20.8° (c=0.500, MeOH). $^d$H (d$_6$-DMSO) 9.9 (2H, br m), 7.78–7.26 (13H, m), 5.08 (1H, s), 3,45 (3H, s), 3.20 (1H, m), 3.00 (1H, m), 2.70 (2H, t, J 7.4 Hz), and 2.05 (2H, m). Anal. Calcd. for C$_{25}$H$_{24}$ClN$_3$O.HCl: C, 66.08; H, 5.55; N, 9.25. Found: C, 65.81; H, 5.49; N, 9.30%.

Example 65

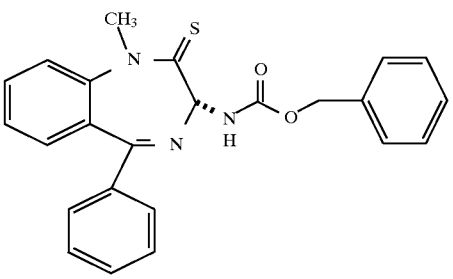

(+)-Phenylmethyl N-[(3R)-2,3-dihydro-1-methyl-5-phenyl-2-thioxo-1H-1,4-benzodiazepin-3-yl]carbamate A mixture of (+)-phenylmethyl N-[(3R)-2,3-dihydro-1-methyl-5-phenyl-2-oxo-1H-1,4-benzodiazepin-3-yl] carbamate (4.0 g, 10 mmol) and 2,4-bis(4-methoxyphenyl)-1,3-dithia-2,4-diphosphetane-2,4-disulfide (4.5 g, 11 mmol) in toluene (100 mL) was heated under reflux for 75 min. The mixture was cooled and the volume was reduced to 30 mL by evaporation under reduced pressure. The residue was purified by flash column chromatography on silica gel, eluting with EtOAc/Hexane (75:25) to give (+)-phenylmethyl N-[(3R)-2,3-dihydro-1-methyl-5-phenyl-2-thioxo-1H-1,4-benzodiazepin-3-yl]carbamate as a solid, m.p. 128°–131° C., $[\alpha]_D$+22.5° (c=0.656, CHCl$_3$).

$^d$H (CDCl$_3$) 7.65–7.26 (15H, m), 5.50 (1H, d, J 8.8 Hz), 5.14 (2H, s), and 3.86 (3H, s). Anal. Calcd. for C$_{24}$H$_{21}$N$_3$O$_2$S.0.25H$_2$O: C, 68.63; H, 5.16; N, 10.01. Found: C, 68.28; H, 5.21; N, 10.06%.

Employing the procedure substantially as described above, but substituting phenylmethyl N-[2,3-dihydro-5-phenyl-2-oxo-1H-1,4-benzodiazepin-3-yl]carbamate for the (+)-phenylmethyl N-[(3R)-2,3-dihydro-1-methyl-5-phenyl-2-oxo-1H-1,4-benzodiazepin-3-yl]carbamate, the following compound was prepared:

Example 66

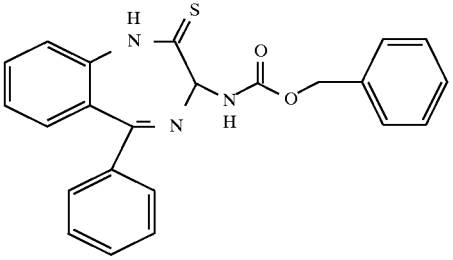

Phenylmethyl N-[2,3-dihydro-5-phenyl-2-thioxo-1H-1,4-benzodiazepin-3-yl]carbamate $^d$H (d$_6$-DMSO) 10.85 (1H, s), 8.42 (1H, d, J 8.6 Hz), 7.65–7.10 (14H, m), 5.10 (2H, s), and 5.05 (1H, d, J 8.6 Hz).

Example 67

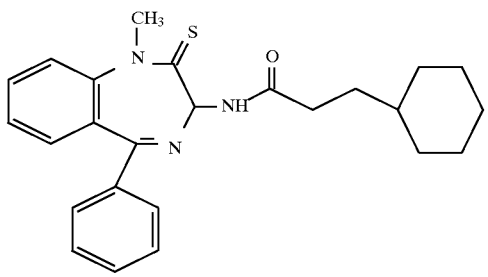

3-Cyclohexyl-N-(2,3-dihydro-1-methyl-5-phenyl-2-thioxo-1H-1,4-benzodiazepin-3-yl)propanamide Hydrogen bromide was bubbled at room temperature through a solution of (+)-phenylmethyl N-[(3R)-2,3-dihydro-1-methyl-5-phenyl-2-thioxo-1H-1,4-benzodiazepin-3-yl]carbamate (0.9 g, 2.1 mmol), acetic acid (5 mL) and dichloromethane (5 mL). After 2 h., the solvent was evaporated under reduced pressure, ether was added and the solid was collected and dried in vacuo. A sample (0.58 g, 1.8 mmol) was suspended in THF (10 mL), triethylamine (0.24 mL, 0.18 g, 1.8 mmol) was added and the mixture was stirred at room temperature for 3 h. In a separate flask, oxalyl chloride (0.20 mL, 0.29 g, 2.3 mmol) was added to a solution of cyclohexanepropionic acid (0.33 mL, 0.30 g, 1.9 mmol) and DMF (1 drop) in THF (10 mL) and the mixture was stirred at room temperature for 3 h. The two mixtures were combined, triethylamine (0.32 mL, 0.23 g, 2.3 mmol) was added and the mixture was stirred at room temperature for 2.5 h. The solvent was evaporated under reduced pressure, water was added and the mixture was extracted with ethyl acetate. The combined organic fractions were washed with water, saturated aqueous sodium hydrogen carbonate, water (2×) and brine, dried ($Na_2SO_4$) and the solvent was evaporated under reduced pressure. The residue was purified by flash column chromatography on silica gel, eluting with $CH_2Cl_2$/MeOH (99.5:0.5) and the residue was recrystallized from EtOAc/Hexane to give 3-cyclohexyl-N-(2,3-dihydro-1-methyl-5-phenyl-2-thioxo-1H-1,4-benzodiazepin-3-yl)propanamide as a solid, m.p. 219°–221° C. $^d$H ($CDCl_3$) 7.95 (1H, br d, J 8.6 Hz), 7.65–7.30 (9H, m), 5.72 (1H, d, J 8.6 Hz), 3.87 (3H, s), 2.41 (2H, t, J 7.6 Hz), and 1.80–0.85 (13H, m). Anal. Calcd. for $C_{25}H_{29}N_3OS.0.25H_2O$: C, 70.81; H, 7.01; N, 9.91. Found: C, 70.80; H, 6.91; N, 9.95%.

Employing the procedure substantially as described above, but substituting phenylmethyl N-[2,3-dihydro-5-phenyl-2-thioxo-1H-1,4-benzodiazepin-3-yl]carbamate for the (+)-phenylmethyl N-[(3R)-2,3-dihydro-1-methyl-5-phenyl-2-thioxo-1H-1,4-benzodiazepin-3-yl]carbamate and an appropriate acid for the cyclohexanepropionic acid, the following compounds were prepared:

Example 68

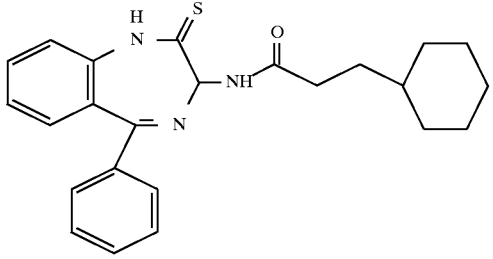

3-Cyclohexyl-N-(2,3-dihydro-5-phenyl-2-thioxo-1H-1,4-benzodiazepin-3-yl)propanamide m.p. 113°–119° C. $^d$H ($CDCl_3$) 9.8 (1H, br s), 7.75–7.25 (10H, m), 5.75 (1H, d, J 8.1 Hz), 2.41 (2H, m), and 1.80–0.85 (13H, m). Anal. Calcd. for $C_{24}H_{27}N_3OS.0.8CH_2Cl_2$: C, 62.91; H, 6.09; N, 8.87. Found: C, 62.88; H, 5.70; N, 9.12%.

Example 69

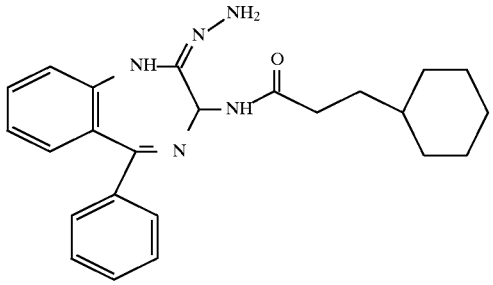

3-Cyclohexyl-N-(2,3-dihydro-2-hydrazono-5-phenyl-1H-1,4-benzodiazepin-3-yl)propanamide Hydrazine (53 mL, 56 mg, 1.8 mmol) was added to a solution of 3-cyclohexyl-N-(2,3-dihydro-1-methyl-5-phenyl-2-thioxo-1H-1,4-benzodiazepin-3-yl)propanamide (120 mg, 0.25 mmol) in methanol (3 mL). The mixture was stirred at room temperature for 3 h. and the solvent was evaporated under reduced pressure. Ethyl acetate was added and the mixture was washed with water and brine, dried ($Na_2SO_4$) and the solvent was evaporated under reduced pressure. The residue was purified by flash column chromatography on silica gel, eluting with $CH_2Cl_2$/MeOH (99.5:0.5 increasing to 98:2) to give 3-cyclohexyl-N-(2,3-dihydro-2-hydrazono-5-phenyl-1H-1,4-benzodiazepin-3-yl)propanamide as a foam.

$^d$H ($CDCl_3$) 7.55–7.00 (11H, m), 5.75 (1H, d, J 7.6 Hz), 3.50 (2H, br s), 2.37 (2H, t, J 8.0 Hz), and 1.80–0.85 (13H, m). Anal. Calcd. for $C_{24}H_{29}N_5O.0.8CH_3OH.0.15CH_2Cl_2$: C, 67.82; H, 7.41; N, 15.85. Found: C, 67.79; H, 7.46; N, 16.05%.

Example 70

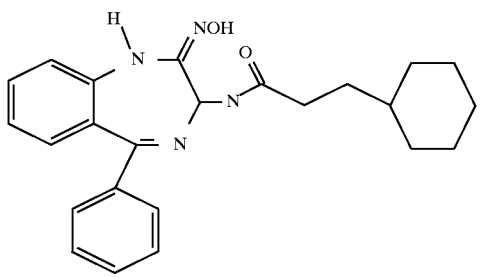

(E)- and (Z)-3-Cyclohexyl-N-(2,3-dihydro-2-hydroxyimino-5-phenyl-1H-14-benzodiazepin-3-yl) propanamide A mixture of 3-cyclohexyl-N-(2,3-dihydro-1-methyl-5-phenyl-2-thioxo-1H-1,4-benzodiazepin-3-yl)propanamide (740 mg, 1.83 mmol), hydroxylamine hydrochloride (140 mg, 2 mmol) and triethylamine (280 mL, 203 mg, 2 mmol) in methanol (15 mL)/THF (15 mL) was stirred at room temperature for 3 h. The solvent was evaporated under reduced pressure and the residue was purified by flash column chromatography on silica gel, eluting with $CH_2Cl_2$/MeOH (98:2). The residue recrystallized from ethyl acetate. The first isomer to crystallize was recrystallized from ethyl acetate to give(E)-3-cyclohexyl-N-(2,3-dihydro-2-hydroxyimino-5-phenyl-1H-1,4-benzodiazepin-3-yl) propanamide as a solid, m.p. 196° C.

$^d$H ($d_6$-DMSO) 12.20 (1H, s), 9.0° (1H, d, J 8.0 Hz), 7.70–7.30 (10 H m), 5.45 (1H, d, J 8.0 Hz), 2.30 (2H, m), and 1.80–0.75 (13H, m).

The second isomer to crystallize was recrystallized from methanol to give (Z)-3-cyclohexyl-N-(2,3-dihydro-2-hydroxyimino-5-phenyl-1H-1,4-benzodiazepin-3-yl) propanamide as a solid, m.p. 219° C.

$^d$H ($d_6$-DMSO) 9.95 (1H, s), 8.95 (1H, s), 8.75 (1H, d, J 8.0 Hz), 7.50–7.00 (9H, m), 5.70 (1H, d, J 8.0 Hz), 2.25 (2H, m), and 1.75–0.75 (13H, m). Anal. Calcd. for $C_{24}H_{28}N_4O_2$: C, 71.26; H, 6.98; N, 13.85. Found: C, 70.89; H, 6.99; N, 13.55%.

Example 71

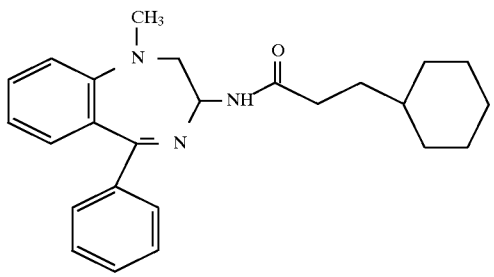

3-Cyclohexyl -N-(2,3-dihydro-1-methyl -5-phenyl -1H-1,4-benzodiazepin-3-yl) propanamide Freshly prepared Raney nickel (400 mg) was added to a solution of 3-cyclohexyl-N-(2,3-dihydro-1-methyl-5-phenyl-2-thioxo-1H-1,4-benzodiazepin-3-yl)propanamide (200 mg, 0.5 mmol) in ethanol (20 mL) and the mixture was stirred at room temperature for 2 h. The mixture was filtered and the solvent was evaporated under reduced pressure. The residue was purified by flash column chromatography on silica gel, eluting with $CH_2Cl_2$/MeOH (99.75:0.25) to give 3-cyclohexyl-N-(2,3-dihydro-1-methyl-5-phenyl-1H-1,4-benzodiazepin-3-yl) propanamide as a foam.

$^d$H (CDCl$_3$) 7.60–6.80 (9H, m), 6.37 (1H, br d, J 6.6 Hz), 5.53 (1H, m), 3.60 (2H, m), 2.77 (3H, s), 2.21 (2H, t, J 8.0 Hz), and 1.85–0.80 (13H, m). Anal. Calcd. for $C_{25}H_{31}N_3O.0.2CH_2Cl_2$: C, 74.45; H, 7.79; N, 10.34. Found: C, 74.68; H, 7.87; N, 10.23%.

Example 72

1-(2,3-Dihydro-1-methyl-2-oxo-5-phenyl-1H-thieno-[2,3-e]-1,4-diazepin-3-yl)-3-(3-methyl-phenyl)urea Step A:

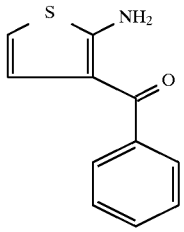

(2-Amino-3-thienyl)phenylmethanone

Triethylamine (6.8 mL, 4.94 g, 49 mmol) was added to a heated (33° C.) mixture of b-oxobenzenepropanenitrile (18.6 g, 128 mmol) and 1,2-dithiane-2,5-diol (9.8 g, 64 mmol) in ethanol (120 mL) and the mixture was stirred at 50° C. for 18 h. The mixture was cooled and the solvent was evaporated under reduced pressure. Dichloromethane was added, the mixture was washed with aqueous hydrochloric acid (0.5M), aqueous sodium hydroxide (1M) and brine, dried ($Na_2SO_4$) and the solvent was evaporated under reduced pressure. The residue was recrystallized from acetonitrile (150 mL) to give (2-amino-3-thienyl)-phenylmethanone as an orange solid (5.7 g, 44%).

$^d$H (CDCl$_3$) 7.70–7.35 (5H, m), 6.95 (2H, br s), 6.90 (1H, d, J 6.3 Hz), and 6.15 (1H, d, J 6.3 Hz).

Step B:

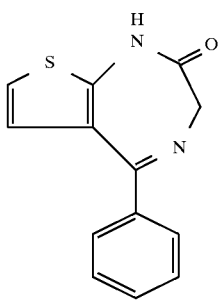

2,3-Dihydro-5-phenyl-1H-thieno[2,3-e]1,4-diazepin-2-one

A solution of 1,3-dihydro-1,3-dioxo-2H-isoindole-2-acetyl chloride (8.6 g, 38 mmol) in dichloromethane (20 mL) was added slowly to cooled (0° C.) mixture of (2-amino-3-thienyl)phenylmethanone (6.8 g, 33 mmol), pyridine (6.34 mL, 6.20 g, 78 mmol) and 4-dimethylamino-pyridine (0.79 g, 6.5 mmol) in dichloromethane (130 mL). The mixture was stirred at 0° C. for 30 min., diluted with dichloromethane (80 mL) and washed with aqueous hydrochloric acid (1M), saturated aqueous sodium hydrogen carbonate and brine. The mixture was dried ($Na_2SO_4$) and the was evaporated under reduced pressure. The residue was triturated with ethanol and the solid was collected and dried in vacuo to give N-(3-benzoylthien-2-yl)-1,3-dihydro-1,3-dioxo-2H-isoindole-2-acetamide as a solid (9.8 g, 76%).

A mixture of N-(3-benzoylthien-2-yl)-1,3-dihydro-1,3-dioxo-2H-isoindole-2-acetamide (10.9 g, 28 mmol) and hydrazine (1.9 mL, 1.94 g, 60 mmol) in THF (500 mL) was heated under reflux for 4 h. The mixture was cooled, filtered and the solvent was evaporated under reduced pressure. Saturated aqueous sodium hydrogen carbonate was added and the mixture was extracted with ethyl acetate. The combined organic fractions were washed with brine, dried (Na$_2$SO$_4$) and the solvent was evaporated under reduced pressure. Acetic acid (300 mL) was added and the mixture was hated under reflux for 15 min. The mixture was cooled and the solvent was evaporated under reduced pressure. Saturated aqueous sodium hydrogen carbonate was added and the mixture was extracted with ethyl acetate. The combined organic fractions were washed with brine, dried (Na$_2$SO$_4$) and the solvent was evaporated under reduced pressure to give 2,3-dihydro-5-phenyl-1H-thieno[2,3-e]-1,4-diazepin-2-one as a foam (3.5 g, 52%).

$^d$H (CDCl$_3$) 9.75 (1H, br s), 7.90–7.30 (5H, m), 6.87 (1H, d, J 6.0 Hz), 6.82 (1H, d, J 6.0 Hz), and 4.45 (2H, s).

Step C:

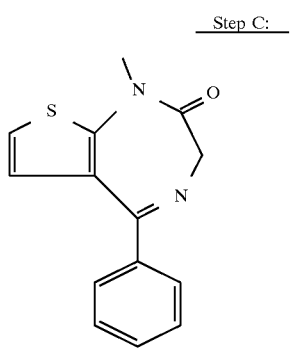

2,3-Dihydro-1-methyl-5-phenyl-1H-thieno[2,3-e]-1,4-diazepin-2-one

Sodium hydride (60% dispersion in mineral oil, 757 mg, 11.3 mmol) was added to a cooled (0° C.) solution of 2,3-dihydro-5-phenyl-1H-thieno[2,3-e]-1,4-diazepin-2-one (2.61 g, 10.8 mmol) in DMF (7 mL). Further DMF (10 mL) was added and the mixture was stirred for 30 min. A solution of iodomethane (0.67 mL, 1.53 g, 10.8 mmol) in ether (20 mL) was added and the mixture was stirred for 1 h. The mixture was poured into water and the mixture was extracted with ethyl acetate. The combined organic fractions were washed with brine, dried (Na$_2$SO$_4$) and evaporated under reduced pressure. The residue was purified by flash column chromatography on silica gel, eluting with CH$_2$Cl$_2$/MeOH (95:5) to give 2,3-dihydro-1-methyl-5-phenyl-1H-thieno[2,3-e]-1,4-diazepin-2-one (1.5 g, 54%).

$^d$H (CDCl$_3$) 7.67–7.35 (5H, m), 7.00 (1H, d, J 6.0 Hz), 6.85 (1H, d, J 6.0 Hz), 4.45 (2H, br s), and 3.50 (3H, s).

Step D:

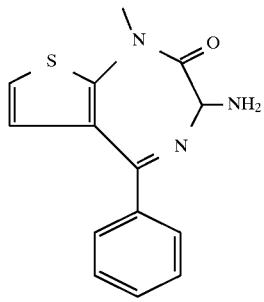

3-Amino-2,3-dihydro-1-methyl-5-phenyl-1H-thieno [2,3-e]-1,4-diazepin-2-one 2,3-Dihydro-1-methyl-5-phenyl-1H-thieno[2,3-e]-1,4-diazepin-2-one (1.5 g, 5.8 mmol) was dissolved in toluene (30 mL). The mixture was cooled to −10° C. and potassium t-butoxide (1.7 g, 15.1 mmol) was added. The mixture was stirred at −10° C. for 15 min., then isoamyl nitrite (1.0 mL, 0.87 g, 7.4 mmol) was added. The mixture was stirred at −10° C. for 1 h. then allowed to warm to room temperature and poured into water (50 mL) and acetic acid (3 mL). The mixture was extracted with ethyl acetate and the combined organic fractions were washed with brine, dried (Na$_2$SO$_4$) and the solvent was evaporated under reduced pressure. The residue was purified by flash column chromatography on silica gel, eluting with EtOAc/Hexane to give 2,3-dihydro-1-methyl-3-hydroxyimino-5-phenyl-1H-thieno[2,3-e]-1,4-diazepin-2-one (0.80 g, 48%).

2,3-Dihydro-1-methyl-3-hydroxyimino-5-phenyl-1H-thieno [2,3-e]-1,4-diazepin-2-one (0.80 g, 2.8 mmol) was dissolved in ethanol (40 mL) and Raney nickel (2 g) was added. The mixture was shaken under hydrogen (50 p.s.i.) for 5 days, adding further Raney nickel (10 g) in portions. The mixture was filtered and the solvent was evaporated under reduced pressure. The residue was purified by flash column chromatography on silica gel, eluting with CH$_2$Cl$_2$/MeOH to give 3-amino-2,3-dihydro-1-methyl-5-phenyl-1H-thieno[2,3-e]-1,4-diazepin-2-one (248 mg, 33%).

$^d$H (CDCl$_3$) 7.50–7.30 (5H, m), 7.05 (1H, d, J 6.0 Hz), 6.85 (1H, d, J 6.0 Hz), 4.57 (1H, s), 3.55 (3H, s), and 1.70 (2H, br s).

Step E:

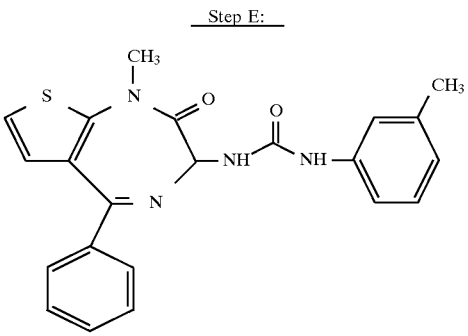

1-(2,3-Dihydro-1-methyl-2-oxo-5-phenyl-1H-thieno[2,3-e]-1,4-diazepin-3-yl)-3-(3-methylphenyl)urea 3-Methylphenylisocyanate (60 mL, 62 mg, 0.46 mmol) was added to a solution of 3-amino-2,3-dihydro-1-methyl-5-phenyl-1H-thieno[2,3-e]-1,4-diazepin-2-one (124 mg, 0.46 mmol) in tetrahydro-furan (5 mL). The mixture was stirred at room temperature for 2 h. and the solvent was evaporated under reduced pressure. The residue was crystallized from EtOAc (4 mL) to give 1-(2,3-dihydro-1-methyl-2-oxo-5-phenyl-1H-thieno[2,3-e]-1,4-diazepin-3-yl)-3-(3-methylphenyl)urea as a solid (94 mg, 50%).

m.p. 128°–130° C. $^d$H (CDCl$_3$) 8.70 (1H, s), 7.65–6.75 (12H, m), 5.55 (1H, d, J 9.0 Hz), 3.55 (3H, s), and 2.30 (3H, s). Anal. Calcd. for C$_{22}$H$_{20}$N$_4$O$_2$S.0.25H$_2$O: C, 64.62; H, 4.99; N, 13.70. Found: C, 64.68; H, 4.96; N, 13.70%.

Example 73

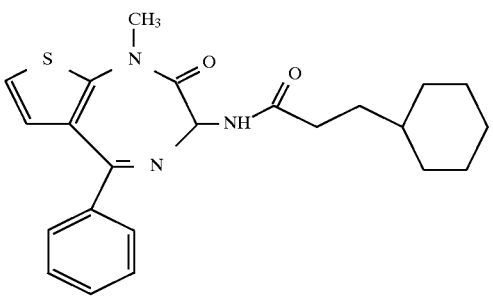

3-Cyclohexyl-N-(2,3-dihydro-1-methyl-2-oxo-5-phenyl-1H-thieno[2,3-e]-1,4-diazepin-3-yl)propanamide Triethylamine (75 mL, 54 mg, 0.54 mmol) was added to a mixture of 3-amino-2,3-dihydro-1-methyl-5-phenyl-1H-thieno[2,3-e]-1,4-diazepin-2-one (82 mg, 0.3 mmol), cyclohexanepropanoic acid (52 mL, 47 mg, 0.3 mmol), 1-(3-dimethylaminopropyl)-3-ethylcarbodiimide hydro-chloride (58 mg, 0.3 mmol) and 1-hydroxybenzotriazole (42 mg, 0.3 mmol) in DMF (1.5 mL). The mixture was stirred at room temperature for 18 h. and ethyl acetate (60 mL) was added. The mixture was washed with aqueous citric acid (10%), saturated aqueous sodium hydrogen carbonate and brine, dried ($Na_2SO_4$) and the solvent was evaporated under reduced pressure. The residue was purified by flash column chromatography on silica gel, eluting with EtOAc/Hexane to give 3-cyclohexyl-N-(2,3-dihydro-1-methyl-2-oxo-5-phenyl-1H-thieno[2,3-e]-1,4-diazepin-3-yl)propanamide as a solid (56 mg, 46%).

m.p. 189°–190° C. $^d$H (CDCl$_3$) 7.65–6.85 (8H, m), 5.65 (1H, d, J 8.0 Hz), 3.55 (3H, s), 2.40 (2H, t, J 7.0 Hz), and 1.80–0.85 (13H, m). Anal. Calcd. for $C_{23}H_{27}N_3O_2S.0.5H_2O$: C, 66.00; H, 6.74; N, 10.04. Found: C, 66.25; H, 6.76; N, 9.83%.

Example 74

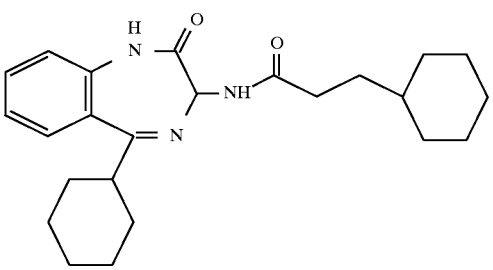

3-Cyclohexyl-N-(5-cyclohexyl-2,3-dihydro-2-oxo-1H-1,4-benzodiazepin-3-yl) propanamide Phenylmethyl N-[5-cyclohexyl-2,3-dihydro-2-oxo-1H-1,4-benzodiazepin-3-yl]carbamate (150 mg, 0.38 mmol) was dissolved in hydrogen bromide in acetic acid (30%, 0.5 mL). After 2 h., ether was added and the solid was collected and dried in vacuo. THF (3 mL) and triethylamine (0.45 mL, 33 mg, 0.32 mmol) were added and the mixture was stirred at room temperature for 3 h. In a separate flask, oxalyl chloride (38 mL, 56 mg, 0.44 mmol) was added to a solution of cyclohexanepropionic acid (61 mL, 56 mg, 0.36 mmol) and DMF (1 drop) in THF (2 mL) and the mixture was stirred at room temperature for 3 h. The two mixtures were combined, triethylamine (61 mL, 44 mg, 0.44 mmol) was added and the mixture was stirred at room temperature for 3 h. The solvent was evaporated under reduced pressure and ethyl acetate was added. The mixture was washed with water (2×), saturated aqueous sodium hydrogen carbonate, water and brine, dried ($Na_2SO_4$) and the solvent was evaporated under reduced pressure. The residue was recrystallized from i-PrOH to give 3-cyclohexyl-N-(5-cyclohexyl-2,3-dihydro-2-oxo-1H-1,4-benzodiazepin-3-yl)propanamide as a solid, m.p. 133°–138° C. $^d$H (CDCl$_3$) 7.85 (1H, br s), 7.62–6.95 (5H, m), 5.40 (1H, d, J 8.7 Hz), 2.77 (1H, m), 2.34 (2H, m), and 2.05–0.75 (23H, m). Anal. Calcd. for $C_{24}H_{33}N_3O_2.0.7C_3H_7OH$: C, 71.64; H, 8.89; N, 9.60. Found: C, 71.28; H, 8.70; N, 9.82%.

Example 75

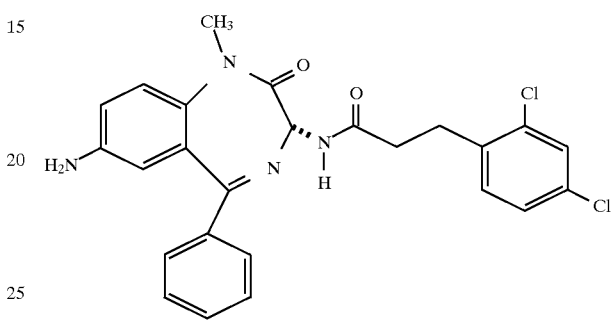

(+)-N-[(3R)-7-Amino-2,3-dihydro-1-methyl-2-oxo-5-phenyl-1H-1,4-benzodiazepin-3-yl]-3-(2,4-dichlorophenyl) propanamide Step A:

To a mixture of 3(R)-amino-1,3-dihydro-1-methyl-5-phenyl-2H-1,4-benzodiazepin-2-one (J. Org. Chem. 1987, 52, 3232–3239) (3.98 g, 15.0 mmol) in concentrated sulfuric acid (15 mL) cooled in an ice-bath was added dropwise a solution of potassium nitrate (2.12 g, 21.0 mmol) in concentrated sulfuric acid (6 mL). The mixture was stirred with cooling for 2 h., then stirred at ambient temperature for 1.5 h. Ice (80 g) was added and the mixture was basified with concentrated ammonium hydroxide to pH 9. The resulting mixture was extracted with ethyl acetate (3×220 mL). The combined organic fractions were washed with brine, dried ($Na_2SO_4$) and the solvent was evaporated under reduced pressure. The residue was purified by flash column chromatography on silica gel, eluting with chloroform/methanol (97:3). The material which eluted was further purified by flash column chromatography on silica gel, eluting with ethyl acetete/methanol (95:5). The material which eluted was stirred under n-butyl chloride (30 mL) and the solvent was evaporated under reduced pressure to give an inseparable mixture of 3(R)-amino-1,3-dihydro-1-methyl-7-nitro-5-phenyl-2H-1,4-benzodiazepin-2-one and 3(R)-amino-1,3-dihydro-1-methyl-7-nitro-5-(2-nitrophenyl)-2H-1,4-benzodiazepin-2-one (3.81 g) in a 3:1 ratio as a yellow solid.

$^d$H (CDCl$_3$) (mononitro compound) 8.43 (1H, dd, J 9, 3 Hz), 8.23 (1H, d, J 3 Hz), 7.59 (2H, m), 7.52 (2H,m), 7.44 (2H,m), 4.47 (1H,s), 3.53 (3H,s), and 2.42 (2H, br s); (dinitro compound) 8.49 (1H, dd, J 9, 3), 8.42 (1H, m), 8.18 (1H, d, J 3 Hz), 8.01 (1H, m), 7.67 (1H, t, J 6 Hz), 7.6–7.4 (2H, m), 4.52 (1H,s), 3.56 (3H,s), and 2.42 (2H, br s).

Step B:

A solution of 3-(2,4-dichlorophenyl)propionic acid (482 mg, 2.2 mmol), DMF (0.017 mL, 0.22 mmol), and thionyl chloride (0.24 mL, 3.3 mmol) in chloroform (2.5 mL) was heated at reflux for 1 h. The solvent was evaporated under reduced pressure to give 3-(2,4-dichlorophenyl)propionyl chloride (520 mg, 100%). To a solution of mixed 3(R)- amino-1,3-dihydro-1-methyl-7-nitro-5-phenyl-2H-1,4-benzodiazepin-2-one and 3(R)-amino-1,3-dihydro-1-methyl-7-nitro-5-(2-nitrophenyl)-2H-1,4-benzodiazepin-2-one (3:1) (621 mg, 2 mmol) and triethylamine (0.305 mL, 2.2 mmol) in methylene chloride (10 mL), was added a solution of 3-(2,4-dichlorophenyl)propionyl chloride (520 mg, 2.2 mmol) in methylene chloride (1.5 mL). The mixture was stirred for 30 min., the solvent was partially evaporated under reduced pressure, and the reaction mixture was purified by flash column chromatography on silica gel, eluting with methylene chloride/ether (90:10) to give a mixture of (+)-N-[(3R)-2,3-dihydro-1-methyl-7-nitro-2-oxo-5-phenyl-1H-1,4-benzodiazepin-3-yl]-3-(2,4-dichlorophenyl)propanamide and (+)-N-[(3R)-2,3-dihydro-1-methyl-7-nitro-2-oxo-5-(2-nitrophenyl)-1H-1,4-benzodiazepin-3-yl]-3-(2,4-dichlorophenyl)propanamide (850 mg, 84%) in a 3:1 ratio as a solid white foam.

$^d$H (CDCl$_3$) (mononitro compound) 8.45 (1H, dd, J 9, 3 Hz), 8.25 (1H, d J 3 Hz), 7.54 (3H, m), 7.45 (2H, m), 7.38 (1H, d, J 2 Hz), 7.26–7.18 (4H, m), 5.50 (1H, d, J 8 Hz), 3.52 (3H, s), 3.10 (2H, m), and 2.70 (2H, m); (dinitro compound) 8.51 (1H, dd, J 9,3 Hz), 8.40 (1H, m), 8.21 (1H, d J 3 Hz), 7.98 (1H, m), 7.68 (1H, t, J 6 Hz), 7.60 (1H, m), 7.44 (1H, m), 7.26–7.15 (4H, m), 5.52 (1H, d, J 8 Hz), 3.55 (3H, s), 3.10 (2H, m), and 2.70 (2H, m).

Step C:

To a solution of mixed N-[(3R)-2,3-dihydro-1-methyl-7-nitro-2-oxo-5-phenyl-1H-1,4-benzodiazepin-3-yl]-3-(2,4-dichlorophenyl)propanamide and (+)-N-[(3R)-2,3-dihydro-1-methyl-7-nitro-2-oxo-5-(2-nitrophenyl)-1H-1,4-benzodiazepin-3-yl]-3-(2,4-dichlorophenyl) propanamide (3:1) (770 mg, 1.5 mmol) in acetic acid (6 mL) was added dropwise in portions over 1.5 h. a solution of 15% titanium (III) chloride in 20–30% hydrochloric acid (7.8 mL, 9.0 mmol). The resulting solution was stirred 30 min., basified with 20% sodium hydroxide solution (pH 9), diluted with water (80 mL) and extracted with ethyl acetate (3×100 mL). The combined organic fractions were washed with brine, dried (Na$_2$SO$_4$) and the solvent was evaporated under reduced pressure. The residue was purified by flash column chromatography on silica gel, eluting with ethyl acetate/hexane (75:25 increasing to 100:0). The first compound to elute was crystallized from ethyl acetate to give (+)-N-[(3R)-7-amino-2,3-dihydro-1-methyl-2-oxo-5-phenyl-1H-1,4-benzodiazepin-3-yl]-3-(2,4-dichlorophenyl)propanamide (413 mg, 57%) as a pale yellow solid, m.p. 179°–180° C., [α]$_D$ +60.2° (c=0.500, CHCl$_3$).

$^d$H (CDCl$_3$) 7.60 (2H, d, J 7 Hz), 7.49–7.36 (5H, m) 7.24 (1H, d, J 9 Hz), 7.17 (2H, m), 6.99 (1H, dd, J 9, 3 Hz), 6.64 (1H,d, J 3 Hz), 5.54 (1H, d, J 8 Hz), 4.80–3.50 (2H, br s), 3.39 (3H, s), 3.09 (2H, t, J 8 Hz), and 2.68 (2H, dt, Jd 3, Jt 8 Hz). Anal. Calcd. for C$_{25}$H$_{22}$Cl$_2$N$_4$O$_2$: C, 62.38; H, 4.61; N, 11.64. Found: C, 62.58; H, 4.68; N, 11.65%.

The second compound to elute was crystallized from ethyl acetate to give (+)-N-[(3R)-7-amino-2,3-dihydro-1-methyl-2-oxo-5-(2-aminophenyl)-1H-1,4-benzodiazepin-3-yl]-3-(2,4-dichlorophenyl)propanamide (114 mg, 15%) as a pale yellow solid, m.p. 188°–189° C., [α]$_D$ +50.0° (c=0.100, MeOH). $^d$H (CDCl$_3$) 7.36 (2H, m), 7.25 (1H, d, J 9 Hz), 7.15 (3H, m), 7.00 (1H, m), 6.88 (2H, m), 6.79 (1H, m), 6.60 (1H, bs), 5.52 (1H, d, J 8 Hz), 4.10–2.80 (4H br s), 3,40 (3H, m), 3.09 (2H, t, J 8 Hz), and 2.69 (2H, m). Anal. Calcd. for C$_{25}$H$_{23}$Cl$_2$N$_5$O$_2$.0.05EtOAc: C, 60.43; H, 4.71; N, 13.99. Found: C, 60.79; H, 4.74; N, 13.83%.

Example 76

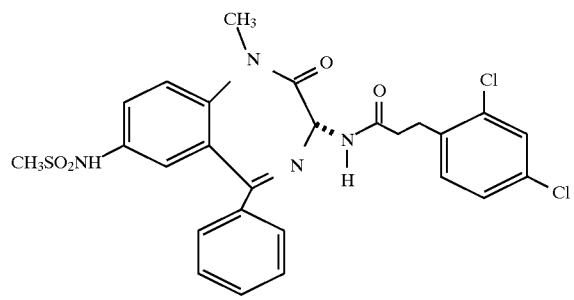

(+)-N-[(3R)-2,3-Dihydro-1-methyl-2-oxo-5-phenyl-7-methanesulfonamido-1H-1,4-benzodiazepin-3-yl]-3-(2,4-dichlorophenyl)propanamide Methanesulfonyl chloride (0.040 mL, 0.52 mmol) was added to a solution of (+)-N-[(3R)-7-amino-2,3-dihydro-1-methyl-2-oxo-5-phenyl-1H-1,4-benzodiazepin-3-yl]-3-(2,4-dichlorophenyl)propanamide (193 mg, 0.40 mmol) and pyridine (0.065 mL, 0.80 mmol) in methylene chloride (1.6 mL). The resulting solution was stirred 2 h. The solution was diluted with ethyl acetate (12 mL), washed with 1N HCl, water, saturated sodium bicarbonate solution, water, and brine (3 mL each), dried (Na$_2$SO$_4$) and the solvent was evaporated under reduced pressure. The residue was dissolved in warn toluene, treated with charcoal, and filtered. The filtrate was diluted with hexane, the mixture was cooled, and the resulting precipitate was collected and dried in vacuo to give (+)-N-[(3R)-2,3-dihydro-1-methyl-2-oxo-5-phenyl-7-methanesulfonamido-1H-1,4-benzodiazepin-3-yl]-3-(2,4-dichlorophenyl)propanamide (152 mg, 68%) as a white solid, m.p. 130°–148° C., [α]$_D$ +111.6° (c=0.500, CHCl$_3$). $^d$H (CDCl$_3$) 7.55–7.32 (9H, m), 7.24 (2H, dd, J 10, 2 Hz), 7.17 (1H, dd, J 9, 2 Hz), 7.05 (1H, d, J 3 Hz), 5.49 (1H, d, J 8 Hz), 3,41 (3H, s), 3.08 (2H, t, J 8 Hz), 2.97 (3H, s), and 2.71 (2H, dt, J$_d$ 3, J$_t$ 8 Hz). Anal. Calcd. for C$_{26}$H$_{24}$Cl$_2$N$_4$O$_4$S: C, 55.82; H, 4.32; N, 10.01. Found: C, 56.12; H, 4.47; N, 9.89%.

Example 77

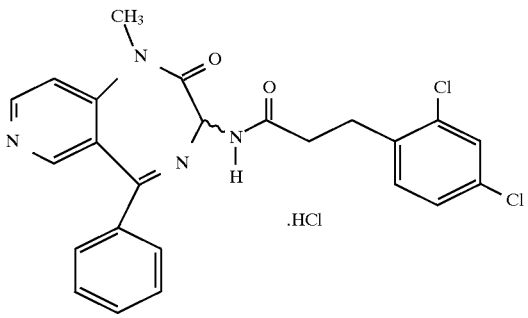

N-(2,3-Dihydro-1-methyl-2-oxo-5-phenyl-1H-pyrido[4,3-e]-1,4-diazepin-3-yl)-3-(2,4-dichlorophenyl)propanamide hydrochloride Step A:

To a solution of 2,3-dihydro-1-methyl-5-phenyl-1H-pyrido[4,3-e]-1,4-diazepine-2-one (J. Med. Chem. 1965, 8, 722–724) (1.63 g, 6.5 mmol) in toluene (32 mL) under argon cooled to −20° C. (ice/methanol bath) was added potassium t-butoxide (1.83 g, 16.3 mmol). The resulting purple suspension was stirred 15 min. at −20° C. and isoamyl nitrite (1.05 mL, 7.8 mmol) was added. The mixture was stirred at −20° C. for 30 min., then poured into a mixture of water (50 mL), acetic acid (3 mL), and ethyl acetate (65 mL). The mixture was stirred to dissolve all solids and the layers were separated. The aqueous layer was extracted with ethyl acetate (65 mL). The combined organic fractions were washed with saturated sodium bicarbonate solution and brine (20 mL each), dried ($Na_2SO_4$), and the solvent was evaporated under reduced pressure. The residue was triturated with cold toluene and the solid was collected and dried in vacuo to give 2,3-dihydro-3-hydroxyimino-1-methyl-5-phenyl-1H-pyrido[4,3-e]-1,4-diazepine-2-one (1.22 g, 67%) as a yellow solid, m.p. 223–20 224° C. $^d$H ($CDCl_3$) 8.92 (1H, bs), 8.73 (1H, d, J 7 Hz), 8.62 (1H, s), 7.80 (2H, dd, J 7, 1 Hz), 7.59 (1H, m), 7.48 (2H, m), 7.26 (1H, d, J 7 Hz), and 3.50 (3H,s).

Step B:

A mixture of 2,3-dihydro-3-hydroxyimino-1-methyl-5-phenyl-1H-pyrido[4,3-e]-1,4-diazepine-2-one (1.77 g, 6.3 mmol) and freshly prepared Raney nickel (3.2 g) in 1:1 ethanol/methanol (190 mL) was shaken on a Parr hydrogenation apparatus under hydrogen (50 psi) for 4 h. The mixture was filtered through filter aid and the filtrate was evaporated under reduced pressure. The residue was purified by flash column chromatography on silica gel, eluting with methanol/chloroform/acetic acid (5:95:1 increasing to 10:90:1). The material which eluted was stirred under chloroform (30 mL) with potassium carbonate (0.3 g) and water (0.2 mL) for 5 min. The mixture was dried ($Na_2SO_4$) and the solvent was evaporated under reduced pressure to give 3-amino-2,3-dihydro-1-methyl-5-phenyl-1H-pyrido[4,3-e]-1,4-diazepine-2-one (276 mg, 16%), as a yellow solid, m.p. 109°–123° C.

$^d$H ($CDCl_3$) 8.72 (1H, d, J 6 Hz), 8.58 (1H, s), 7.61 (2H, m), 7.51 (1H, m), 7.43 (2H, m), 7.26 (1H, m), 4.47 (1H ,s), 3.50 (3H, s), and 2.1 (2H, bs). High res. mass spectrum: Theoretical mass for $Cl_5H_{14}N_{4O}$ (M+1): 267.124586. Measured mass (M+1): 267.123654.

Step C:

A solution of dicyclohexylcarbodiimide (87 mg, 0.42 mmol) in methylene chloride (0.17 mL) was added to a solution of 3-amino-2,3-dihydro-1-methyl-5-phenyl-1H-pyrido[4,3-e]-1,4-diazepine-2-one (93 mg, 0.35 mmol) and 3-(2,4-dichlorophenyl)propionic acid (83 mg, 0.38 mmol) in tetrahydrofuran (0.5 mL) under argon. The resulting mixture was stirred for 5 h., filtered, and the filtrate was evaporated under reduced pressure. The residue was purified by preparative plate chromatography on silica gel eluting with methanol/chloroform/acetic acid (5:95:1). The purified material was stirred under chloroform (5 mL) with potassium carbonate (0.1 g) and water (2 drops) for 5 min. The mixture was dried ($Na_2SO_4$) and the solvent was evaporated under reduced pressure. The residue was suspended in ethanol (2 mL) and ethanolic HCl (6.8M, 0.147 L) was added. The mixture was stirred, the resulting precipitate was collected and dried in vacuo to give N-(2,3-dihydro-1-methyl-2-oxo-5-phenyl-1H-pyrido[4,3-e]-1,4-diazepin-3-yl)-3-(2,4-dichlorophenyl)propanamide hydrochloride (32 mg, 18%) as a white solid, m.p. 218°–219° C.

$^d$H ($d_6$-DMSO) 9.38 (1H, d, J 8 Hz), 8.86 (1H, bs), 8.59 (1H bs), 7.79 (1H, d, J 6 Hz), 7.56 (3H, m), 7.51 (2H, m), 7.39 (2H, m), 7.25 (1H, m), 7.16 (1H, m), 5.37 (1H, d, J 8 Hz), 3,44 (3H, s) 2.94 (2H, t, J 7 Hz), and 2.64 (2H, t, J 7 Hz). Anal. Calcd. for $C_{24}H_{20}Cl_2N_4O_2 \cdot HCl$: C, 57.22; H, 4.20; N, 11.12. Found: C, 56.87; H, 4.18; N, 11.09%.

Example 78

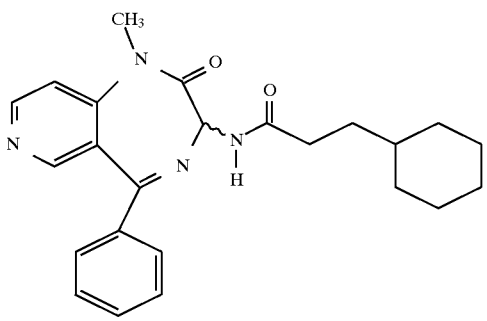

N-(2,3-Dihydro-1-methyl-2-oxo-5-phenyl-1H-pyrido [4,3-e]-1,4-diazepin-3-yl)-3-(cyclohexyl)propanamide A solution of dicyclohexylcarbodiimide (87 mg, 0.42 mmol) in methylene chloride (0.17 mL) was added to a solution of 3-amino-2,3-dihydro-1-methyl-5-phenyl-1H-pyrido[4,3-e]-1,4-diazepine-2-one (93 mg, 0.35 mmol) and cyclohexanepropionic acid (0.065 mL, 0.38 mmol) in tetrahydrofuran (0.5 mL) under argon. The resulting mixture was stirred for 5 h., filtered, and the filtrate was evaporated under reduced pressure. The residue was purified by preparative plate chromatography on silica gel eluting with methanol/chloroform/acetic acid (5:95:1). The purified material was stirred under chloroform (5 mL) with potassium carbonate (0.1 g) and water (2 drops) for 5 min. The mixture was dried ($Na_2SO_4$) and the solvent was evaporated under reduced pressure. The residue was crystallized from toluene to give N-(2,3-dihydro-1-methyl-2-oxo-5-phenyl-1H-pyrido[4,3-e]-1,4-diazepin-3-yl)-3-(cyclohexyl) propanamide (47 mg, 33%) as a white crystalline solid, m.p. 170°–173° C.

$^d$H ($CDCl_3$) 8.75 (1H, d, J 6 Hz), 8.61 (1H, s), 7.58 (2H, m), 7.52 (1H, m), 7.45 (2H, m), 7.31 (1H, d, J 6 Hz), 7.21 (1H, d, J 8 Hz), 5.54 (1H, d, J 8 Hz), 3.51 (3H, s), 2.39 (2H, m), 1.73 (4H, m), 1.63 (3H, m), 1.85–1.12 (4H, m), and 0.94 (2H, m). Anal. Calcd. for $C_{24}H_{28}N_4O_2 \cdot 0.10PhCH_3$: C, 71.70; H, 7.02; N, 13.54. Found: C, 71.78; H, 7.01; N, 13.57%.

Employing the procedure substantially as described above, but substituting 3-(4-trifluoromethylphenyl)-propionic acid for the cyclohexanepropionic acid, the following compound was prepared:

Example 79

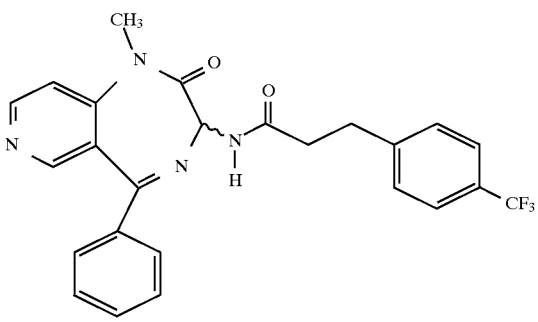

N-(2,3-Dihydro-1-methyl-2-oxo-5-phenyl-1H-pyrido[4,3-e]-1,4-diazepin-3-yl)-3-(4-trifluoromethylphenyl) propanamide m.p. 191°–192° C. $^d$H ($CDCl_3$) 8.76 (1H, d, J 6 Hz), 8.61 (1H, s), 7.56 (4H, m), 7.52 (1H, m), 7.42 (2H, d, J 7 Hz), 7.38 (2H, m), 7.30 (1H, d, J 6 Hz), 7.22 (1H, d, J 8 Hz), 5.51 (1H, d, J 8 Hz), 3.50 (3H, s), 3.09 (2H, t, J 8 Hz), and 2.73 (2H, t, J 8 Hz). Anal. Calcd. for $C_{25}H_{21}F_3N_4O_2 \cdot 0.20PhCH_3$: C, 65.39; H, 4.70; N, 11.56. Found: C, 65.69; H, 4.64; N, 11.95%.

Example 80

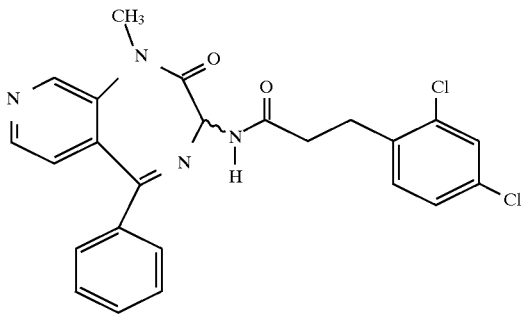

N-(2,3-Dihydro-1-methyl-2-oxo-5-phenyl-1H-pyrido[3,4-e]-1,4-diazepin-3-yl)-3-(2,4-dichlorophenyl)propanamide Step A:

To a solution of 2,3-dihydro-1-methyl-5-phenyl-1H-pyrido[3,4-e]-1,4-diazepine-2-one (*Can. J. Chem.* 1987, 65, 1158–1161) (1.43 g, 5.7 mmol) in toluene (28 mL) under argon cooled to −20° C. (ice/methanol bath) was added potassium t-butoxide (1.59 g, 14.2 mmol). The resulting purple suspension was stirred 15 min. at −20° C. and isoamyl nitrite (0.92 mL, 6.8 mmol) was added. The mixture was stirred at −20° C. for 30 min., then poured into a mixture of water (25 mL), acetic acid (2.5 mL), and ethyl acetate (55 mL). The mixture was stirred to dissolve all solids and the layers were separated. The aqueous layer was extracted with ethyl acetate (2×55 mL). The combined organic fractions were washed with saturated sodium bicarbonate solution and brine (20 mL each), dried ($Na_2SO_4$), and the solvent was evaporated under reduced pressure. The residue was triturated with hexane and the solid was collected and dried in vacuo to give 2,3-dihydro-3-hydroxyimino-1-methyl-5-phenyl-1H-pyrido[3,4-e]-1,4-diazepine-2-one (1.60 g, 100%) as a tan foam. $^dH$ (CDCl$_3$) 8.77 (1H, s), 8.50 (1H, d, J 4 Hz), 7.81 (2H, dd, J 8, 1 Hz), 7.60 (1H, m), 7.49 (3H, m), 7.32 (1H, d, J 5 Hz), and 3.55 (3H,s).

Step B:

A solution of stannous chloride dihydrate (3.72 g, 16.5 mmol) in concentrated hydrochloric acid (11 mL) was added dropwise to 2,3-dihydro-3-hydroxyimino-1-methyl-5-phenyl-1H-pyrido[3,4-e]-1,4-diazepine-2-one (1.54 g, 5.5 mmol) cooled in an ice bath. The resulting solution was stirred at ambient temperature for 3 h. The solution was diluted with water (20 mL), basified with concentrated ammonium hydroxide (18 mL), and extracted with ether (4×75 mL). The combined organic fractions were washed with brine (30 mL), dried ($Na_2SO_4$), and the solvent was evaporated under reduced pressure. The residue was purified by flash column chromatography on silica gel, eluting with methanol/chloroform/acetic acid (5:95:1 increasing to 10:90:1). The material which eluted was stirred under chloroform (20 mL) with potassium carbonate (0.3 g) and water (2 drops) for 5 min. The mixture was dried ($Na_2SO_4$) and the solvent was evaporated under reduced pressure. The residue was stirred under hexane, and the resulting solid was collected to give 3-amino-2,3-dihydro-1-methyl-5-phenyl-1H-pyrido[3,4-e]-1,4-diazepine-2-one (241 mg, 16%) as a yellow solid, m.p. 94°–118° C.

$^dH$ (CDCl$_3$) 8.79 (1H, s), 8.48 (1H, d, J 5 Hz), 7.62 (2H, dd, J 8, 1 Hz), 7.51 (1H, m), 7.45 (2H, m), 7.24 (1H, dd, J 5, 1 Hz), 4.47 (1H, s), 3.55 (3H, s), and 2.2 (2H, bs). Anal. Calcd. for $C_{15}H_{14}N_4O \cdot 0.25 (C_2H_5)_2O$: C, 67.46; H, 5.84; N, 19.67. Found: C, 67.28; H, 5.66; N, 19.53%.

High res. mass spectrum: Theoretical mass for $C_{15}H_{14}N_4O$ (M+1): 267.124586. Measured mass (M+1): 267.123093.

Step C:

A solution of oxalyl chloride (0.023 mL, 0.26 mmol) in methylene chloride (0.2 mL) was added dropwise to a solution of 3-(2,4-dichlorophenyl)propionic acid (48 mg, 0.22 mmol) and DMF (1 drop) in methylene chloride (0.5 mL) cooled in an ice-bath. The resulting solution was stirred 1 h. with cooling. The solvent was evaporated under reduced pressure to give 3-(2,4-dichlorophenyl)-propionyl chloride (52 mg, 100%). To a solution of 3-amino-2,3-dihydro-1-methyl-5-phenyl-1H-pyrido[3,4-e]-1,4-diazepine-2-one (53 mg, 0.20 mmol) and pyridine (0.021 mL, 0.22 mmol) in methylene chloride (3 mL), was added a solution of 3-(2,4-dichlorophenyl)-propionyl chloride (52 mg, 0.22 mmol) in methylene chloride (0.5 mL). The mixture was stirred for 1 h., the solvent was partially evaporated under reduced pressure, and the reaction mixture was purified by flash column chromatography on silica gel, eluting with methanol/ether (5:95 increasing to 7.5:92.5). The material which eluted was crystallized from toluene/hexane to give N-(2,3-dihydro-1-methyl-2-oxo-5-phenyl-1H-pyrido[3,4-e]-1,4-diazepin-3-yl)-3-(2,4-dichlorophenyl)propanamide (38 mg, 38%) as a white crystalline solid, m.p. 220°–221° C. $^dH$ (CDCl$_3$) 8.81 (1H, s), 8.52 (1H, d, J 5 Hz), 7.56 (2H, dd, J 7, 2 Hz), 7.51 (1H, m), 7.44 (2H, d, J 6 Hz), 7.40 (1H, m), 7.27 (2H, m), 7.18 (2H, dd, J 8, 2 Hz), 5.48 (1H,d, J 8 Hz), 3.55 (3H, s), 3.10 (2H, t, J 7 Hz), and 2.71 (2H, dt, $J_d$ 2 $J_t$ 8 Hz). Anal. Calcd. for $C_{24}H_{20}Cl_2N_4O_2 \cdot 0.25PhCH_3$: C, 63.06; H, 4.52; N, 11.43. Found: C, 63.03; H, 4.48; N, 11.25%.

Example 81

N-[2,3-Dihydro-1-methyl-2-oxo-5-isopropyl-1H-1,4-benzodiazepin-3-yl]-3-(2,4-dichlorophenyl)propanamide

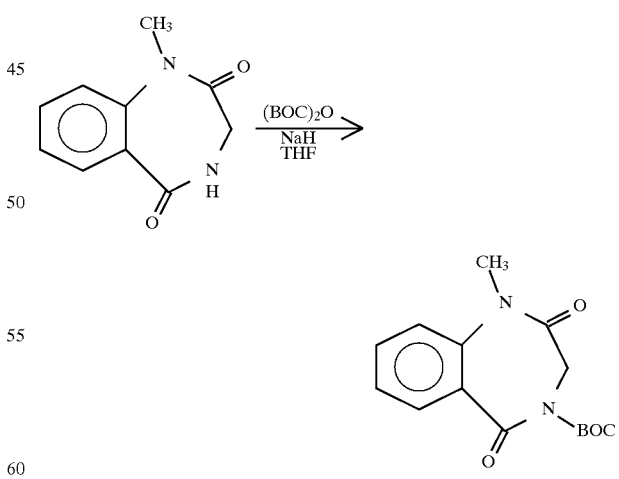

To a solution of the benzodiazepine (1.0 g, 5.3 mmol) in THF (20 mL) at −78° C. under argon was added 60% (NaH, 2.52 g, 6.3 mmol) Boc anhydride (1.27 g, 5.8 mmol) and the mixture stirred at −78° C. for ½ hour. The reaction was then allowed to warm to 25° C. and stirred for 2 hours before quenching into cold aq. NH$_4$Cl (10%) and extracting the product into ethyl acetate (3×50 mL). Concentration of the dried (Na₂SO₄) extracts gave an oil which was passed through silica (EtOAc/hexane) to give 1.35 g product (89%).
¹H NMR (CDCl₃) d: 1.60 (s, 9H), 3,40 (s, 3H), 3.95 (brd, 1H), 4.80 (brd, 1H), 7.20 (d, 1H), 7.30 (q, 1H), 7.60 (t, 1H), 7.92 (d, 1H).

Step B:

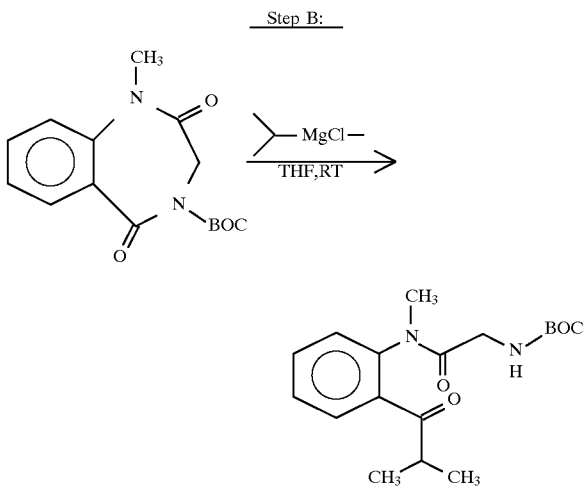

To a solution of the BOC-benzodiazepine (4.0 g, 13.8 mmol) in THF (80 mL) under argon was rapidly added a solution of isopropylmagnesium chloride (2.0M ) in THF (7.66 mL, 15.3 mmol). The reaction was stirred for ½ hour, quenched into aq NH₄Cl (50 mL), and extracted with ethyl acetate (2×200 mL). The organic extracts were concentrated and chromatographed on silica (1:1, EtOAC/hexane) to give 1.55 g (34%) of product.
¹H NMR (CDCl₃) d: 1.14 (d, 3H), 1.19 (d, 3H), 1.40 (s, 9H), 3.13 (s, 3H), 3.2–3.8 (m, 3H), 5.45 (brs, 1H), 7.28 (dt, 1H), 7.48 (dt, 1H), 7.56 (dt, 1H), 7.72 (dd, 1H).

Step C:

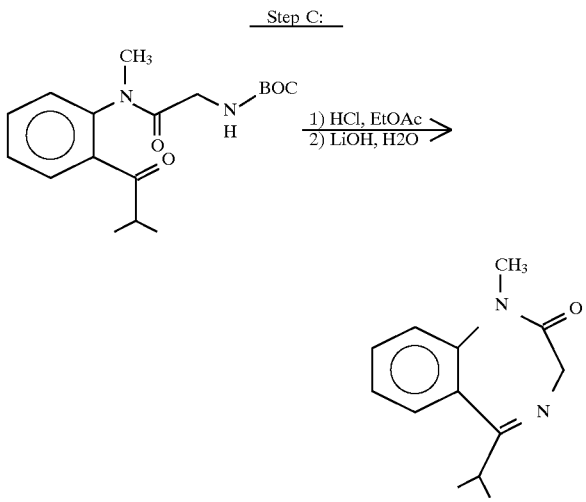

To a 0° C. solution of the isopropylphenone (1.55 g) in ethyl acetate was added anhydrous HCl gas over 90 min. The reaction was then concentrated in vacuo to give a solid which was dissolved in H₂O (40 mL) and the pH adjusted to 11.0 with 1N LiOH. After 30 min. at pH=11.0 the pH was adjusted to 7.0 with 1N HCl and product extracted into ethyl acetate. The organic extracts were dried (Na₂SO₄), filtered and concentrated to give a solid 1.22 g, 100%.
¹H NMR (CDCl₃) d: 0.95 (d, 3H), 1.30 (d, 3H), 3.16 (septet, 1H), 3.36 (s, 3H), 3.60 (d, 1H), 4.60 (d, 1H), 7.2–7.3 (m, 2H), 7.45–7.55 (m, 2H).

Step D:

The benzodiazepine obtained in Step C was converted to the oxime as described in Example 80 Step A.

Step E:

The oxime (2 gms) was dissolved in acetic acid (150 mL) and 10% Pd/C (1 gm) added. The mixture was stirred rapidly under an atmosphere of hydrogen for 90 min or until complete by HPLC. The reaction was filtered, the catalyst washed with methylene chloride (200 mL) and the filtrates concentrated in vacuo to an oil. The oil was dissolved in saturated aqueous sodium bicarbonate (100 mL) and product extracted with ethyl acetate (3×150 mLs). Concentration of the dried (Na₂SO₄) extracts gave 2.60 gms (97%).

Step F:

The anine was coupled with 3-(2,4-dichlorophenyl)-propionic acid as described in Example 43 to yield N-(2,3-dihydro-1-methyl-2-oxo-5-isopropyl-1H-1,4-benzodiazepin-3-yl)-3-(2,4-dichlorophenyl) propanamide.

¹H NMR (CDCl₃) d: 0.92 (d, 3H), 1.25 (d, 3H), 2.65 (dt, 2H), 3.05 (t, 2H), 3.15 (SepT, 1H), 3,40 (s, 3H), 5.38 (d, 1H), 7.0–7.6 (m, 8H).

The following compounds were prepared in a similar manner as described in Example 81, using the appropriate Grignard reagent in place of isopropyl magnesium chloride.

Example 82

N-[2,3-dihydro-1-methyl-2-oxo-5-isopropyl-1H-1,4-benzodiazepin-3-yl]-3-cyclohexylpropanamide m.p. 164°–165° C. CHN: Anal. Calcd. for C₂₂H₃₁N₃O₂: C, 71.51; H, 8.46; N, 11.37; Observed: C, 71.72; H, 8.39; N, 11.32

Example 83

N-[2,3-dihydro-1-methyl-2-oxo-5-isopropyl-1H-1,4-benzodiazepin-3-yl]-3-(4-trifluoromethylphenyl) propanamide m.p. 187°–188° C. ¹H NMR (CDCl₃) d: 0.92 (d, 3H), 1.25 (d, 3H), 2.66 (dt, 2H), 3.04 (t, 2H), 3,15 (SepT, 1H), 3,40 (S, 3H), 5.38 (d, 1H), 7.14 (brd, 1H), 7.25–7.6 (m, 8H).

Employing substantially the same methods described in Example 80, but replacing Step E with the reduction method described below, the following compounds were prepared:

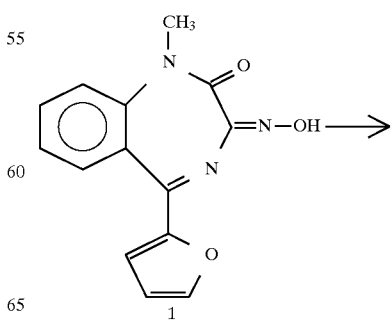

-continued

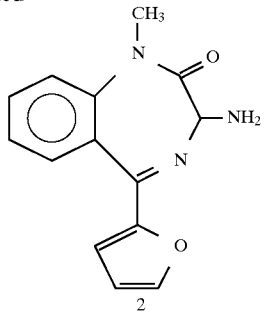

To a solution of the oxime 1 (1.28 g, 0.0048 mole) in $H_2O$ (130 ml) and THF (65 ml) was added sodium dithionite ($Na_2S_2O_4$) (13.0 g, 0.075 mole). The mixture was stirred for 2 hours then diluted with saturated aqueous sodium bicarbonate (50 ml) and product extracted into ethyl acetate (2×150 ml). The organic extracts were combined, dried over $Na_2SO_4$, filtered, and concentrated to give an oil (1.0 g). The oil was chromatographed on silica using ethyl acetate followed by 10% methanol/methylene chloride to give pure amine 0.778 g (64%).

$^1$H NMR (DMSO) d 3.32 (s, 3H), 4.30 (s, 1H), 6.64 (d, d, 1H), 6.76 (d, 1H), 7.35 (dt, 1H), 7.58–7.74 (m, 3H), 7.88 (m, 1H).

Example 84
N-[2,3-dihydro-1-methyl-2-oxo-5-(2-furanyl)-1H-1,4-benzodiazepin-3-yl]-3-cyclohexylpropanamide m.p. 168°–169° C. CHN: Anal. Calcd. for $C_{23}H_{27}N_3O_3$: C, 70.21; H, 6.92; N, 10.68; Observed: C, 70.15; H, 6.67; N, 10.64

Example 85
N-[2,3-dihydro-1-methyl-2-oxo-5-(2-furanyl)-1H-1,4-benxodiazepin-3-yl]-3-(4-triflouromethylphenyl)propanamide m.p. 155°–157° C. CHN: Anal. Calcd. for $C_{24}H_{20}N_3O_3F_3$: C, 63.29; H, 4.432; N, 9.23; Observed: C, 63.22; H, 4.44; N, 9.07

Example 86
N-[2,3-dihydro-1-methyl-2-oxo-5-(2-furanyl)-1H-1,4-benzodiazepin-3-yl]-3-(2,4-dichlorophenyl)propanamide m.p. 132°–133° C.; CHN: Anal. Calcd. for $C_{23}H_{19}N_3O_3Cl_2$; C, 60.54; H, 4.20; N, 9.21; Found: C, 60.62; H, 4.07; N, 9.07

Example 87
N-[2,3-dihydro-1-methyl-2-oxo-5-(3-furanyl)-1H-1,4-benzodiazepin-3-yl]-3-cyclohexylpropanamide m.p. 199°–200° C. $^1$H NMR (CDCl$_3$) d: 0.9–1.8 (brm, 3H), 2.38 (t, 2H), 3,42 (S, 3H), 5.55 (brd, 1H), 6.90 (S, 1H), 7.2–7.77 (m, 7H)

Example 88
N-[2,3-Dihydro-1-methyl-2-oxo-5-(3-furanyl)-1H-1,4-benzodiazepin-3-yl]-3-(4-trifluoromethylphenyl)propanamide m.p. 213°–214° C. $^1$H NMR (CDCl$_3$) d: 2.71 (dt, 2H), 3.05 (t, 2H), 3,42 (S, 3H), 5.72 (d, 1H), 6.82 (brS, 1H), 7.2–7.7 (m, 11H)

Example 89
N-[2,3-Dihydro-1-methyl-2-oxo-5-[2'-(4,4-dimethyl-2-oxazolinyl)-phenyl]-1H-14-benzodiazepin-3-yl]-3-(2,4-dichlorophenyl)propanamide The subject compound was prepared substantially as described in Example 81.

m.p. 194°–195° C. CHN: Anal. Calcd. for $C_{30}H_{28}N_4O_3Cl_2$; C, 63.95; H, 5.01; N, 9.94; Found: C, 63.70; H, 5.01; N, 9.96

Example 90
N-[2,3,4,5-Tetrahydro-1-methyl-2-oxo-5-isopropyl-1H-1,4-benzodiazepin-3-yl]-3-cyclohexylpropanamide

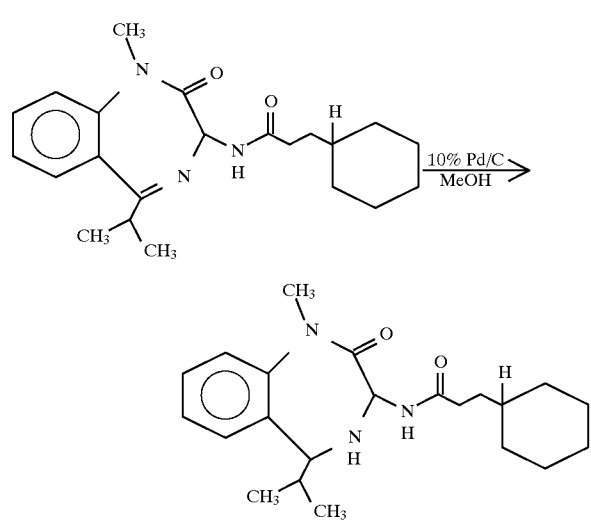

A solution of N-[2,3-dihydro-1-methyl-2-oxo-5-isopropyl-1H-1,4-benzodiazepin-3-yl]-3-cyclohexylpropanamide (50 mg) in methanol (10 mL), containing 10% Pd/C (50 mg) was stirred under 1 atmosphere of hydrogen for 18 hours. Filtration of the reaction, concentration and crystallization from diethyl ether gave 21 mg N-[2,3,4,5-tetrahydro-1-methyl-2-oxo-5-isopropyl-1H-1,4-benzodiazepin-3-yl]-3-cyclohexylpropanamide.

CHN: Anal. Calcd. for $C_{22}H_{33}N_3O_2$; C, 71.12; H, 8.95; N, 11.31; Observed: C, 70.98; H, 8.97; N, 11.15;
m.p. 114°–115° C.

Example 91
N-[2,3-dihydro-1-methyl-2-oxo-5-methyl-1H-1,4-benzodiazepin-3-yl]-3-(2,4-dichlorophenyl)propanamide Step A:

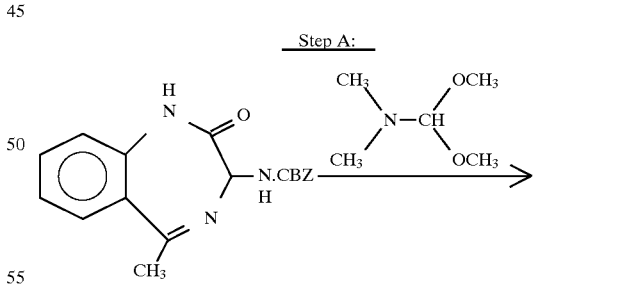

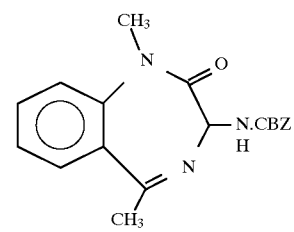

To CBZ-benzodiazepine (250 mg, 0.776 mmol) in toluene (25 mL) at reflux was added dropwise a solution of DMF dimethylacetal (1.09 mL) in toluene (10 mL). The reaction was refluxed for 5 hours, cooled and concentrated to an oil. The oil was triturated with ether to give a white solid (124 mg).

$^1$H NMR (CDCl$_3$) d: 2.50 (s, 3H), 3,42 (s, 3H), 5.12–5.20 (m, 3H), 6.62 (d, 1H), 7.25–6.4 (m, 7H), 7.5–7.6 (m, 2H).

Step B:

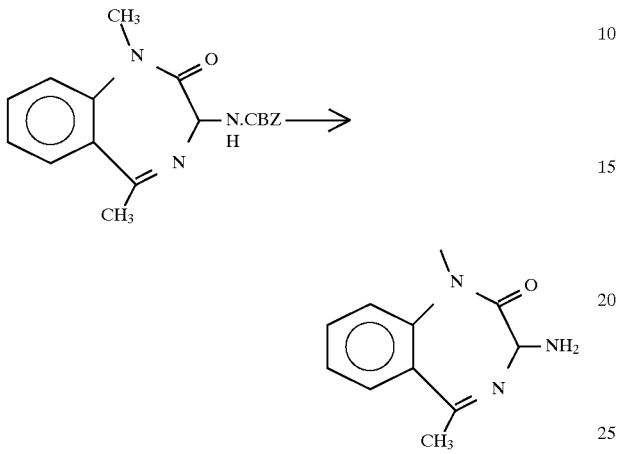

The CBZ-amine-N-methyl amide (190 mg) was treated with 30% HBr/AcOH (0.8 mL) for 1 hour at room temperature. The reaction mixture was poured into ether (10 mL) at 0° C. and the solid filtered. Solid dissolved in 10% Aq. NaOH (5 mL) and CH$_2$C$_{12}$ (10 mL) and organic layer separated, dried (Na$_2$SO$_4$), filtered and concentrated to an oil (172 mg, 110%).

$^1$H NMR (CDCl$_3$) d: 2.42 (s, 3H), 3.05 (brs, 2H), 3,40 (s, 3H), 4.40 (s, 1H), 7.2–7.6 (m, 4H).

Step C:

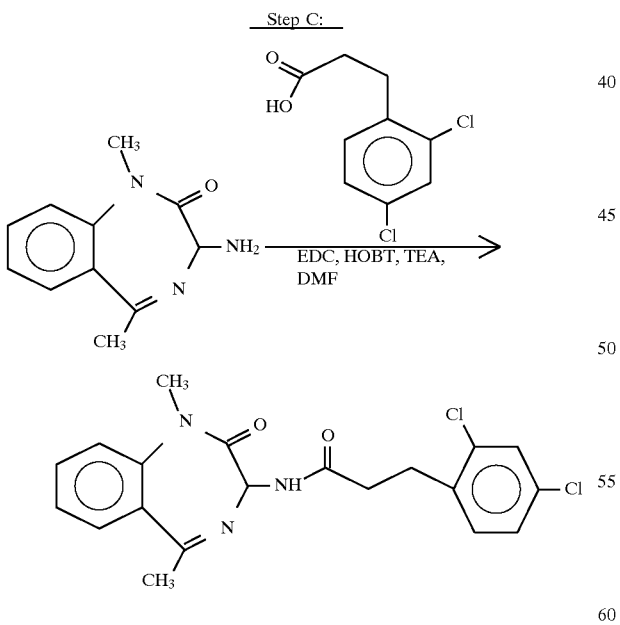

N-[2,3-dihydro-1-methyl-2-oxo-5-methyl-1H-1,4-benzodiazepin-3-yl]-3-(2,4-dichlorophenyl)propanamide was prepared in a similar manner as described previously in Example 43.

m.p. 194°–195° C.; CHN: Anal. Calcd. for C$_{20}$H$_{19}$N$_3$O$_2$Cl$_2$; C, 59.42; H, 4.74; N, 10.39; Observed: C, 59.50; H, 4.74; N, 10.44; $^1$H NMR (CDCl$_3$) d: 2.49 (brs, 3H), 2.65 (dt, 2H), 3.05 (t, 2H), 3,42 (s, 3H), 5.35 (d, 1H), 71–7.6 (m, 8H).

Example 92

N-[2,3-Dihydro-1-methyl-2-oxo-[4,5-a]-(1-oxo-1,3-dihydro-2H-isoindole)-1H-1,4-benzodiazepin-3-yl]-3-(2,4-dichlorophenyl)propanamide

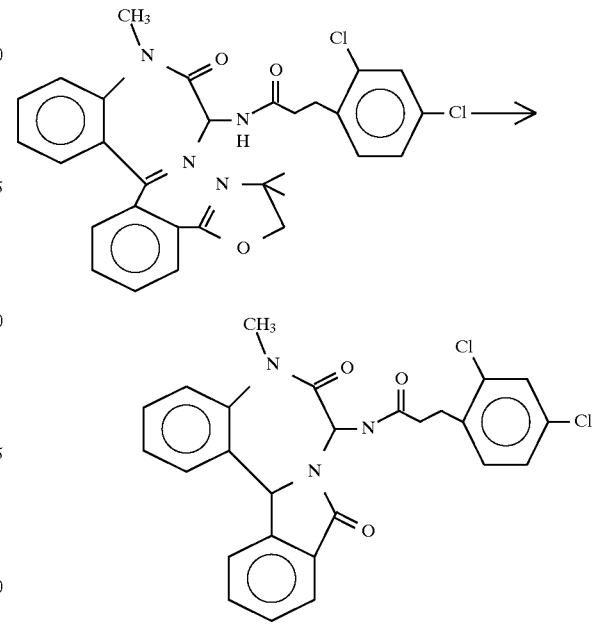

To a solution of N-[2,3-dihydro-1-methyl-2-oxo-5-[2'-(4,4-dimethyl-2-oxazolinyl)phenyl]-1H-1,4-benzodiazepin-3-yl]-3-(2,4-dichlorophenyl)propanamide (100 mg, 0.178 mmol) in methylene chloride was slowly added methyl trifluoromethanesulfonate (22 mL, 0.198 mmol). After stirring 5 minutes, sodium borohydride (7.6 mg, 0.20 mmol) in asolute ethanol (0.5 mL) was added and reaction stirred 30 min. the product was extracted into ethyl acetate and purified by column chromatography on silica (60% ethyl acetate/hexane) to give 30 mg N-[2,3-dihydro-1-methyl-2-oxo-[4,5-a]-(1-oxo-1,3-dihydro-2H-isoindole)-1H-1,4-benzodiazepin-3-yl]-3-(2,4-dichlorophenyl)propanamide.

$^1$H NMR (CDCl$_3$) d: 2.70 (m, 2H), 3.12 (t, 2H), 3.55 (s, 3H), 5.68 (s, 1H), 5.90 (d, 1H), 6.85 (dd, 1H), 7.05 (brd, 1H), 7.1–7.5 (m, 9H), 7.85 (d, 1H). MS M$^{+1}$-494.

Example 93

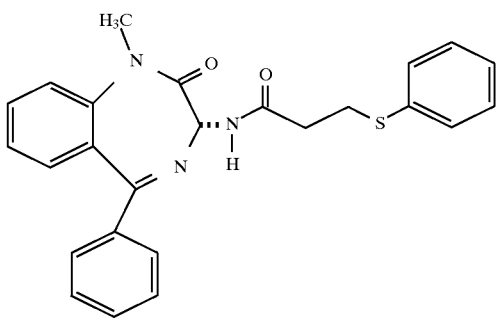

3R-(+)-3-(Phenylthio)-N-[2,3-dihydro-1-methyl-2-oxo-5-phenyl-1H-1,4-benzodiazepin-3-yl]propanamide To a stirred solution of 3-bromopropionic acid (10 g, 6.5 mmol) in DMF (20 mL) was added K$_2$CO$_3$ (1.8 g, 13 mmol)

and thiophenol (0.72 g, 6.5 mmol). This was heated to 50° C. for 1 h. The mixture was then diluted with 200 mL H₂O and extracted with 2×100 mL EtOAc. The combined organics were washed with 100 mL H₂O and dried with Na₂SO₄. This was evaporated to give 1.52 g of a colorless oil, 1.18 g corrected for residual DMF by NMR.

The above oil was taken up in 30 mL DMF and 1-(3-dimethylaminopropyl)-3-ethylcarbodiimide hydrochloride (2.45 g, 12.8 mmol) and 1-hydroxybenztriazole hydrate (1.73 g, 12.8 mmol) were added. This was stirred for 5 min at rt. 3-(R)-Amino-1,3-dihydro-1 methyl-5-phenyl-2H-1,4-benzodiazepin-2-one (0.66 g, 2.6 mmol) was then added and the reaction was stirred at rt overnight. The reaction was diluted with 200 mL H₂O and extracted with 2×150 mL EtOAc. The combined organics were washed with 1×100 mL H₂O, dried with Na₂SO₄ and evaporated. The residue was chromatographed over silica eluting with 2% MeOH:CHCl₃. Collected pure fractions, evaporated. Evaporated from diethyl ether to give 770 mg of a white foam.

Anal. Calcd for C₂₅H₂₃N₃O₂S.0.05 Hexane: C, 70.04; H, 5.51; N, 9.69. Found: C 69.91, H 5.40, N 9.78.

Example 94

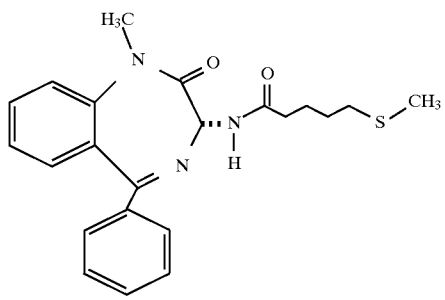

3R-(+)-5-(Methylthio)-N-[2,3-dihydro-1-methyl-2-oxo-5-phenyl-1H-1,4-benzodiazepin-3-yl]propanamide To an aqueous solution of K₂CO₃ (0.76 g, 5.5 mmol) was added 5-bromopentanoic acid and sodium thiomethoxide. This was stirred at rt overnight. The reaction was diluted with 50 mL H₂O and acidified to pH=0 with 6N HCl. Extracted with 2×50 mL EtOAc. Dried with Na₂SO₄, evaporated to give 0.55 g of a yellow oil.

The above oil was taken up in 10 mL DMF and 1-(3-dimethyl-aminopropyl)-3-ethylcarbodiimide hydrochloride (1.30 g, 6.8 mmol) and 1-hydroxybenztriazole hydrate (0.92 g, 6.8 mmol) were added. 3-(R)-Amino-1,3-dihydro-1-methyl-5-phenyl-2H-1,4-benzodaizepin-2-one (0.85 g, 3,4 mmol) was then added and the reaction was stirred overnight at rt. The reaction was diluted with 100 mL H₂O and extracted with 2×50 mL EtOAc. Combined organics were dried with brine and Na₂SO₄, and evaporated to give yellow oil. The residue was chromatographed over silica eluting with 50:50 EtOAc:Hex to 100% EtOAc. Pure fractions were collected to give 1.33 g of a colorless oil, 0.4 g of which was chroma-tographed over silica eluting with 2% MeOH:CH₂Cl₂. Pure fractions were collected, and evaporated from ethyl ether:hexane to give a white powder mp. 61°–65° C. Anal. Calcd for C₂₂H₂₅N₃O₂S.0.35H₂O: C, 65.76; H, 6.45; N, 10.46. Found: C, 65.81; H, 6.21; N, 10.57.

Example 95

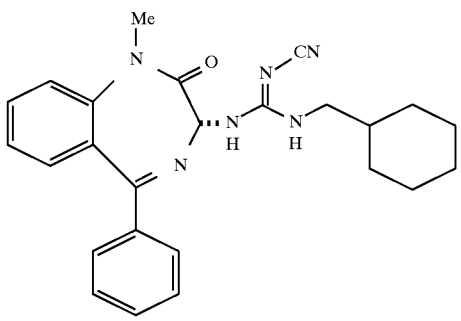

N-cyano-N'-cyclohexylmethyl-N''-(1,3-dihydro-1-methyl-2-oxo-5-phenyl-2H-1,4-benzodiazepin-3-yl)guanidine A solution of 3-(R)-amino-1,3-dihydro-1-methyl-5-phenyl-2H-1,4-benzodiazepin-2-one (1 g, 3.7 mmole) in acetonitrile (20 mL) was treated with diphenylcyanocarbonimidate (0.9 g, 3.7 mmole) and stirred at room temperature for thirty minutes. Cyclohexylmethylamine (0.84 g, 7.4 mmole) was then added and the reaction stirred at room temperature for two hours. The reaction was poured into 100 mL of 0.1N HCl and extracted with 3×100 mL portions of ethyl acetate. The organic layers were combined and washed once with saturated sodium bicarbonate (50 mL), dried over anhydrous magnesium sulfate, filtered, and concentrated at reduced pressure. The residue was chromatographed on silica gel eluting with 50% ethyl acetate/hexane to give 0.875 g of the product. The analytical sample was crystallized from ethyl acetate.

m.p. 158°–161° C. Anal. Calcd. for C₂₅H₂₈N₆ O: C, 70.07; H, 6.59; N, 19.61. Found: C, 70.05; H, 6.59; N, 19.64%.

Example 96

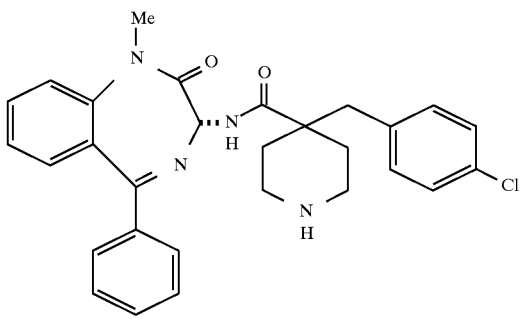

N-(1,3-Dihydro-1-methyl-2-oxo-5-phenyl-2H-1,4-benzodiazepin-3-yl)-4-(4-chlorobenzyl)-4-piperidinecarboxamide dihydrochloride
Step A:
Preparation of N-tert-butyloxycarbonyl-4-(4-chlorobenzyl)-4-piperidinecarboxylic acid A solution of N-Boc-ethylisonipecotate (51.4 g, 200 mmole) in THF (1 L at –60° C. was treated with a solution of lithium bistrimethylsilyl amide (220 mL of a 1N solution in THF, 220 mmole). After stirring at –60° C. for 5 minutes, a solution of 4-chlorobenzyl chloride (33.8 g, 210 mmole) in THF (200 mL) was added and the reaction allowed to warm to room temperature. Most of the THF (about 800 mL) was removed by evaporation at reduced pressure. The remainder was poured into 1 L of 1N HCl and extracted with two 800 mL portions of ethyl acetate. The organic layers were combined and washed once with saturated sodium bicarbonate (500 mL), dried over anhydrous magnesium sulfate, filtered, and concentrated at reduced pressure. The residue was chromatographed on silica gel eluting with 10%–20% ethyl acetate/hexane to give the product ester which was used directly. The material thus obtained was dissolved in THF (100 mL) and IPA (100 mL) and treated with 350 mL of 10N NaOH. The mixture was heated to reflux for 30 hours. The reaction was cooled to room temperature and poured over a mixture of crushed ice (2 L), 6N HCl (500 mL) and saturated potassium hydrogen sulfate (1 L. The mixture was extracted with two 1 L portions of ethyl acetate. The organic layers were combined and dried over anhydrous magnesium sulfate, filtered, and concentrated at reduced pressure to give 52 g of the product.

m.p. 179°–180° C., $^1$H NMR CDCl$_3$ d 7.26 (d, J=8 Hz, 2H), 7.03 (d, J=8 Hz, 2H), 3.98 (m, 2H), 3.0–2.8 (m, 2H), 2.84 (s, 2H), 2.10-2.00 ( m, 2H), 1.55–1.40 (m, 2H), 1.45 (s, 9H)

Step B:

Preparation of N-(1,3-dihydro-1-methyl-2-oxo-5-phenyl-2H-1,4-benzodiazepin-3-yl)-4-(4-chlorobenzyl)-4-piperidinecarboxamide dihydrochloride A mixture consisting of N-tert-butyloxycarbonyl-4-(4-chlorobenzyl)-4-piperidinecarboxylic acid (1.48 g, 4.18 mmole), 3-(R)-amino-1,3-dihydro-1-methyl-5-phenyl-2H-1,4-benzodiazepin-2-one (1 g, 3.7 mmole), hydroxybenzotriazole (1.17 g, 8.66 mmole), 1-(3-dimethylaminopropyl)-3-ethylcarbodiimide hydrochloride (1.49 g, 7.70 mmole), diisopropylethyl amine (0.53 g, 4.13 mmole), and DMF (10 mL) was stirred at room temperature for 18 hours. The reaction was poured into 1N HCl and extracted with ethyl acetate (4×50 mL). The organic layers were combined and washed once with saturated sodium bicarbonate (50 mL), once with saturated sodium chloride (50 mL), dried over anhydrous magnesium sulfate, filtered, and concentrated at reduced pressure. The residue was chromatographed on silica gel eluting with 25%–50% ethyl acetate/hexane to give 2.34 g of the product amide which was used directly.

The material thus obtained was dissolved in ethyl acetate (50 mL) and HCl (g) was bubbled into the reaction for 5 minutes. The reaction was concentrated at reduced pressure and the residue recrystallized from ethyl acetate to give 1.13 g of the product as a pale yellow solid.

m.p. 190°–195° C. Anal. Calcd. for C$_{29}$H$_{29}$ClN$_4$O$_2$.2HCl: C, 60.68; H, 5.44; N, 9.76. Found: C, 60.47; H, 5.5; N, 9.42%.

Utilizing the procedures substantially as desribed above except substituting N-Boc-ethylnipecotate for N-Boc-ethyl isonipecotate there were obtained the following compounds Example 97

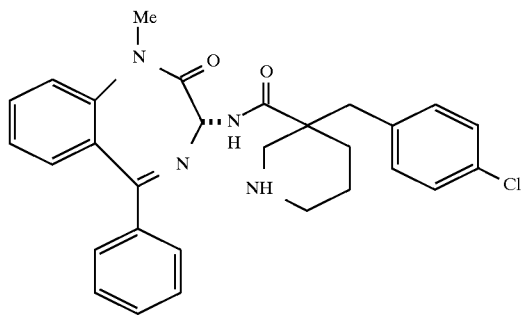

N-(1,3-dihydro-1-methyl-2-oxo-5-phenyl-2H-1,4-benzodiazepin-3-yl)-3-(4-chlorobenzyl)-3-piperidinecarboxamide hydrochloride A+B isomers Isomer A m.p. 205°–210° C. Anal. Calcd. for C$_{29}$H$_{28}$ClN$_4$O$_2$.HCl.0.5 CH$_3$CH$_2$OH.0.8H$_2$O: C, 62.67; H, 6.07; N, 9.75. Found: C, 62.69; H, 5.94; N, 9.42%.

Isomer B m.p. 200°–205° C. Anal. Calcd. for C$_{29}$H$_{28}$ClN$_4$O$_2$.HCl..0.1 CH$_3$CH$_2$OCOCH$_3$.1.6H$_2$O: C, 61.39; H, 5.96; N, 9.74. Found: C, 61.39; H, 5.66; N, 9.56%.

Example 98

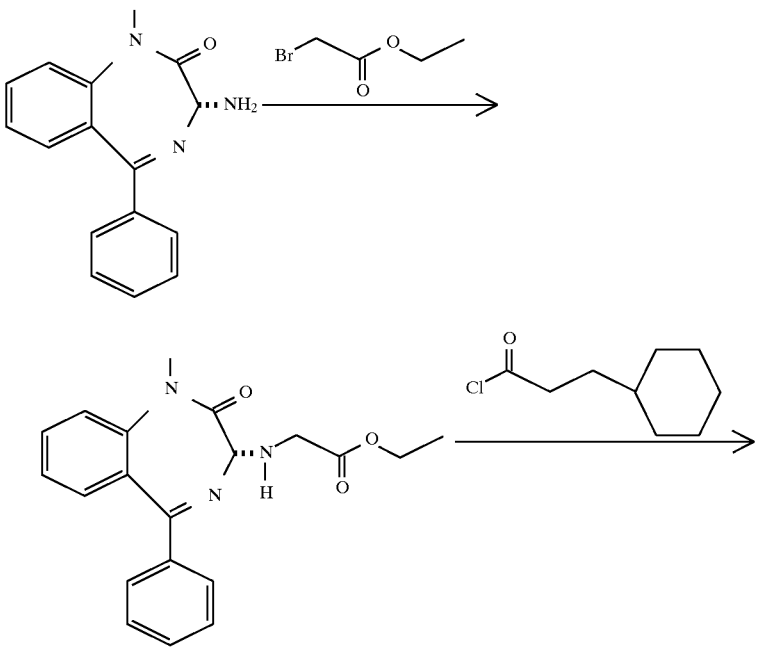

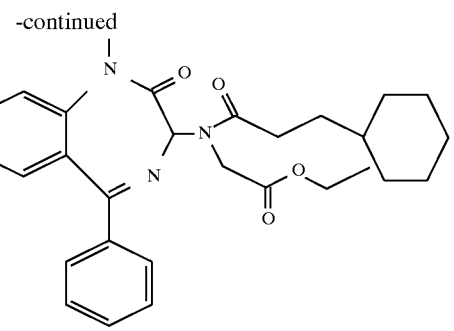

(+)-3-Cyclohexyl-N-[2,3-dihydro-1-methyl-2-oxo-5-phenyl-1H-1,4-benzodiazepin-3-yl]-N-(ethoxycarbonylmethyl)propanamide 3-(R)-Amino-1,3-dihydro-1-methyl-5-phenyl-2H-1,4-benzodiazepin-2-one (5.0 g, 18.8 mmol) in acetonitrile (100 mL) was mixed with ethyl bromoacetate (2.1 mL, 18.8 mmol) and sodium hydrogen carbonate (4.0 g) was suspended in the mixture. The mixture was stirred and heated at reflux for 2 h. After that time, the reaction was cooled to room temperature, diluted with 150 mL water, and extracted with ethyl acetate (3×100 mL). The organic layers were combined, dried with magnesium sulfate, gravity filtered, and the solvent was removed in vacuo. The resulting oil was chromatographed over silica in 3:1 ethyl acetate: hexane, yielding the mono-alkylated product (2.58 g, 39%) as well as the starting 1,4-benzodiazepin-2-one and bis-alkylated material. To a solution of 3-cyclohexylpropionic acid (1.0 g, 6.40 mmol) in methylene chloride (30 mL) was added oxalyl chloride (0.56 mL, 6.40 mmol) and catalytic (N,N)-dimethyl formamide (2 drops). After 0.5 h, a solution of the acetate (2.25 g, 6.40 mmol) in methylene chloride (10 mL) was added and the reaction was stirred for 0.25 h. The reaction was then diluted with methylene chloride (150 mL) and saturated aqueous sodium hydrogen carbonate (150 mL) was added. The aqueous portion was extracted again with methylene chloride (2×100 mL) and the organics were combined, dried with magnesium sulfate, gravity filtered, and the solvent was removed in vacuo. The resulting oil was chromatographed over silica with 1:1 ethyl acetate:hexane, yielding a foam that was crystallized with ether, giving 2.0 g (64%) of the product.

m.p. 120°–122° C., [α]$_D$+0.63° (c=0.79; MeOH). Anal. Calcd. for C$_{29}$H$_{35}$N$_3$O$_4$: C, 71.14; H, 7.21; N, 8.58. Found: C, 71.13; H, 7.13; N, 8.75%.

The following compound was prepared in a manner substantially as desribed above except substituting ethyl bromobutyrate for ethyl bromoacetate.

Example 99

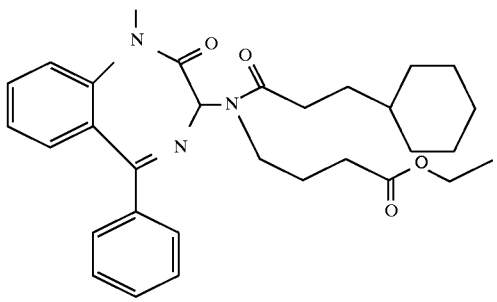

3-Cyclohexyl-N-[2,3-dihydro-1-methyl-2-oxo-5-phenyl-1H-1,4-benzodiazepin-3-yl]-N-(ethoxycarbonylpropyl)propanamide m.p. 103°–105° C., [α]D 0.00°; c=0.85; MeOH. Anal. Calcd. for C$_{31}$H$_{39}$N$_3$O$_4$.0.40 mol H$_2$O: C, 70.94; H, 7.64; N, 8.01. Found: C, 70.91; H, 7.44; N, 8.12%.

Example 100

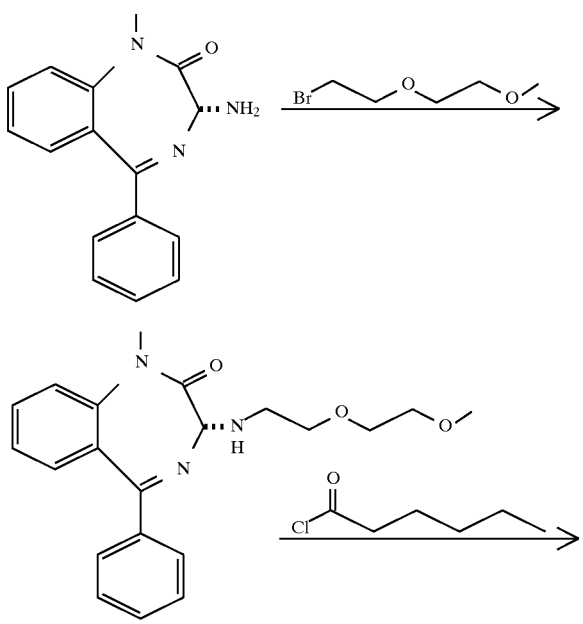

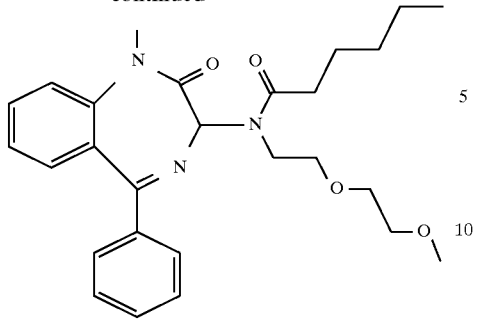

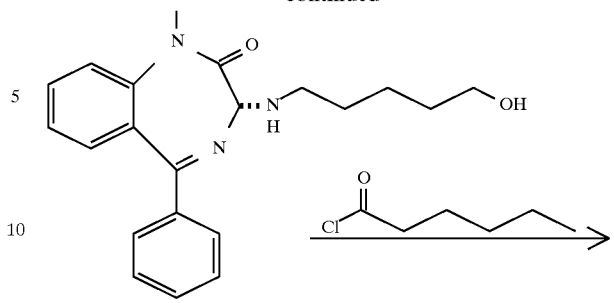

N-[2,3-Dihydro-1-methyl-2-oxo-5-phenyl-1H-1,4-benzodiazepin-3-yl]-N-[2-(2-methoxyethoxy)ethyl]hexanamide 3-(R)-Amino-1,3-dihydro-1-methyl-5-phenyl-2H-1,4-benzodiazepin-2-one (1.33 g, 5.0 mmol) in N,N-dimethyl formamide (30 mL) was mixed with 1-bromo-2-(2-methoxyethoxy)ethane (1.35 mL, 5.0 mmol) and triethylamine (1.0 mL). The mixture was stirred and heated at reflux for 4 h. After that time, the reaction was cooled to room temperature, diluted with 150 mL water, and extracted with ethyl acetate (3×100 mL). The organic layers were combined, dried with magnesium sulfate, gravity filtered, and the solvent was removed in vacuo. The resulting oil was chromatographed over silica in 1:1 ethyl acetate:hexane, yielding the mono-alkylated product (1.2 g, 65%) as well as the starting 1,4-benzodiazepin-2-one and bis-alkylated material. To a solution of the monoalkylated material (1.2 g, 3.27 mmol) in methylene chloride (20 mL) was added hexanoyl chloride (0.96 mL, 3.27 mmol) and the reaction was stirred for 0.25 h. The reaction was then diluted with methylene chloride (150 mL) and saturated aqueous sodium hydrogen carbonate (150 mL) was added. The aqueous portion was extracted again with methylene chloride (2×100 mL) and the organics were combined, dried with magnesium sulfate, gravity filtered, and the solvent was removed in vacuo. The resulting oil was chromatographed over silica with 1:1 ethyl acetate: hexane, yielding an oil, giving 580 mg (38%) of the product. $[\alpha]D$ 0.00°; c=0.27; MeOH.

Anal. Calcd. for $C_{27}H_{35}N_3O_4 \cdot 0.80$ mol $H_2O$: C, 67.56; H, 7.69; N, 8.75. Found: C, 67.56; H, 7.39; N, 8.85%.

Example 101

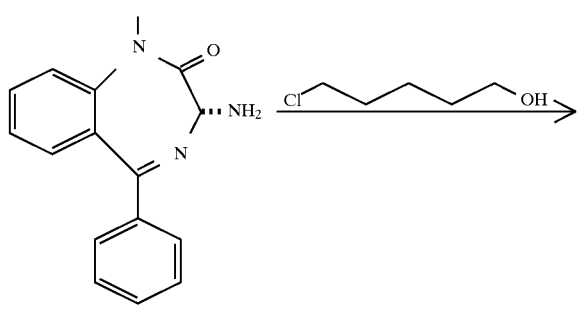

(+)-N-[2,3-Dihydro-1-methyl-2-oxo-5-phenyl-1H-1,4-benzodiazepin-3-yl]-N-(5-hydroxypentyl)hexanamide 3-(R)-Amino-1,3-dihydro-1-methyl-5-phenyl-2H-1,4-benzodiazepin-2-one (1.33 g, 5.0 mmol) in acetonitrile (40 mL) was mixed with 5-chloropentan-1-ol (0.61 g, 5.0 mmol) and sodium hydrogen carbonate (2.0 g) was suspended in the mixture. The mixture was stirred and heated at reflux for 12 h. After that time, the reaction was cooled to room temperature, diluted with 100 mL water, and extracted with ethyl acetate (3×75 mL). The organic layers were combined, dried with magnesium sulfate, gravity filtered, and the solvent was removed in vacuo. The resulting oil was chromatographed over silica in 1:49 methanol: chloroform yielding the mono-alkylated product (1.1 g, 62%) as well as the starting 1,4-benzodiazepin-2-one and bis-alkylated material. To a solution of the monoalkylated material (0.50 g, 1.42 mmol) in methylene chloride (30 mL) was added hexanoyl chloride (0.20 mL, 1.42 mmol) and the reaction was stirred for 0.25 h. The reaction was then diluted with methylene chloride (100 mL) and saturated aqueous sodium hydrogen carbonate (100 mL) was added. The aqueous portion was extracted with methylene chloride (2×75 mL) and the organics were combined, dried with magnesium sulfate, gravity filtered, and the solvent was removed in vacuo. The resulting oil was chromatographed over silica with 1:1 ethyl acetate:hexane, yielding a foam, giving 360 mg (64%) of the product. foam, $[\alpha]_d$+8.36° (c=0.61, MeOH).

Anal. Calcd. for $C_{27}H_{35}N_3O_2 \cdot 0.25$ mol $H_2O$: C, 71.42; H, 7.88; N, 9.25. Found: C, 71.47; H, 7.89; N, 9.12%.

Example 102

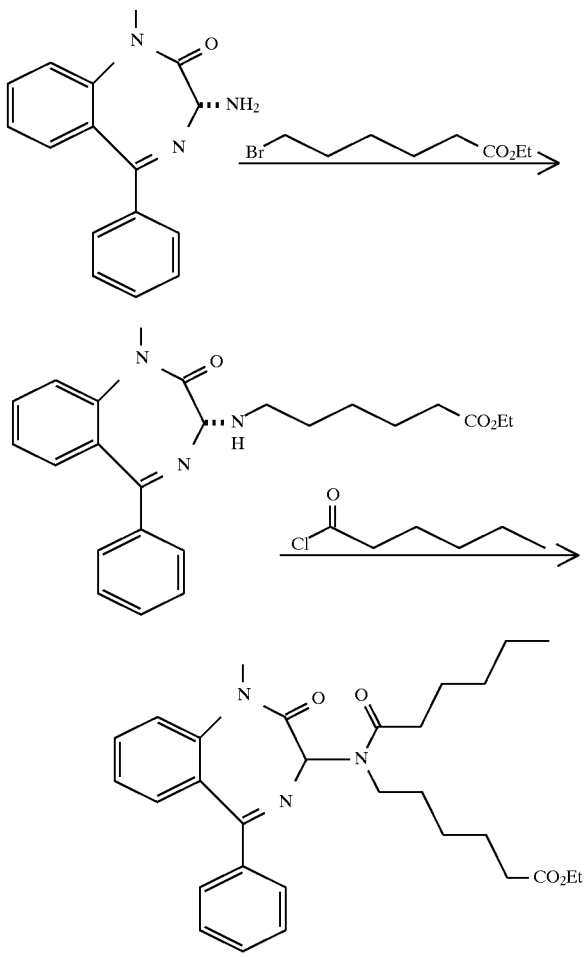

(+)-N-[2,3-Dihydro-1-methyl-2-oxo-5-phenyl-1H-1,4-benzodiazepin-3-yl]-N-(ethoxycarbonylpentyl)hexanamide 3-(R)-Amino-1,3-dihydro-1-methyl-5-phenyl-2H-1,4-benzodiazepin-2-one (1.33 g, 5.0 mmol) in acetonitrile (40 mL) was mixed with ethyl-6-bromohexanoate (0.89 mL, 5.0 mmol) and sodium hydrogen carbonate (2.0 g) was suspended in the mixture. The mixture was stirred and heated at reflux for 10 h. After that time, the reaction was cooled to room temperature, diluted with 100 mL water, and extracted with ethyl acetate (3×75 mL). The organic layers were combined, dried with magnesium sulfate, gravity filtered, and the solvent was removed in vacuo. The resulting oil was chromatographed in 1:49 methanol: chloroform, yielding the mono-alkylated product (0.56 g, 28%) as well as the starting 1,4-benzodiazepin-2-one and bis-alkylated material. To a solution of the mono-alkylated material (0.56 g, 1.37 mmol) in methylene chloride (20 mL) was added hexanoyl chloride (0.19 mL, 1.37 mmol) and the reaction was stirred for 0.25 h. The reaction was then diluted with methylene chloride (100 mL) and saturated aqueous sodium hydrogen carbonate (100 mL) was added. The aqueous portion was extracted again with methylene chloride (2×75 mL) and the organics were combined, dried with magnesium sulfate, gravity filtered, and the solvent was removed in vacuo. The resulting oil was chromatographed over silica with 1:1 ethyl acetate:hexane, yielding a foam, giving 0.40 g (58%) of the product.

m.p. 59°–65° C., $[\alpha]_d$ (+)52.7° (c=0.48, MeOH). Anal. Calcd. for $C_{30}H_{39}N_3O_4$·0.20 mol $CH_2Cl_2$: C, 69.4; H, 7.6; N, 8.04. Found: C, 69.44; H, 7.68; N, 7.71%.

The following compound was prepared in a manner substantially as described above except substituting ethyl bromoacetate for ethyl 6-bromohexanoate.

Example 103

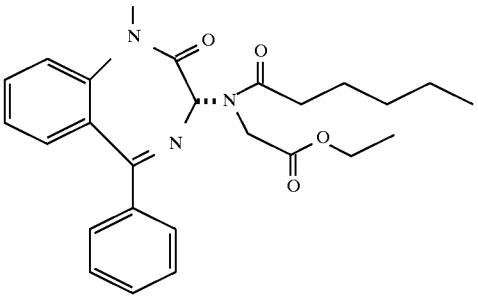

(+)-N-[2,3-Dihydro-1-methyl-2-oxo-5-phenyl-1H-1,4-benzodiazepin-3-yl]-N-(ethoxycarbonylmethyl)hexanamide foam, $[\alpha]_d$ +2.04° (c=0.98; MeOH).

Anal. Calcd. for $C_{26}H_{31}N_3O_4$: C, 69.47; H, 6.95; N, 9.35. Found: C, 69.41; H, 7.03; N, 9.26%.

Example 104

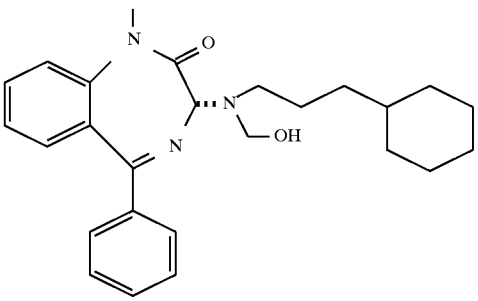

(+)-3-Cyclohexyl-N-[2,3-dihydro-1-methyl-2-oxo-5-phenyl-1H-1,4-benzodiazepin-3-yl]-N-(hydroxymethyl) propanamide (+)-3-Cyclohexyl-N-[2,3-dihydro-11-methyl-2-oxo-5-phenyl-1H-1,4-benzodiazepin-3-yl]propanamide (2.0 g, 5.0 mmol) was dissolved in tetrahydrofuran (30 mL), cooled to 0° C. and methyl magnesium chloride (3M, 2.0 mL) was added. After 0.25 h, paraformadehyde (0.15 g, 10 mmol) was added, and the mixture was allowed to warm to room temperature. The reaction was then diluted with ethyl acetate (150 mL) and saturated aqueous sodium hydrogen carbonate (150 mL) was added. The aqueous portion was extracted again with ethyl acetate (2×100 mL) and the organics were combined, dried with magnesium sulfate, gravity filtered, and the solvent was removed in vacuo. The resulting oil was chromatographed over silica with 1:1 ethyl acetate:hexane, yielding a foam (0.80 g, 37%).

foam, $[\alpha]_d$+124° (c=0.69, MeOH). Anal. Calcd. for $C_{26}H_{31}N_3O_3$: C, 72.03; H, 7.21; N, 9.69. Found: C, 71.66; H, 7.08; N, 9.78%.

The following compound was prepared in a manner substantially as described above starting from (+)-N-[2,3-dihydro-1-methyl-2-oxo-5-phenyl-1H-1,4-benzodiazepin-3-yl]hexanamide.

Example 105

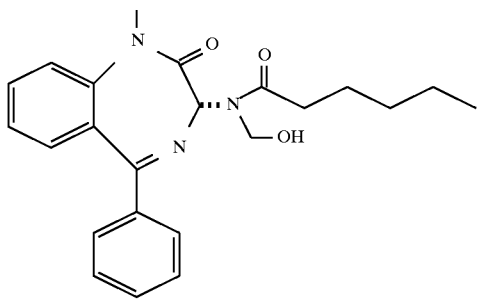

(+)-N-[2,3-Dihydro-1-methyl-2-oxo-5-phenyl-1H-1,4-benzodiazepin-3-yl]-N-(hydroxymethyl)hexanamide m.p. 154°–156° C., [α]$_d$+190.8° (c=0.24, MeOH). Anal. Calcd. for $C_{23}H_{27}N_3O_3$.0.30 mol $H_2O$: C, 69.26; H, 6.97; N, 10.53. Found: C, 69.29; H, 6.81; N, 10.6%.

Example 106

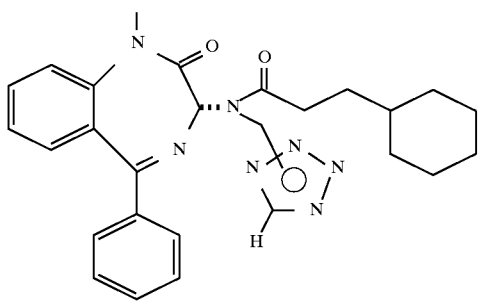

(+)-3-Cyclohexyl-N-[2,3-dihydro-1-methyl-2-oxo-5-phenyl-1H-1,4-benzodiazepin-3-yl]-N-(tetrazolylmethyl)propanamide (+)-3-Cyclohexyl-N-[2,3-dihydro-1-methyl-2-oxo-5-phenyl-1H-1,4-benzodiazepin-3-yl]-N-(hydroxymethyl)propanamide (0.67 g, 1.56 mmol) was dissolved in methylene chloride(100 mL), along with tetrazole (0.33 g, 4.7 mmol), and then N,N-diisopropyldibenzyl-phosphoramidite (1.07 g, 3.1 mmol). After 2 h, the mixture was diluted with methylene choride (150 mL), and extracted with saturated aqueous sodium hydrogen carbonate (3×100 mL). The organic layers were combined, dried with magnesium sulfate, gravity filtered, and the solvent was removed in vacuo. The resulting oil was chromatographed twice over silica with 1:1 ethyl acetate:hexane, yielding two constitutional isomers, a (65 mg, 9%) and b (56 mg, 7.5%).

Isomer A:

m.p. 96°–98° C., [α]$_d$+188.9° (c=0.19, MeOH). Anal. Calcd. for $C_{27}H_{31}N_7O_2$.0.30 mol TFA: C, 63.78; H, 6.07; N, 18.86. Found: C, 63.7; H, 6.12; N, 18.76%.

Isomer B:

m.p. 92°–95° C., [α]$_d$+81.3° (c=0.31, MeOH). Anal. Calcd. for $C_{27}H_{31}N_7O_2$0.35 mol TFA: C, 63.31; H, 6.01; N, 18.66. Found: C, 63.35; H, 6.02; N, 18.74%.

Example 107

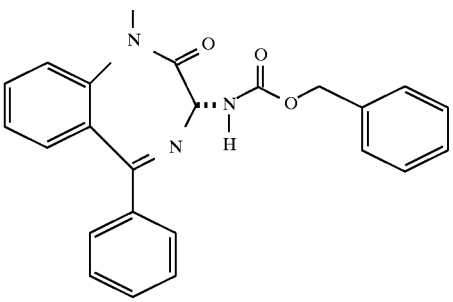

3R-(+)-3-(Benzyloxycarbonylamino)-2,3-dihydro-1-methyl-2-oxo-5-phenyl-1H-1,4-benzodiazepine To a stirring solution of 3-(R)-amino-1,3-dihydro-1-methyl-5-phenyl-2H-1,4-benzodiazepin-2-one (2.0 g, 7.5 mmol) in methylene chloride (45 mL) at 0° C. was added benzyl chloroformate (1.2 mL, 8.3 mmol) and the reaction was allowed to warm to room temperature. The reaction mixture was diluted with methylene chloride (150 mL), and extracted with saturated aqueous sodium hydrogen carbonate (150 mL). The aqueous portion was extracted with methylene chloride (2×100 mL) and the organics were combined, dried with magnesium sulfate, gravity filtered, and the solvent was removed in vacuo. The resulting oil was chromatographed over silica with 1:1 ethyl acetate:hexane, yielding a white foam (3.0 g, 99.7%) [α]$_d$+57.5° (c=1.17; MeOH). Anal. Calcd. for $C_{24}H_{20}N_3O_3$..0.70 mol $H_2O$ .0.15 mol $CHCl_3$: C, 67.62; H, 5.06; N, 9.8. Found: C, 67.6; H, 5.02; N, 9.75%.

The following compounds were prepared substantially as described in Example 81.

Example 108

N-[2,3-Dihydro-1-methyl-2-oxo-5-ethyl-1H-1,4-benzodiazepin-3-yl]-3-(2,4-dichlorophenyl)propanamide m.p. 156°–158° C. CHN: Anal. Calcd. for $C_{21}H_{21}Cl_2N_3O_2$.0.5$H_2O$: C, 59.02; H, 5.19; N, 9.83. Found: C, 58.99; H, 4.89; N, 9.88.

Example 109

N-[2,3-Dihydro-1-methyl-2-oxo-5-t-butyl-1H-1,4-benzodiazepin-3-yl]-3-(2,4-dichlorophenyl)propanamide m.p. 170°–171° C. CHN: Anal. Calcd. for $C_{23}H_{25}Cl_2N_3O_2$.0.7$H_2O$: C, 60.18; H, 5.80; N, 9.16. Found: C, 60.17; H, 5.30; N, 9.30.

Example 110

N-[2,3-Dihydro-1-methyl-2-oxo [4'-(4,4-dimethyl-2-oxazolinyl)phenyl]-1H-1,4-benzodiazepin-3-yl]-3-(2,4-dichlorophenyl)propanamide m.p. 188°–190° C. CHN: Anal. Calcd. for $C_{30}H_{28}N_4O_3Cl_2$: C, 63.95; H, 5.01; N, 9.94. Found: C, 63.96; H, 5.02; N, 10.08.

Example 111

N-[2,3-Dihydro-1-methyl-2-oxo-5-(4-methoxyphenyl)-1H-1,4-benzodiazepin-3-yl]-3-(2 4-dichlorophenyl)propanamide m.p. 188°–189° C. CHN: Anal. Calcd. for $C_{26}H_{23}Cl_2N_3O_3$ e0.45$H_2O$: C, 62.91; H, 4.67; N, 8.47. Found: C, 61.89; H, 4.78; N, 8.33.

Example 112
(+)-3,5-Dichloro-N-[3R-2,3-dihydro-2-oxo-5-phenyl-1-(2,2,2-trifluoroethyl)-1H-benzo[e][1,4]diazepin-3-yl]benzamide.

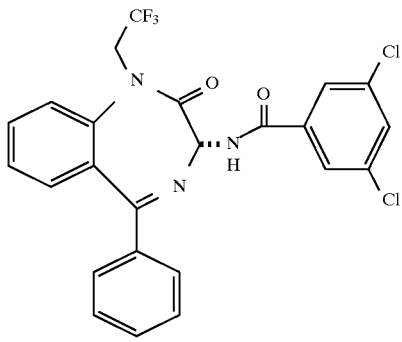

Step A:
Preparation of 2,3-dihydro-2-oxo-5-phenyl-1-(2,2,2-trifluoroethyl)-1H-benzo[e][1,4]diazepine.

A solution of 5-phenyl-1,4-benzodiazepine-2-one (*J. Org. Chem.*, 1962, 27, 3788)(50 g, 0.211 mole) in DMF (100 mL) was treated with cesium carbonate (103.5 g, 0.317 mole) and trifluoroethyl iodide (109.7 g, 0.525 mole). The mixture was stirred at 50° C. overnight. The reaction mixture was then poured into water (2 L and extracted with ethyl acetate (3×1 L. The combined ethyl acetate fractions were dried over anhydrous magnesium sulfate, filtered and concentrated at reduced pressure. The residue was crystallized from ethyl ether to give 45 g (68%) of the product. MP=130°–131° C.; $^1$H NMR (CDCl$_3$, 300 MHz) d 7.65–7.60 (m, 2H), 7.60–7.45 (m, 5H), 7.40–7.20 (m, 2H), 5.25 (dq, J=14, 8.6 Hz, 1H), 4.82 (d, J=10.5 Hz, 1H), 4.15 (app sextet, J=8.6 Hz, 1H), 3.81 (d, J=10.5 Hz, 1H)

Step B:
Preparation of 3-Azido-5-phenyl-1-(2,2,2-trifluoroethyl)-1H-benzo[e][1,4]diazepine.

To a stirring solution of 5-phenyl-1 (2,2,2-trifluoroethyl)-1H-benzo[e][1,4]diazepine (70 g, 0.22 mol) in THF (1500 mL) cooled to −70° C. was added potassium tert-butoxide (1.1 eq, 0.24 mol, 240 mL of a 1N solution in THF) dropwise over 15 min. A solution of 2,4,6-triisopropylbenzenesulfonylazide (74.8 g, 0.24 mol) in THF (250 ml) was added over 5 min. This was stirred for 10 minutes and acetic acid (40 mL, 0.63 mol) was added and the reaction allowed to warm to ambient temperature. The reaction was poured into satd. NaHCO$_3$ (1500 mL) and ethyl acetate (1 L). The phases were separated and the aqueous phase was extracted with ethyl acetate(500 mL). The combined organic layers were washed with water (500 mL) then brine (300 mL). The organic layers were dried with Na$_2$SO$_4$ and evaporated to a brown foam. This was triturated with ethyl ether to give 65 g of a white powder. The filtrate was concentrated and chromatographed over silica gel eluting with 30% ethyl acetate/hexane to give another 8.9 g. The combined yield was 74 g(93%). MP=159°–160° C.; $^1$H NMR (CDCl$_3$, 300 MHz) d 7.70–7.26 (m,9H), 5.28–5.12 (m,1H), 4.63 (s,1H), 4.35–4.10 (m,1H).

Step C:
Preparation of racemic 3-Amino-5-phenyl-1-(2,2,2-trifluoroethyl)-1H-benzo[e][1,4]diazepine.

To a stirring solution of 3-Azido-2-oxo-5-phenyl-1-(2,2,2-trifluoroethyl)-2,3-dihydro-1H-benzo[e][1,4]diazepine (83.4 mmol, 30 g) in 300 mL ethanol and 150 mL THF was added 10% Pd/C (10 wt %, 3.0 g). Hydrogen gas was bubbled through the solution for 8 h. The reaction was filtered and evaporated under reduced pressure. The residue was crystallized from ethyl ether to give 20.0 g of white crystals. Another 4 g was recovered from evaporation and recrystallization of the filtrates. Combined yield, 86.7%.

MP=141°–143° C.; $^1$H NMR (CDCl$_3$, 300 MHz) d 7.70–7.26 (m,9H), 5.28–5.12 (m,1H), 4.57 (s,1H), 4.35–4.10 (m,1H).

Step D:
Preparation of 2-Amino-N-[2-oxo-5-phenyl-1-(2,2,2-trifluoroethyl)-2,3-dihydro-1H-benzo[e][1,4]diazepin-3-yl]-3-phenylpropionamide To a stirring solution of 3-Amino-2-oxo-5-phenyl-1-(2,2,2-trifluoroethyl)-2,3-dihydro-1H-benzo[e][1,4]diazepine (92.2 mmol, 30.74 g) in DMF (300 mL) was added N-Benzyloxy-D-Phenylalanine (92.2 mmol, 27.6 g), 1-(3-Dimethylaminopropyl)-3-ethylcarbodiimide hydrochloride (0.12 mol, 22.95 g) and 1-hydroxybenztriazole hydrate (46 mmol, 6.23 g). This was stirred at room temperature for 2 h. The reaction was then diluted with 1 L of 10% KHSO$_4$ and extracted with ethyl acetate (2×600 mL). The organic layers were combined and washed with saturated sodium hydrogen carbonate (600 mL). They were dried with brine and sodium sulfate and evaporated under reduced pressure. 66.58 g of an orange foam, which contained ethyl acetate by NMR. NMR $^1$H (CDCl$_3$) d 7.75–7.18 (m, 20H), 5.62–5.55 (m,1H), 5.48–5.00 (m, 4H), 4.72–4.60 (m, 1H), 4.25–4.05 (m,1H) 3.32–3.05 (m, 2H). This material was carried on without further purification.

To a stirring solution of 2-(N-Benzyloxyamino)-N-[2-oxo-5-phenyl-1-(2,2,2-trifluoroethyl)-2,3-dihydro-1H-benzo[e][1,4]diazepin-3-yl]-3-phenyl propionamide in 1 L ethanol was added 10% Pd/C (15 wt %) and hydrogen was bubbled through the reaction for 2 h and then left stirring under 1 atm. hydrogen overnight. Hydrogen was bubbled through the reaction for an additional three hours the following morning. The reaction was then filtered, the catalyst was rinsed with 1 L methylene chloride and evaporated under reduced pressure. The resulting solid was dried under vacuum overnight to give 44.46 g of a white solid. This was chomatographed over silica, eluting with 1% MeOH:EtOAc. The pure upper R$_f$ fractions were collected and evaporated under reduced pressure. The mixed fractions were collected, evaporated and rechromatographed. The pure fractions were collected and combined with the above pure fractions to get a combined yield of 18.11 g, 83.5% of the upper Rf diastereomer. $^1$H NMR (CDCl$_3$,300 MHz) d 8.94 (d, J=8.6 Hz, 1H), 7.65–7.10 (m, 9H), 5.64 (d, J=8.6 Hz, 1H), 5.28–5.12 (m, 1H), 4.57 (s, 1H), 4.35–4.10 (m, 1H) 3.71 (dd, J=9.8 and 3.9 Hz, 1H), 3.34 ( dd, J=13.9 and 3.9 Hz, 1H), 2.79 (dd, J=13.9 and 10.0 Hz, 1H). The Absolute stereochemistry at C-3 of the benzodiazepine ring was determined to be (R) by X-Ray analysis.

The lower Rf material corresponding to C-3(S) was isolated as well.

Step E:
Preparation of 3(R)-(+)-3-Amino-5-phenyl-1-(2,2,2-trifluoroethyl)-1H-benzo[e][1,4]diazepine.

To a stirring solution of 2-Amino-N-[2-oxo-5-phenyl-1-(2,2,2-trifluoroethyl)-2,3-dihydro-1H-benzo[e][1,4]diazepin-3-yl]-3-phenylpropionamide (13.6 g, 28.3 mmol) in methylene chloride (136 mL) was added phenyl isothiocynate (3.87 mL, 34.0 mmol). This was stirred overnight at ambient temperature. The reaction was then cooled in ice, trifluoroacetic acid (2.73 mL, 0.283 mol) added and the reaction allowed to warm to ambient temperature. After stirring at ambient temperature for 2.5 hours the reaction was evaporated under reduced pressure, chromatographed with 90:10:1:1 methylene chloride:methanol:acetic acid:water. The low $R_f$ spot was collected and evaporated under reduced pressure with no heat. The residue was taken up in 600 mL methylene chloride and washed with 300 mL saturated $NaHCO_3$ and 300 mL water. The solution was dried over $Na_2SO_4$ and evaporated under reduced pressure. The residue was crystallized from ethyl acetate:hexanes to give 6.65 g of a white powder.

MP=162°–164° C.; $^1H$ NMR (CDCl$_3$, 300 MHz) d 7.70–7.26 (m,9H), 5.28–5.12 (m,1H), 4.57 (s,1H), 4.35–4.10 (m,1H). $[\alpha]_D$=+72.9° (c=0.7, MeOH)

The (−)-3S enantiomer was prepared in the same fashion from the Lower Rf product of Step D.

MP=156°–158° C.; $^1H$ NMR (CDCl$_3$, 300 MHz) d 7.70–7.26 (m,9H), 5.28–5.12 (m,1H), 4.57 (s,1H), 4.35–4.10 (m,1H). $[\alpha]_D$=−71.2° (c=0.66, MeOH)

Step F:
Preparation of (+)-3,5-Dichloro-N-[3R-2,3-dihydro-2-oxo-5-phenyl-1-(2,2,2-trifluoroethyl)-1H-benzo[e][1,4]diazepin-3-yl]benzamide:

To a stirring solution of (+)-3R-3-amino-5-phenyl-1-(2,2,2-trifluoroethyl)-1H-benzo[e][1,4]diazepine (5.6 g, 16.8 mmol) in DMF (50 mL) was added 1-(3-Dimethylaminopropyl-3-ethylcarbodiimide hydrochloride (4.44 g, 23.0 mmol), and 1-hydroxybenztriazole hydrate (3.11 g, 23.0 mmol) and 3,5-Dichlorobenzoic acid (3.21 g, 16.8 mmol). This was stirred at ambient temperature for 2 hours. The reaction was diluted with 500 mL satd. $NaHCO_3$ and extracted with 2×300 mL ethyl acetate. The combined organics were washed with 10% $KHSO_4$ (200 mL), brine (200 mL), dried over $Na_2SO_4$, and evaporated to a white foam. This was chromatographed over a 75×200 mm silica column eluting with 20% ethyl acetate:hexane. The pure fractions were collected and evaporated under reduced pressure to give 8.5 g of a white foam which was crystallized from 15% ethyl acetate:hexane to give 5.3 g of a white powder. mp=140°–143° C., $[\alpha]_D$=+47.9°; $^1H$ NMR (CDCl$_3$, 300 MHz) d 7.85–7.75 (m, 2H), 7.70–7.20 (m, 9H), 5.78 (d, J=8.1 Hz, 1 H), 5.30–5.15 (m, 1H), 4.30–4.15 (m, 1H) Analysis Calcd. for $C_{24}H_{16}Cl_2F_3N_3O_2$: C, 56.93; H, 3.19; N, 8.30; Found: C, 56.81; H, 3.17; N, 8.17.

The following examples were prepared by a procedure substantially as described for Example 1, Step F.

Example 113

(−)-2-(3,4-Dichlorophenyl)-N-[3R-2,3-dihydro-2-oxo-5-phenyl-1-(2,2,2-trifluoroethyl)-1H-benzo[e][1,4]diazepin-3-yl]acetamide.

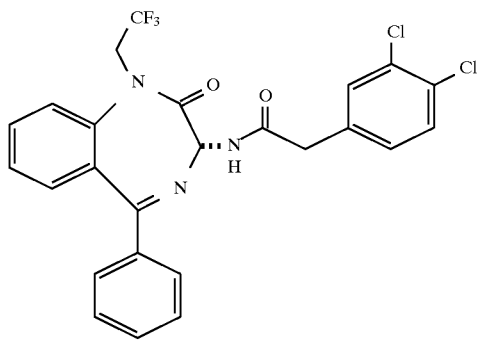

mp=219°–221° C.; $[\alpha]_D$=−10.8°; $^1H$ NMR (CDCl$_3$, 300 MHz) d 7.65–7.15 (m, 12H), 5.78 (d, J=8.1 Hz, 1H), 5.25–5.10 (m, 1H), 4.25–4.05 (m, 1H), 3.56 (s, 2H); Analysis Calcd. for $C_{25}H_{18}Cl_2F_3N_3O_2 \cdot 0.85H_2O$: C, 56.06; H, 3.71; N, 7.84. Found: C, 56.03; H, 3.53; N, 7.82.

Example 114

(−)-2-(3,5-Dichlorophenyl)-N-[3R-2,3-dihydro-2-oxo-5-phenyl-1-(2,2,2-trifluoroethyl)-1H-benzo[e][1,4]diazepin-3-yl]acetamide

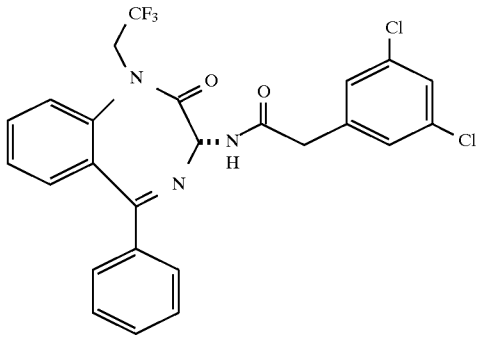

mp=93°–100° C., $[\alpha]_D$=−5.7°; $^1H$ NMR (CDCl$_3$, 300 MHz) d 7.65–7.15 (m, 12H), 5.78 (d, J=8.1 Hz, 1H), 5.25–5.10 (m, 1H), 4.25–4.05 (m, 1H), 3.65 (s, 2H); Analysis Calcd. for $C_{25}H_{18}Cl_2F_3N_3O_2$: C, 57.71; H, 3,49; N, 8.08; Found: C, 57.41; H, 3,48; N, 8.12.

Example 115

(−)-2-[3,5-Bis(trifluoromethyl)phenyl]-N-[3R-2,3-dihydro-2-oxo-5-phenyl-1-(2,2,2-trifluoroethyl)-1H-benzo[e][1,4]diazepin-3-yl]acetamide

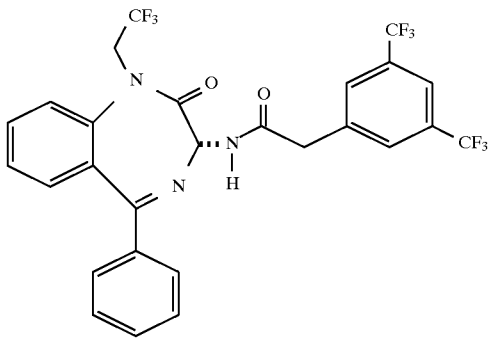

m.p. foam °C., $[\alpha]_D$=−9.7° (c=0.59, MeOH). Anal. Calcd. for $C_{27}H_{18}F_9N_3O_2 \cdot 0.75H2O$: C, 53.96; H, 3.27; N, 6.99. Found: C, 53.96; H, 3.1; N, 6.98%.

Example 116

(−)-2-(4-Trifluoromethylphenyl)-N-[3R-2,3-dihydro-2-oxo-5-phenyl-1-(2,2,2-trifluoroethyl)-1H-benzo[e][1,4]diazepin-3-yl]acetamide

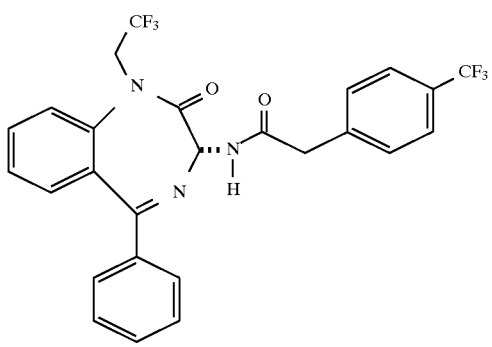

m.p. 253°–255° C., [α]$_D$=−9.2° (c=0.25, MeOH). Anal. Calcd. for C$_{26}$H$_{19}$F$_6$N$_3$O$_2$.0.05 ethyl ether 0.55H$_2$O: C, 59.03; H, 3.9; N, 7.88. Found: C, 59.05; H, 3.82; N, 7.78%.

Example 117

2-(3-Trifluoromethylphenyl)-N-[3R-2,3-dihydro-2-oxo-5-phenyl-1-(2,2,2-trifluoroethyl)-1H-benzo[e][1,4]diazepin-3-yl]acetamide

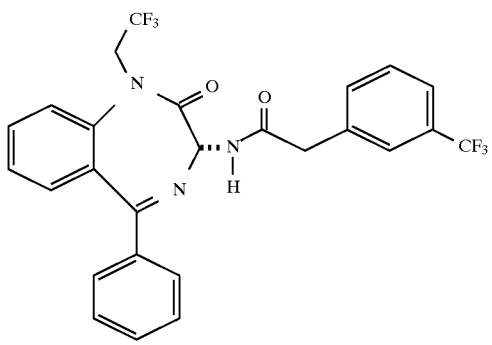

m.p. 172°–173° C., [α]$_D$=+5.9° (c=0.56, CHCl3). Anal. Calcd. for C$_{26}$H$_{19}$F$_6$N$_3$O$_2$.0.60H$_2$O: C, 58.89; H, 3.84; N, 7.92. Found: C, 58.92; H, 3.71; N, 7.98%.

Example 118

(+)-2-(2-Trifluoromethylphenyl)-N-[3R-2,3-dihydro-2-oxo-5-phenyl-1-(2,2,2-trifluoroethyl)-1H-benzo[e][1,4]diazepin-3-yl]acetamide

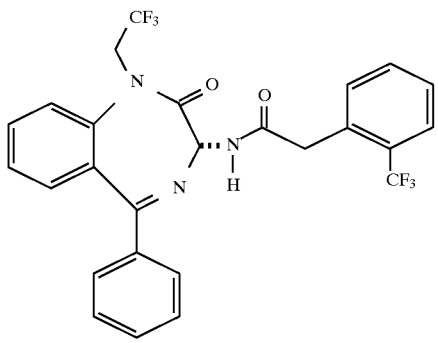

m.p. 170°–171° C., [α]$_D$=+9.0° (c=0.48, CHCl3). Anal. Calcd. for C$_{26}$H$_{19}$F$_6$N$_3$O$_2$.0.25H$_2$O: C, 59.6; H, 3.75; N, 8.02. Found: C, 59.64; H, 3.68; N, 7.97%.

Example 119

(−)-2-(2,4-Dichlorophenyl)-N-[3R-2,3-dihydro-2-oxo-5-phenyl-1-(2,2,2-trifluoroethyl)-1H-benzo[e][1,4]diazepin-3-yl]acetamide

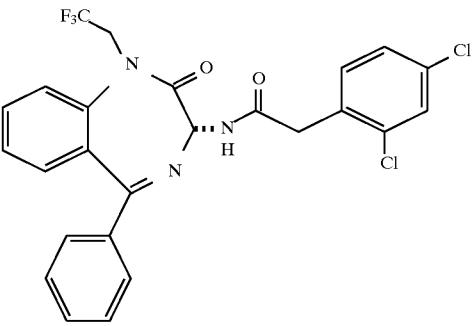

m.p. 143°–145° C., [α]$_D$=−22.6° (c=0.73; MeOH). Anal. Calcd. for C$_{25}$H$_{18}$N$_3$O$_2$Cl$_2$F$_3$: C, 57.71; H, 3,49; N, 8.08. Found: C, 57.75; H, 3.52; N, 8.09%.

Example 120

(−)-2-(3-Chlorophenyl)-N-[3R-2,3-dihydro-2-oxo-5-phenyl-1-(2,2,2-trifluoroethyl)-1H-benzo[e][1,4]diazepin-3-yl]acetamide

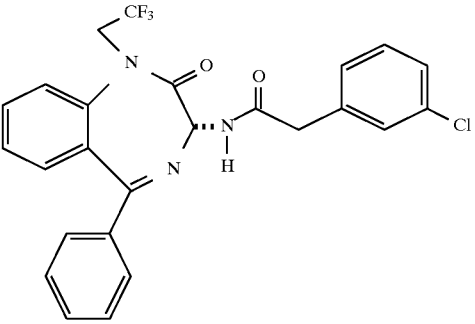

m.p. 188°–189° C., [α]$_D$=−5.4° (c=1.03, MeOH). Anal. Calcd. for C$_{25}$H$_{19}$ClF$_3$N$_3$O$_2$.0.10 ethyl ether: C, 61.84; H, 4.09; N, 8.52. Found: C, 61.84; H, 4.05; N, 8.5%.

Example 121

(−)-2-(4-Chlorophenyl)-N-[3R-2,3-dihydro-2-oxo-5-phenyl-1-(2,2,2-trifluoroethyl)-1H-benzo[e][1,4]diazepin-3-yl]acetamide

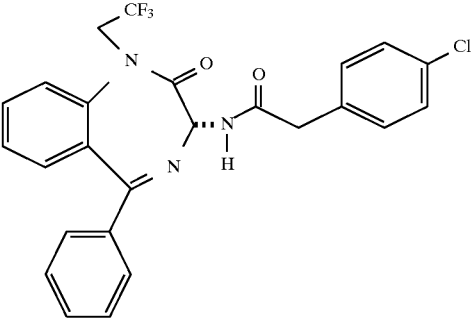

m.p. 246°–247° C., [α]$_D$=−10.1° (c=0.45, MeOH). Anal. Calcd. for C$_{25}$H$_{19}$ClF$_3$N$_3$O$_2$.0.20H20 0.15 ethyl ether: C, 61.42; H, 4.21; N, 8.39. Found: C, 61.46; H, 4.15; N, 8.39%.

Example 122
(−)-2-[2,4-Bis(trifluoromethyl)phenyl]-N-[3R-2,3-dihydro-2-oxo-5-phenyl-1-(2,2,2-trifluoroethyl)-1H-benzo[e][1,4]diazepin-3-yl]acetamide

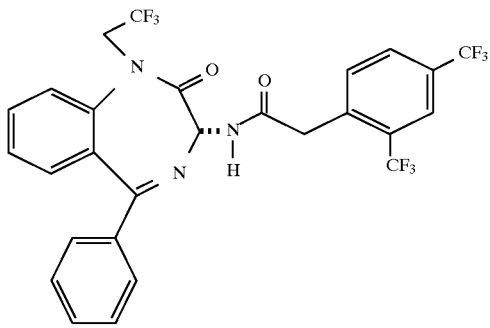

Step A.
2,4-Bis(trifluoromethyl)benzonitrile

To a stirring biphasic mixture of 100 mL ethanol and 250 mL of phosphate buffer (1 g of NaH₂PO₄·H₂O per 5 mL H₂O adjusted to pH=7.0 with 50% NaOH) and NaCN (81.3 mmol, 4.0 g) heated to 60° C. was added 2,4-bis(trifluoromethyl) benzyl bromide (32.5 mmol, 10 g) in 50 mL EtOH dropwise over 30 min. The reaction was heated at 60° C. for 24 h. The reaction was then evaporated under reduced pressure. The remaining aqueous was extracted with 2×150 mL EtOAc. The organic layers were combined, dried with brine and Na₂SO₄. The organic phase was evaporated under reduced pressure and the residue chromatographed over silica eluting with 10% EtOAc:Hexanes. The pure fractions were collected and evaporated to give 7.0 g of a pale yellow oil, 85.1% NMR ¹H (CDCl₃) d 8.0–7.85 (m,3H), 4.03 (s,2H)

Step B.
2,4-Bis(trifluoromethyl)phenyl acetic acid 2,4-Bis(trifluoromethyl)benzonitrile (41.5 mmol, 10.51 g) was taken up in 100 mL acetic acid, 50 mL conc. H₂SO₄, and 20 mL water. This was heated to 120° C. for 3 h. The reaction was then diluted with 1 L ice water, and extracted with 2×300 mL ethyl acetate. The combined organics were washed with 2×200 mL water, dried with brine and Na₂SO₄, and evaporated under reduced pressure. The residue was taken up in a minimum of diethyl ether and crystallized by adding sufficient hexane to precipatate the product. The solid was collected to give 7.74 g of 2,4-bis(trifluoromethyl) phenyl acetic acid as white crystals, 68.5%.NMR ¹H (CDCl₃) d 7.93 (s,1H), 7.80 (d, J=7.9 Hz, 1H), 7.55 (d, J=7.9 Hz, 1H), 3.94 (s,2H).

Step C.
Preparation of (−)-2-[2,4-Bis(trifluoromethyl)phenyl]-N-[3R-2,3-dihydro-2-oxo-5-phenyl-1-(2,2,2-trifluoroethyl)-1H-benzo[e][1,4]diazepin-3-yl]acetamide To a stirring solution the 3R-3-Amino-2-oxo-5-phenyl-1-(2,2,2-trifluoroethyl)-2,3-dihydro-1H-benzo[e][1,4]diazepine (28.4 mmol, 9.47 g) in DMF (100 mL) was added 2,4-Bis(trifluoromethyl)phenyl acetic acid (28.4 mmol, 7.74 g), 1-(3-Dimethylaminopropyl)-3-ethylcarbodiimide hydrochloride (42.6 mmol, 8.16 g) and 1-Hydroxybenztriazole hydrate (14.2 mmol, 1.92 g). This was stirred for 1 h at room temperature. The reaction was then diluted with 750 mL of 10% KHSO₄ and extracted with ethyl acetate (2×300 mL). The organic layers were combined and washed with saturated sodium hydrogen carbonate (1×600 mL). The organics were then dried with brine, and sodium sulfate and evaporated under reduced pressure. The residue was chromatographed over silica eluting with 20% EtOAc:Hexane. Pure fractions were collected and evaporated. The residue was taken up in 100 mL of warm 75% isopropanol:water. This was allowed to cool slowly and stirred overnight (16 hr) at room temperature. The suspension was cooled briefly to @5° C. and filtered. The white solid was dried overnight at 60° C. to give 10.5 g of material that melted at 132°–134° C. X-Ray diffraction confirms crystallinity.

NMR ¹H (CDCl₃) d 7.95–7.25 (m,13H), 5.60 (d,J=8.1 Hz, 1H), 5.30–5.10 (m,1H), 4.25–4.06 (m,1H), 3.96 (s,2H) Anal. Calcd. for C₂₇H₁₈F₉N₃O₂: C, 55.20; H, 3.09; N, 7.15. Found: C, 55.03; H, 3.14; N, 7.10%.

Example 123
(±)-2-(3,5-Dichlorophenyl)-N-[2,3-dihydro-2-oxo-5-phenyl-1-(2,2,2-trifluoroethyl)-1H-benzo[e][1,4]diazepin-3-yl]acetamide

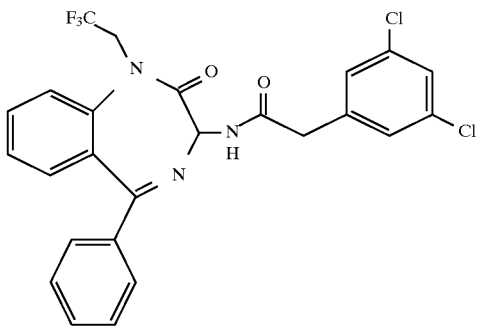

m.p. 219°–220° C. racemic Anal. Calcd. for C₂₅H₁₈N₃O₂Cl₂F₃: C, 57.71; H, 3,49; N, 8.08.
Found: C, 57.94; H, 3,48; N, 8.02%.

Example 124
2-(3,5-dichloro-4-methoxyphenyl)-N-[3R-2,3-dihydro-2-oxo-5-phenyl-1-(2,2,2-trifluoroethyl)-1H-benzo[e][1,4]diazepin-3-yl]acetamide

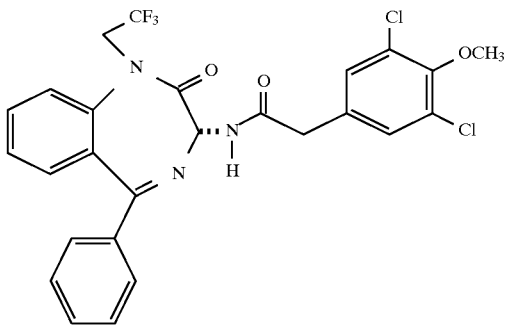

m.p. 100°–104° C., [α]_D=−8.9 (c=0.55, MeOH).
Anal. Calcd. for C₂₆H₂₀Cl₂F₃N₃O₃: C, 56.74; H, 3.66; N, 7.63.
Found: C, 55.67; H, 3,47; N, 7.41%.

The following examples were prepared by procedures substantially as described in example 1 except substituting the appropriate fluoro substituted aminobenzophenone in step A.

Example 125
(+)-2-(3,5-Dichlorophenyl)-N-[2,3-dihydro-5-(4-fluorophenyl)-2-oxo-1-(2,2,2-trifluoroethyl)-1H-benzo[e][1,4]diazepin-3-yl]acetamide

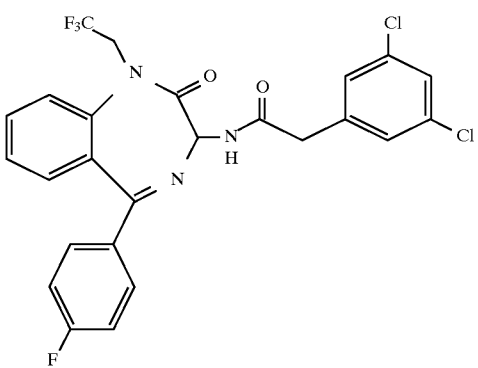

m.p. foam °C., [α]$_D$=+3.4° (c=0.55; MeOH). Anal. Calcd. for C$_{25}$H$_{17}$N$_3$O$_2$Cl$_2$F$_4$: C, 55.78; H, 3.18; N, 7.81. Found: C, 55.73; H, 3.25; N, 7.72%.

Example 126
(−)-2-(2,4-Dichlorophenyl)-N-[2,3-dihydro-5-(4-fluorophenyl)-2-oxo-1-(2,2,2-trifluoroethyl)-1H-benzo[e][1,4]diazepin-3-yl]acetamide

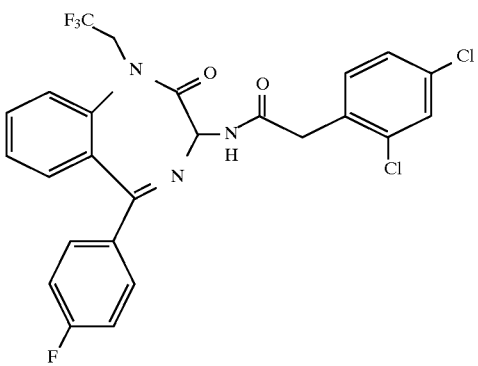

m.p. foam °C., [α]$_D$=−11° (c=0.68; MeOH). Anal. Calcd. for C$_{25}$H$_{17}$N$_3$O$_2$F$_4$: C, 55.78; H, 3.18; N, 7.81. Found: C, 55.82; H, 3,41; N, 7.42%.

Example 127
(+)-2-(3,5-Bis(trifluoromethyl)phenyl)-N-[2,3-dihydro-5-(4-fluorophenyl)-2-oxo-1-(2,2,2-trifluoroethyl)-1H-benzo[e][1,4]diazepin-3-yl]-acetamide

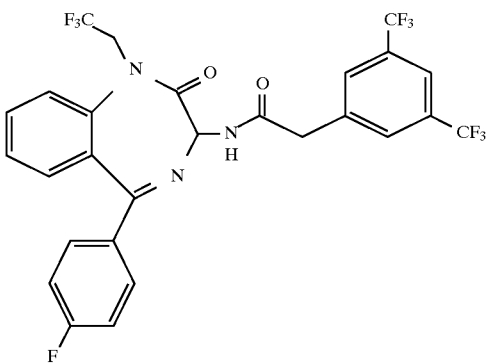

m.p. foam °C., [α]$_D$=+2.8° (c=0.67; MeOH). Anal. Calcd. for C$_{27}$H$_{17}$N$_3$O$_2$F$_{10}$: C, 53.56; H, 2.83; N, 6.94. Found: C, 53.56; H, 2.93; N, 6.91%.

Example 128
(−)-2-[2,4-Bis(trifluoromethyl)phenyl]-N-[2,3-dihydro-5-(4-fluorophenyl)-2-oxo-1-(2,2,2-trifluoroethyl)-1H-benzo[e][1,4]diazepin-3-yl]acetamide

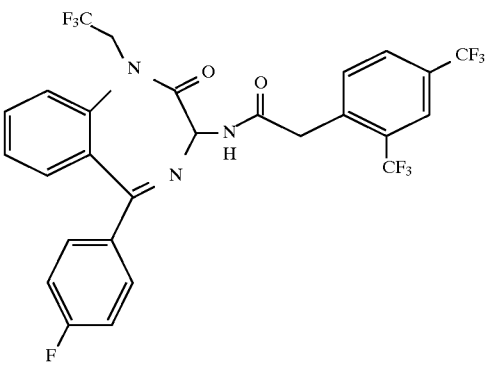

[α]$_D$=−14° (c=0.63; MeOH). Anal. Calcd. for C$_{27}$H$_{17}$N$_3$O$_2$F$_{10}$: C, 53.56; H, 2.83; N, 6.94. Found: C, 53.3; H, 2.89; N, 7.05%.

Example 129
3-Cyclohexyl-N-[2,3-dihydro-5-(2-fluorophenyl)-2-oxo-1-(2,2,2-trifluoroethyl-1H-benzo[e][1,4]diazepin-3-yl]propionamide

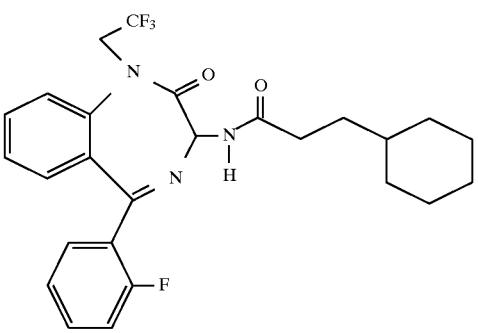

m.p. 202°–204° C. $^1$H NMR d (CDCl$_3$) 7.72 (m,8H), 5.65 (d,J=8.3 Hz, 1H), 5.35–5.08 (m,1H), 4.32–4.15 (m,1H), 2.37 (t,J=7.8 Hz, 2H), 1.80–1.55 (m,7H), 1.45-Anal. Calcd. for C$_{26}$H$_{27}$F$_4$N$_3$O$_2$: C, 63.8; H, 5.56; N, 8.58. Found: C, 63.82; H, 5.54; N, 8.56%.

Example 130
3,4-Dichloro-N-[2,3-dihydro-5-(2-fluorophenyl)-2-oxo-1-(2,2,2-trifluoroethyl)-1H-benzo[e][1,4]diazepin-3-yl]benzamide

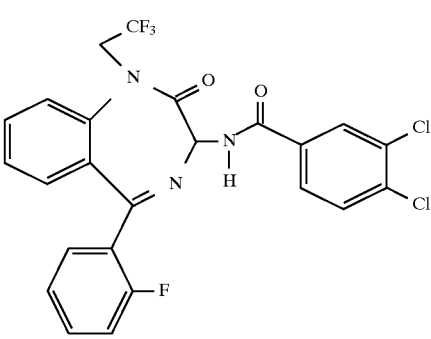

m.p. 168°–170° C. $^1$H NMR d (CDCl$_3$) 8.03 (d,J=2.0,1H), 7.86 (d,J=7.8 Hz, 1H), 7.78–7.05 (m,9H), 5.80 (d,J=7.8 Hz,

1H), 5.27–5.15 (m,1H), 4.35–4.20 (m,1H) Anal. Calcd. for C$_{24}$H$_{15}$Cl$_2$F$_4$N$_3$O$_2$: C, 54.98; H, 2.88; N, 8.01. Found: C, 54.96; H, 2.89; N, 8.12%.

What is claimed is:

1. A method of treating Meniere's disease in mammals, including humans, comprising the administration of a therapeutically effective dose of a compound of structural formula:

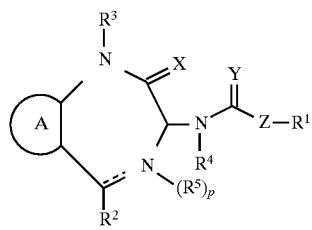

individual diastereomers, enantiomers and mixtures thereof, or a pharmaceutically acceptable salt thereof, wherein A is
1) thieno,
2) pyrido, or
3) benzo either unsubstituted or substituted with —NH$_2$, —NHSO$_2$(C$_{1-3}$ alkyl), C$_{1-3}$ alkyl or C$_{1-3}$ alkoxy;

X is
1) =O,
2) =S,
3) =N—NH$_2$,
4) =N—OH or
5) =H$_2$;

Y is
1) =O,
2) =N—CN or
3) =H$_2$;

Z is
1) C$_{1-6}$ alkylene, either straight or branch chain and either unsubstituted or substituted with phenyl or spiropiperidine,
2) C$_{2-4}$ alkenylene, either straight or branch chain,
3) —(CH$_2$)$_m$—W—(CH$_2$)$_n$— wherein m and n are independently 0, 1, 2, 3 or 4 and W is —O—, —S— or —NH,
4) 4—(5-methylisoxazole-3-yl),
5) C$_{3-6}$ cycloalkylene, or
6) single bond;

p is 0 or 1;

R$^1$ is
1) phenyl, either unsubstituted or substituted with one or two substituents selected from
   a) —NO$_2$,
   b) —Cl, Br, F, or I,
   c) —CF$_3$,
   d) —C$_{1-3}$ alkyl,
   e) —C$_{1-3}$ alkoxy,
   f) —CN,
   g) -methylenedioxy,
2) C$_{5-7}$ cycloalkyl,

3)

4) mono- or bicyclic heterocyclyl of 5 to 10 members one or two of which are sulfur, nitrogen or oxygen, the remaining being carbon, such as 2-thienyl, 2-furanyl, 2-indolyl, 2-quinoxolinyl, or 2-(2,3-dihydro benzofuranyl)
5) methyl, or
6) indan-5-yl;

R$^2$ is
1) phenyl, either unsubstituted or substituted with C$_{1-3}$ alkoxy or 4,4-dimethyloxazolin-2-yl,
2) C$_{1-4}$ alkyl, either straight or branched chain and either unsubstituted or substituted with C$_{1-3}$ alkoxy or C$_{1-3}$ alkoxy—C$_{1-3}$ alkoxy,
3) C$_{5-7}$ cycloalkyl,
4) 2- or 3-furyl,
5) 1-methylpiperidin-2-yl, or
6) if R$^2$ is phenyl, the 2-position of the phenyl can be joined to the 4-position nitrogen of the diazepine ring through a carbonyl group and the double bond between the 4-nitrogen and the 5-carbon becomes a single bond;

R$^3$ is
1) hydrogen or
2) C$_{1-6}$ alkyl, either straight or branched chain and either unsubstituted or substituted with —N(CH$_3$)$_2$, —OH, —CF$_3$, or
3) —CF$_3$;

R$^4$ is
1) hydrogen,
2) C$_{1-6}$ alkyl, the chain of carbon atoms of which can be interrupted by one or two non-adjacent oxygen atoms and which is either unsubstituted or substituted with C$_{1-3}$ alkoxycarbonyl, —OH or

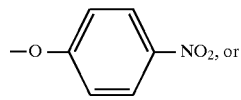

3) tetrazol-5-yl; and

R$^5$ is hydrogen or oxygen or is joined to R$^2$ to form the partial structure:

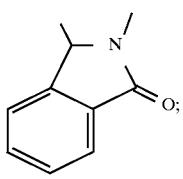

and the bond represented by ———— is:
1) a double bond when p is zero or when p is 1 and R$^5$ is oxygen, or
2) a single bond when R$^5$ is hydrogen or R$^5$ is joined to R$^2$ to form the partial structure:

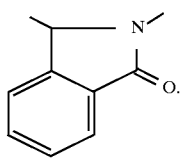

2. The method of claim 1 wherein
A is benzo either unsubstituted or substituted with —NH$_2$, —NHSO$_2$(C$_{1-3}$ alkyl), C$_{1-3}$ alkyl or C$_{1-3}$ alkoxy;
X and Y are O,
Z is
  1) C$_{1-6}$ alkylene, either straight or branch chain and either unsubstituted or substituted with phenyl or spiropiperidine,
  2) C$_{2-4}$ alkenylene, either straight or branch chain,
  3) —(CH$_2$)$_m$—W—(CH$_2$)$_n$— wherein m and n are independently 0, 1, 2, 3 or 4 and W is —O—, —S— or —NH ,
  4) 4-(5-methylisoxazole-3-yl),
  5) C$_{3-6}$ cycloalkylene, or
  6) single bond;
R$^1$ is
  1) phenyl, either unsubstituted or substituted with one or two substituents selected from
    a) —NO$_2$,
    b) —Cl, Br, F, or I,
    c) —CF$_3$,
    d) —C$_{1-3}$ alkyl,
    e) —C$_{1-3}$ alkoxy,
    f) —CN,
    g) -methylenedioxy,
  2) C$_{5-7}$ cycloalkyl,
  3)

4) mono- or bicyclic heterocyclyl of 5 to 10 members one or two of which are sulfur, nitrogen or oxygen, the remaining being carbon, such as 2-thienyl, 2-furanyl, 2-indolyl, 2-quinoxolinyl, or 2-(2,3-dihydro benzofuranyl)
  5) methyl, or
  6) indan-5-yl;
R$^2$ is
  1) phenyl, either unsubstituted or substituted with C$_{1-3}$ alkoxy or 4,4-dimethyloxazolin-2-yl,
  2) C$_{1-4}$ alkyl, either straight or branched chain and either unsubstituted or substituted with C$_{1-3}$ alkoxy or C$_{1-3}$ alkoxy-C$_{1-3}$ alkoxy,
  3) C$_{5-7}$ cycloalkyl,
  4) 2- or 3-furyl,
  5) 1-methylpiperidin-2-yl, or
  6) if R$^2$ is phenyl, the 2-position of the phenyl can be joined to the 4-position nitrogen of the diazepine ring through a carbonyl group and the double bond between the 4-nitrogen and the 5-carbon becomes a single bond;
R$^3$ is
  1) hydrogen or
  2) C$_{1-6}$ alkyl, either straight or branched chain and either unsubstituted or substituted with —N(CH$_3$)$_2$, —OH, —CF$_3$, or
  3) —CF$_3$;
R$^4$ is
  1) hydrogen,
  2) C$_{1-6}$ alkyl, the chain of carbon atoms of which can be interrupted by one or two non-adjacent oxygen atoms and which is either unsubstituted or substituted with C$_{1-3}$ alkoxycarbonyl, —OH or

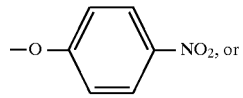

3) tetrazol-5-yl; and
R$^5$ is hydrogen or oxygen or is joined to R$^2$ to form the partial structure:

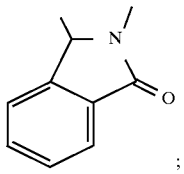

and the bond represented by is:
  1) a double bond when p is zero or when p is 1 and R$^5$ is oxygen, or
  2) a single bond when R$^5$ is hydrogen or R$^5$ is joined to R$^2$ to form the partial structure:

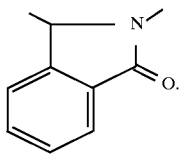

including individual diastereomers, enantiomers and mixtures thereof, or a pharmaceutically acceptable salt.

3. The method of claim 2 wherein
A is benzo either unsubstituted or substituted with —NH$_2$, —NH SO$_2$(C$_{1-3}$ alkyl), C$_{1-3}$ alkyl or C$_{1-3}$ alkoxy;
X and Y are O,
Z is
  1) C$_{1-6}$ alkylane, either straight or branch chain and either unsubstituted or substituted with phenyl or spiropiperidine,
  2) C$_{2-4}$ alkenylene, either straight or branch chain,
  3) —(CH$_2$)$_m$—W—(CH$_2$)$_n$— wherein m and n are independently 0, 1, 2, 3 or 4 and W is —O—, —S— or —NH,
  4) 4-(5-methylisoxazole-3-yl),
  5) C$_{3-6}$ cycloalkylene, or
  6) single bond;
R$^1$ is phenyl, either unsubstituted or substituted with one or two substituents selected from
    a) —NO$_2$,
    b) —Cl, Br, F, or I,
    c) —CF$_3$,
    d) —C$_{1-3}$ alkyl,
    e) —C$_{1-3}$ alkoxy,
    f) —CN,
    g) -methylenedioxy,
R$^2$ is phenyl, either unsubstituted or substituted with C$_{1-3}$ alkoxy or 4,4-dimethyloxazolin-2-yl,
R$^3$ is —CF$_3$ or C$_{1-6}$ alkyl, either straight or branched chain and either unsubstituted or substituted with —N(CH$_3$)$_2$, —OH, —CF$_3$;

$R^4$ and $R^5$ are hydrogen; including individual diastereomers, enantiomers and mixtures thereof, or a pharmaceutically acceptable salt.

4. The method of claim 3 wherein

A is unsubstituted benzo;

$R^1$ is phenyl, either unsubstituted or substituted with one or two substituents selected from
 a) $-NO_2$,
 b) $-Cl$, Br, F, or I,
 c) $-CF_3$,
 d) $-C_{1-3}$ alkyl,
 e) $-C_{1-3}$ alkoxy,
 f) $-CN$,
 g) -methylenedioxy, $R^2$ is phenyl, either unsubstituted or substituted with $C_{1-3}$ alkoxy or 4,4-dimethyloxazolin-2-yl, $R^3$ is $-CF_3$ or $C_{1-6}$ alkyl, either straight or branched chain and either unsubstituted or substituted with $-N(CH_3)_2$, $-OH$, $-CF_3$;

$R^4$ and $R^5$ are hydrogen;

including individual diastereomers, enantiomers and mixtures thereof, or a pharmaceutically acceptable salt.

5. The method of claim 4 wherein the compound is (−)-2-[2,4-Bis(trifluoromethyl)phenyl]-N-[3R-2,3-dihydro-2-oxo-5-phenyl-1-(2,2,2-trifluoroethyl)-1H-benzo[e][1,4]diazepin-3-yl]acetamide

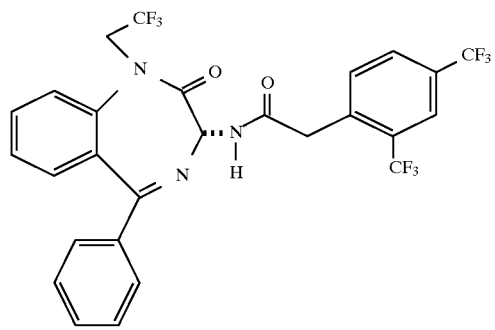

6. The method of claim 4 wherein the compound is 3,4-Dichloro-N-[2,3-dihydro-5-(2-fluorophenyl)-2-oxo-1-(2,2,2-trifluoro-ethyl)-1H-benzo[e][1,4]diazepin-3-yl]benzamide

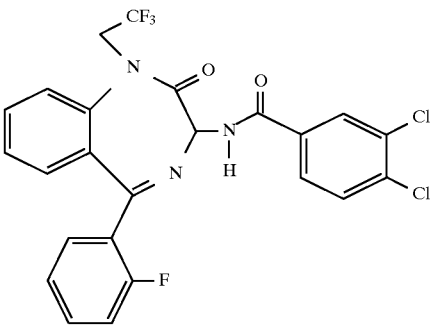

7. The method of claim 4 wherein the compound is (−)-2-(2,4-Dichlorophenyl)-N-[3R-2,3-dihydro-2-oxo-5-phenyl-1-(2,2,2-trifluoroethyl)-1H-benzo[e][1,4]diazepin-3-yl]acetamide

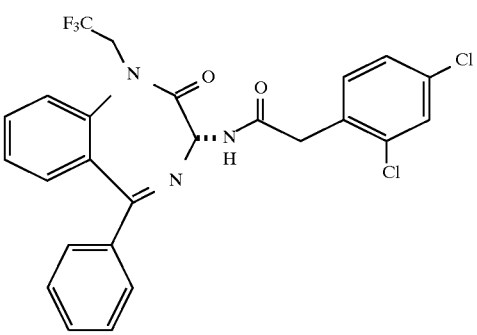

* * * * *